US005385917A

United States Patent [19]

Ueno et al.

[11] Patent Number: 5,385,917

[45] Date of Patent: Jan. 31, 1995

[54] CARBOXYLIC ACID DERIVATIVES

[75] Inventors: Hiroaki Ueno, San Diego, Calif.; Masahiko Morioka, Machida; Fumiko Hatanaka, Yokohama, both of Japan

[73] Assignee: Mitsubishi Kasei Corporation, Tokyo, Japan

[21] Appl. No.: 92,055

[22] Filed: Jul. 16, 1993

[30] Foreign Application Priority Data

Jul. 17, 1992 [JP] Japan .................................. 4-190991

[51] Int. Cl.$^6$ ...................... A01N 43/40; C07C 229/00

[52] U.S. Cl. .................................... 514/325; 514/459; 514/480; 514/481; 562/455; 562/441; 562/457; 562/427; 562/456; 562/428; 562/430; 560/45; 560/48; 594/172; 546/221; 546/234; 549/420

[58] Field of Search .............. 562/455, 441, 457, 427, 562/428, 430, 456; 514/325, 459, 480, 481; 544/172; 546/221, 234; 549/420

[56] References Cited

FOREIGN PATENT DOCUMENTS 0291245 11/1988 European Pat. Off. .

0294035 12/1988 European Pat. Off. .

OTHER PUBLICATIONS

CA72(17):90063m. Boehringer et al, "Antineoplastic N-acyl-4-aminophenoxy alkylcarboxylic acid derivatives", FR 1571198 690613, 1969, Abstract only, See Action.

*Primary Examiner*—Marianne M. Cintins

*Assistant Examiner*—Keith MacMillan

*Attorney, Agent, or Firm*—Wenderoth, Lind & Ponack

[57] ABSTRACT

Carboxylic acid derivatives of the formula:

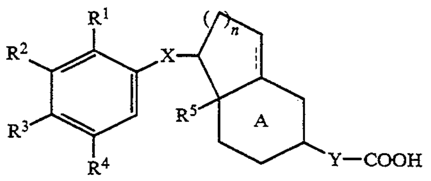

(I)

are provided, which are useful for treatment of androgen dependent diseases.

6 Claims, No Drawings

CARBOXYLIC ACID DERIVATIVES

The present invention relates to novel carboxylic acid derivatives. More particularly, this invention relates to novel carboxylic acid derivatives having 5α-reductase inhibitory activity useful for treating benign prostatic hyperplasia, acne, seborrhea, female hirsutism, prostatic carcinoma, male alopecia, or the like, caused by excessive production of dihydrotestosterone (hereinafter referred to as "DHT").

Androgen dependent diseases which represent unfavorable physiological symptoms such as benign prostatic hyperplasia, acne, seborrhea, female hirsutism, male alopecia, or the like are caused by excessive accumulation of androgenic hormones in the metabolic system.

It has long been known that DHT is essential for differentiation, development and maintenance of prostatic tissue. It has also been well known that the active androgen of males targets organs such as prostate sebaceous gland, hair-root is DHT.

DHT is produced from testosterone by the action of a testosterone 5α-hydrogenating enzyme, "5α-reductase", in the above target organs. Therefore, testosterone is a kind of pro-hormone in androgen-depending tissues such as prostate gland, and 5α-reductase plays an important role for the biosynthesis of DHT.

The importance of DHT concentration has recently been recognized in diseases which appear to be caused by an excess of male hormone, and a lot of 5α-reductase inhibitors have been reported, which include steroid derivatives such as 4-aza-steroid derivatives [JMC, 27, 1690 (1984)], 3-carboxylic acid steroid derivatives [Bioorganic chem, 17, 372 (1989)], JMC, 33, 937 (1990)], 3-phosphonic acid steroid derivatives [Japanese Patent Publication Kokai Hei 2-212499; Hei 2-225496], 3-sulfonic acid steroid derivatives [Japanese Patent Publication Kokai Hei 2-225494], 3-nitrosteroid derivatives [Japanese Patent Publication Kokai Hei 3-118325], non-steroid agents such as benzoylaminophenoxybutanoic acid derivatives [Japanese Patent Publication Kokai Hei 1-156950; Hei 1-139558], WS-9659 A and B originating from microorganisms [The Journal of Antibiotics, 1230, 1235, 1989], and the like.

The 5α-reductase inhibitors listed above are classified in two groups, namely steroid derivatives and non-steroid derivatives. The steroid derivatives have a problem of inducing side effects although they exhibit excellent pharmacological activities. On the other hand, non-steroid derivative having sufficient activity has not been discovered yet.

As the result of extensive study for providing nonsteroid compounds having high activity as 5α-reductase inhibitors, the present inventors have found that specific carboxylic acid derivatives have an excellent activity. The present invention has been completed on the basis of such finding.

Thus, the present invention provides carboxylic acid derivatives of the following general formula (I):

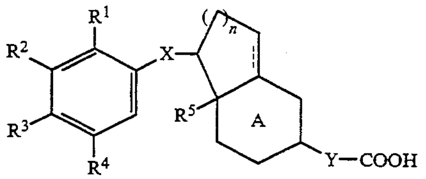

(I)

Wherein $R^1$, $R^2$, $R^3$ and $R^4$ each independently represent hydrogen atom, halogen atom, adamantyl group, optionally substituted $C_1$–$C_{14}$ alkyl group, optionally substituted $C_3$–$C_{10}$ cycloalkyl group, optionally substituted $C_1$–$C_{14}$ alkoxy group, optionally substituted heterocyclic group, —$OR^6$ ($R^6$ represents hydrogen atom, adamantyl group, optionally substituted $C_3$–$C_{10}$ cycloalkyl group or optionally substituted heterocyclic group), or a group of the formula:

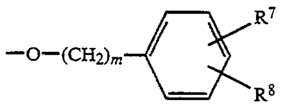

wherein $R^7$ and $R^8$ each independently represent hydrogen atom, $C_1$–$C_6$ alkyl group, $C_3$–$C_8$ cycloalkyl group, —$CONR^9R^{10}$ ($R^9$ and $R^{10}$ each independently represent hydrogen atom or $C_1$–$C_6$ alkyl group) or, when $R^7$ and $R^8$ are adjacent, they may form $C_1$–$C_6$ alkylene group, and m represents 0 or 1, or, the adjacent two substituents selected from $R^1$, $R^2$, $R^3$ and $R^4$ may form a group of the formula:

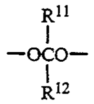

wherein $R^{11}$ and $R^{12}$ each independently represent hydrogen atom, $C_1$–$C_6$ alkyl group or $C_3$–$C_8$ cycloalkyl group or they may form, taken together, $C_2$–$C_8$ alkylene group, a group of the formula: —$OCH_2CH_2O$— or optionally substituted $C_3$–$C_4$ alkylene group, $R^5$ represents hydrogen atom or $C_1$–$C_5$ alkyl group, X represents —$CONR^{13}$— or —$SO_2NR^{13}$— ($R^{13}$ represents hydrogen atom or $C_1$–$C_6$ alkyl group), Y represents a single bond, —$OCH_2$— or —CH=CH—, A ring may form benzene ring, cyclohexene ring or cyclohexadiene ring, the dotted line represents a single bond or double bond, and n represents 1 or 2, with the proviso that when the carbon atom to which $R^5$ is attached has a double bond, then $R^5$ is not present, or pharmaceutically acceptable salts thereof.

The present invention will be explained in detail below.

The present invention relates to the carboxylic acid derivatives of the following general formula (I):

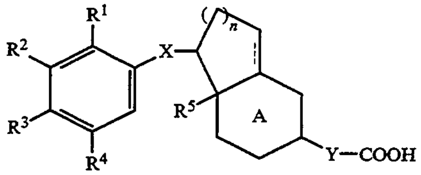
(I)

wherein $R^1$, $R^2$, $R^3$ and $R^4$ each independently represent hydrogen atom, halogen atom (iodine atom, fluorine atom, chlorine atom, bromine atom), adamantyl group, $C_1$–$C_{14}$ alkyl group (methyl group, pentyl group, nonyl group, tetradecyl group, etc.) optionally having one or more substituents selected from 5 or 6 membered heterocyclic ring containing 1 or 2 hetero atoms selected from oxygen atom, sulfur atom and nitrogen atom, such as tetrahydrofuran ring, imidazoline ring, piperidine ring, dithian ring, thiomorpholine ring, etc.; $C_3$–$C_{10}$ cycloalkyl group (cyclopropyl group, cyclohexyl group, cyclodecyl group, etc.) and adamantyl group, $C_3$–$C_{10}$ cycloalkyl group (cyclopropyl group, cyclohexyl group, cyclodecyl group, etc.) optionally having one or more substituents selected from $C_1$–$C_6$ alkyl group (methyl group, butyl group, hexyl group, etc.), $C_1$–$C_{14}$ alkoxy group (methoxy group, pentyloxy group, nonyloxy group, tetradecyloxy group, etc.) optionally having one or more substituents selected from 5 or 6 membered heterocyclic ring containing 1 or 2 hetero atoms selected from oxygen atom, sulfur atom and nitrogen atom, such as tetrahydrofuran ring, imidazoline ring, piperidine ring, dithian ring, thiomorpholine ring, etc.), $C_3$–$C_{10}$ cycloalkyl group (cyclopropyl group, cyclohexyl group, cyclodecyl group, etc.) and adamantyl group, 5 or 6 membered heterocyclic ring containing 1 or 2 hetero atoms selected from oxygen atom, sulfur atom and nitrogen atom, such as tetrahydrofuran ring, imidazoline ring, piperidine ring, dithian ring, thiomorpholine ring, etc., optionally having one or more substituents selected from $C_1$–$C_6$ alkyl group (methyl group, butyl group, hexyl group, etc.), a group: $—OR^6$ {$R^6$ represents hydrogen atom, adamantyl group, $C_3$–$C_{10}$ cycloalkyl group (cyclopropyl group, cyclohexyl group, cyclodecyl group, etc.) optionally having one or more substituents selected from $C_1$–$C_6$ alkyl group (methyl group, butyl group, hexyl group, etc.) or 5 or 6 membered heterocyclic ring containing 1 or 2 hetero atoms selected from oxygen atom, sulfur atom and nitrogen atom (tetrahydrofuran ring, imidazoline ring, piperidine ring, dithian ring, thiomorpholine ring, etc.) optionally having one or more substituents selected from $C_1$–$C_6$ alkyl group (methyl group, butyl group, hexyl group, etc.) and $C_2$–$C_6$ acyl group (acetyl group, isobutyryl group, isovaleryl group, etc.)} or a group:

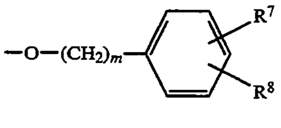

wherein $R^7$ and $R^8$ each independently represent hydrogen atom, $C_1$–$C_6$ alkyl group (methyl group, butyl group, hexyl group, etc. ), $C_3$–$C_8$ cycloalkyl group (cyclopropyl group, cyclohexyl group, cyclooctyl group, etc. ), $—CONR^9R^{10}$ [$R^9$ and $R^{10}$ each independently represent hydrogen atom or $C_1$–$C_6$ alkyl group (methyl group, butyl group, hexyl group, etc.), or, when $R^7$ and $R^8$ are adjacent, they may form $C_1$–$C_6$ alkylene group (methylene group, trimethylene group, hexamethylene group, etc.), and m represents 0 or 1}, or, the two adjacent substituents selected from $R^1$, $R^2$, $R^3$ and $R^4$ may form a group of the formula:

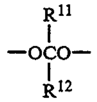

wherein $R^{11}$ and $R^{12}$ each independently represent hydrogen atom, $C_1$–$C_6$ alkyl group (methyl group, butyl group, hexyl group, etc.) or $C_3$–$C_8$ cycloalkyl group (cyclopropyl group, cyclopentyl group, cyclooctyl group, etc.) or, they may form $C_2$–$C_8$ alkylene group (ethylene group, pentamethylene group, octamethylene group, etc.), a group: $—OCH_2CH_2O—$ or $C_3$–$C_4$ alkylene group (trimethylene group, tetramethylene group) optionally having one or more substituents selected from $C_1$–$C_6$ alkyl group (methyl group, butyl group, hexyl group, etc.) and $C_3$–$C_8$ cycloalkyl group (cyclopropyl group, cyclohexyl group, cyclooctyl group, etc.);

$R^5$ represents hydrogen atom or $C_1$–$C_6$ alkyl group (methyl group, butyl group, hexyl group, etc.), X represents $—CONR^{13}—$ or $—SO_2NR^{13}—$ [$R^{13}$ represents hydrogen atom or $C_1$–$C_6$ alkyl group (methyl group, butyl group, hexyl group, etc.)];

Y represents a single bond, $—OCH_2—$ or $—CH=CH—$;

A ring may form a benzene ring or cyclohexadiene ring;

the dotted line represents a single bond or double bond; and n represents 1 or 2, with the proviso that, when the carbon to which $R^5$ is attached has a double bond, then $R^5$ is not present, or pharmaceutically acceptable salts thereof.

Of the compounds of the present invention, preferable is a compound of the formula (I) in which $R^1$, $R^2$, $R^3$ and $R^4$ each independently represent hydrogen atom; halogen atom; $C_1$–$C_{14}$ alkyl group optionally having one or more substituents selected from 5 or 6 membered heterocyclic group containing 1 or 2 hetero atoms selected from oxygen atom, sulfur atom and nitrogen atom, and $C_3$–$C_{10}$ cycloalkyl group; $C_1$–$C_{14}$ alkoxy group optionally having one or more $C_3$–$C_{10}$ cycloalkyl group; $—OR^6$ [$R^6$ represents $C_3$–$C_{10}$ cycloalkyl group optionally having one or more $C_1$–$C_6$ alkyl group; or 5 or 6 membered heterocyclic group containing 1 or 2 hetero atoms selected from oxygen atom, sulfur atom and nitrogen atom, and optionally having one or more $C_1$–$C_6$ alkyl groups] or a group of the formula:

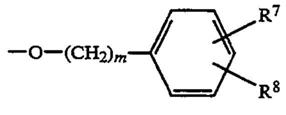

wherein $R^7$ and $R^8$ each independently represent hydrogen atom, $C_1$-$C_6$ alkyl group, $C_3$-$C_8$ cycloalkyl group, —$CONR^9R^{10}$ ($R^9$ and $R^{10}$ each independently represent hydrogen atom or $C_1$-$C_6$ alkyl group) or, when $R^7$ and $R^8$ are adjacent, they may form $C_1$-$C_6$ alkylene group, and m represents 0 or 1), $R^5$ represents $C_1$-$C_6$ alkyl group, X represents —$CONR^{13}$— or —$SO_2NR^{13}$— ($R^{13}$ represents hydrogen or $C_1$-$C_6$ alkyl group), Y represents a single bond, —$OCH_2$— or —CH=CH—, A ring may form a benzene ring or cyclohexene ring, the dotted line represents a single bond or double bond, and n represents 1 or 2.

Particularly preferable is a compound of the formula (I) in which $R^1$, $R^2$, $R^3$ and $R^4$ each independently represent hydrogen atom; halogen atom; $C_1$-$C_{14}$ alkyl group optionally having one or more $C_3$-$C_{10}$ cycloalkyl groups; $C_1$-$C_{14}$ alkoxy group optionally having one or more $C_3$-$C_{10}$ cycloalkyl group; or —$OR^6$ ($R^6$ represents $C_3$-$C_{10}$ cycloalkyl group optionally having one or more $C_1$-$C_6$ alkyl group); $R^5$ represents $C_1$-$C_6$ alkyl group, X represents —$CONR^{13}$— ($R^{13}$ represents hydrogen or $C_1$-$C_6$ alkyl group); Y represents a single bond; A ring represents cyclo-hexene ring; the dotted line represents a single bond, and n represents 1 or 2.

Most preferable is a compound of the formula (I) in which $R^1$, $R^2$, $R^3$ and $R^4$ each independently represent hydrogen atom or $C_1$-$C_{14}$ alkoxy group; $R^5$ represents $C_1$-$C_6$ alkyl group; X represents —$CONR^{13}$— ($R^{13}$ represents hydrogen atom); Y represents a single bond; A ring represents a cyclohexene ring; the dotted line represents a double bond; and n represents 2.

The compounds of the general formula (I) above may contain an asymmetric carbon atom, and racemic mixture and optical isomers are included in the present invention.

The compounds of the present invention are illustrated in Tables 1-4 below.

TABLE 1
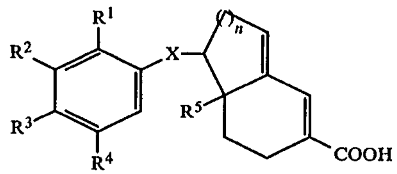
| Compd. No. | $R^1$ | $R^2$ | $R^3$ | $R^4$ | $R^5$ | X | n |
|---|---|---|---|---|---|---|---|
| 1 | H | H | 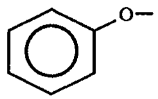 | H | —Me | —CONH— | 2 |
| 2 | H | H | 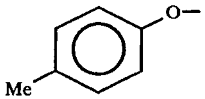 | H | —Me | —CONH— | 2 |
| 3 | H | H | 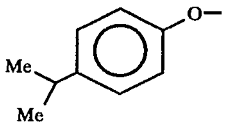 | H | —Me | —CONH— | 2 |
| 4 | H | H | 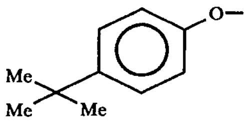 | H | —Me | —CONH— | 2 |
| 5 | H | H | 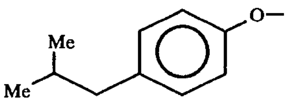 | H | —Me | —CONH— | 2 |
| 6 | H | H | 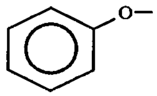 | H | —Me | —CONMe— | 2 |

TABLE 1-continued
| | | | | | | | |
|---|---|---|---|---|---|---|---|
| 7 | H | H | 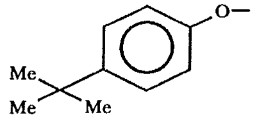 | H | —Me | —CONEt— | 2 |
| 8 | H | H | 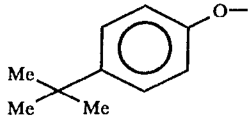 | H | —Me | —CONH— | 1 |
| 9 | H | H | 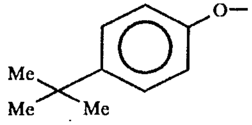 | H | —Me | —CONMe— | 1 |
| 10 | H | 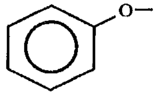 | H | H | —Me | —CONH— | 2 |
| 11 | H | 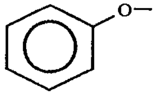 | H | H | —Me | —CONH— | 1 |
| 12 | 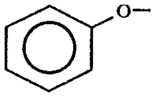 | H | H | H | —Me | —CONH— | 2 |
| 13 | 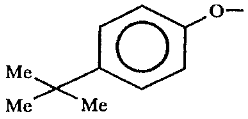 | H | H | H | —Me | —CONH— | 2 |
| 14 | 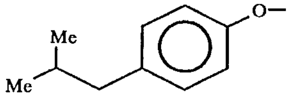 | H | H | H | —Me | —CONH— | 2 |

TABLE 1-continued
| | | | | | | | |
|---|---|---|---|---|---|---|---|
| 15 | 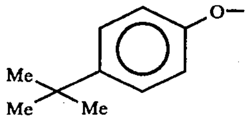 | H | H | H | —Me | —CONH— | 1 |
| 16 | H | 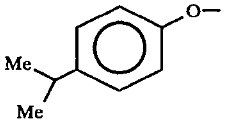 | H | H | —Me | —CONH— | 2 |
| 17 | H | 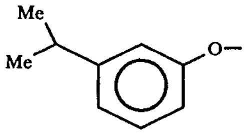 | H | H | —Me | —CONH— | 2 |
| 18 | H | 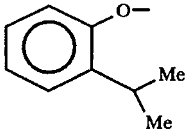 | H | H | —Me | —CONH— | 2 |
| 19 | H | 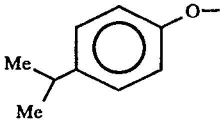 | H | H | —Me | —CONMe— | 2 |
| 20 | H | 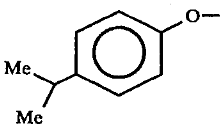 | H | H | —Me | —CONH— | 1 |
| 21 | H | 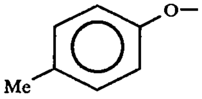 | H | H | —Me | —CONH— | 2 |

TABLE 1-continued
| | | | | | | | |
|---|---|---|---|---|---|---|---|
| 22 | H | 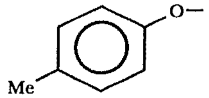 | H | H | —Me | —CONH— | 1 |
| 23 | H | 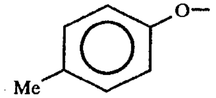 | H | H | —Me | —CONMe— | 2 |
| 24 | H | 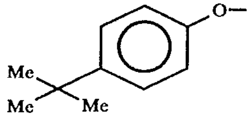 | H | H | —Me | —CONH— | 2 |
| 25 | H | 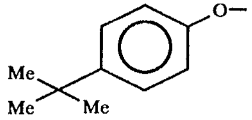 | H | H | —Me | —CONH— | 1 |
| 26 | H | 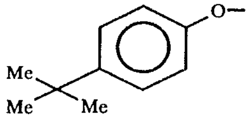 | H | H | —Me | —CONMe— | 2 |
| 27 | —OH | 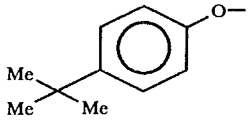 | H | H | —Me | —CONH— | 2 |
| 28 | —Me | 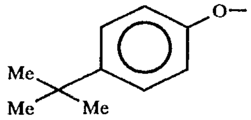 | H | H | —Me | —CONH— | 2 |
| 29 | —Et | 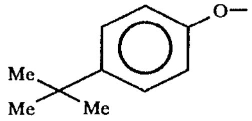 | H | H | —Me | —CONH— | 2 |

TABLE 1-continued
| | | | | | | | |
|---|---|---|---|---|---|---|---|
| 30 | H | 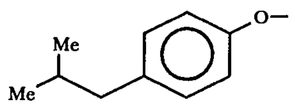 | H | H | —Me | —CONH— | 2 |
| 31 | H | 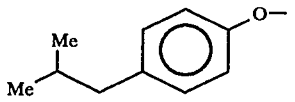 | H | H | —Me | —CONH— | 1 |
| 32 | H | 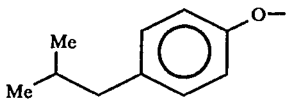 | H | H | —Me | —CONMe— | 2 |
| 33 | H | 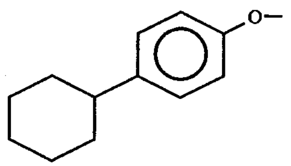 | H | H | —Me | —CONH— | 2 |
| 34 | H | 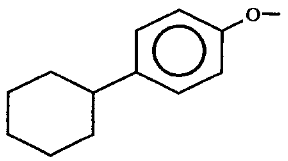 | H | H | —Me | —CONH— | 1 |
| 35 | H | 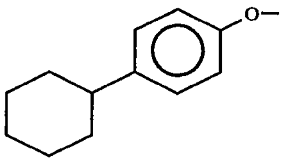 | H | H | —Me | —CONMe— | 2 |

TABLE 1-continued
| | | | | | | | |
|---|---|---|---|---|---|---|---|
| 36 | H | 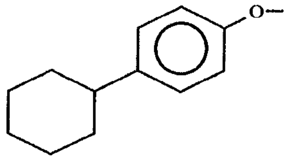 | H | H | —Me | —CONH— | 2 |
| 37 | H | 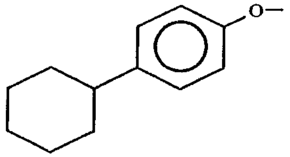 | H | H | —Me | —CONH— | 1 |
| 38 | H | 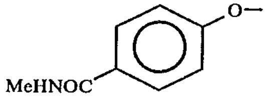 | H | H | —Me | —CONH— | 2 |
| 39 | —Me | 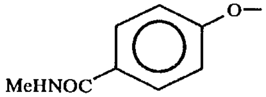 | H | H | —Me | —CONH— | 2 |
| 40 | H | 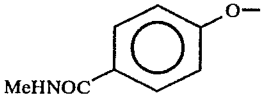 | H | H | —Me | —CONH— | 1 |
| 41 | H | 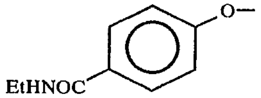 | H | H | —Me | —CONH— | 2 |
| 42 | H | 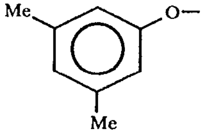 | H | H | —Me | —CONH— | 2 |

TABLE 1-continued
| | | | | | | | |
|---|---|---|---|---|---|---|---|
| 43 | H | 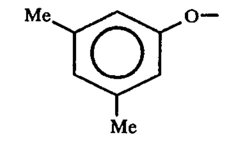 | H | H | —Me | —CONH— | 1 |
| 44 | —OH | 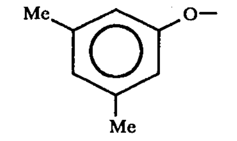 | H | H | —Me | —CONH— | 2 |
| 45 | H | 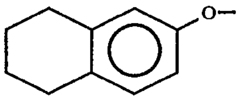 | H | H | —Me | —CONH— | 2 |
| 46 | H | 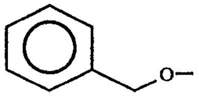 | H | H | —Me | —CONH— | 2 |
| 47 | —Me | 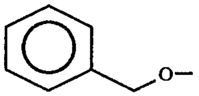 | H | H | —Me | —CONH— | 2 |
| 48 | —OH | 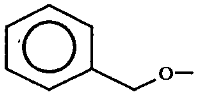 | H | H | —Me | —CONH— | 2 |
| 49 | H | 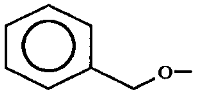 | H | H | —Me | —CONH— | 1 |

TABLE 1-continued
| | | | | | | | |
|---|---|---|---|---|---|---|---|
| 50 | H | 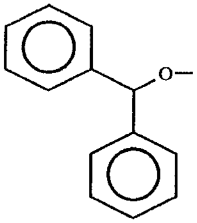 | H | H | —Me | —CONH— | 2 |
| 51 | H | 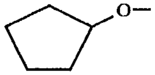 | H | H | —Me | —CONH— | 2 |
| 52 | H | 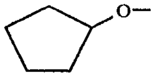 | Me— | H | —Me | —CONH— | 2 |
| 53 | H | 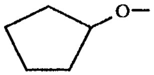 | Et— | H | —Me | —CONH— | 2 |
| 54 | H | 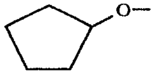 | iPr— | H | —Me | —CONH— | 2 |
| 55 | H | 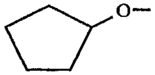 | Me—O— | H | —Me | —CONH— | 2 |
| 56 | H | 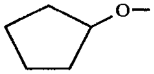 | Et—O— | H | —Me | —CONH— | 2 |
| 57 | H | 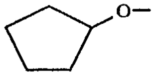 | iPr— | H | —Me | —CONH— | 2 |
| 58 | —OH | 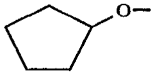 | H | H | —Me | —CONH— | 2 |

TABLE 1-continued
| | | | | | | | |
|---|---|---|---|---|---|---|---|
| 59 | —F | 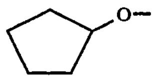 | H | H | —Me | —CONH— | 2 |
| 60 | —Cl | 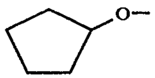 | H | H | —Me | —CONH— | 2 |
| 61 | —Br | 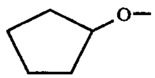 | H | H | —Me | —CONH— | 2 |
| 62 | H | 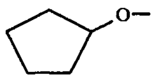 | H | H | —Me | —CONH— | 1 |
| 63 | H | 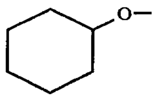 | H | H | —Me | —CONH— | 2 |
| 64 | H | 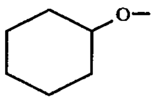 | Me— | H | —Me | —CONH— | 2 |
| 65 | H | 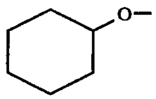 | Et— | H | —Me | —CONH— | 2 |
| 66 | H | 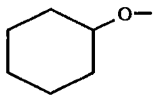 | iPr— | H | —Me | —CONH— | 2 |
| 67 | H | 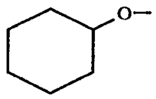 | Me—O— | H | —Me | —CONH— | 2 |

TABLE 1-continued
| | | | | | | | |
|---|---|---|---|---|---|---|---|
| 68 | H | 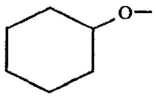 | Et—O— | H | —Me | —CONH— | 2 |
| 69 | H | 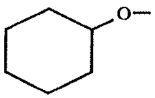 | iPr—O— | H | —Me | —CONH— | 2 |
| 70 | —OH | 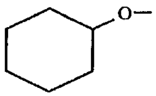 | H | H | —Me | —CONH— | 2 |
| 71 | —Me | 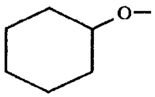 | H | H | —Me | —CONH— | 2 |
| 72 | —F | 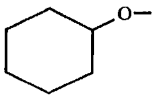 | H | H | —Me | —CONH— | 2 |
| 73 | —Cl | 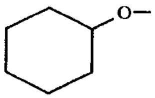 | H | H | —Me | —CONH— | 2 |
| 74 | —Br | 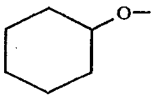 | H | H | —Me | —CONH— | 2 |
| 75 | H | 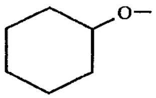 | H | F— | —Me | —CONH— | 2 |
| 76 | H | 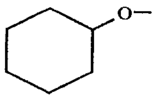 | H | Cl— | —Me | —CONH— | 2 |

TABLE 1-continued
| | | | | | | | |
|---|---|---|---|---|---|---|---|
| 77 | H | 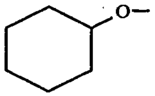 | H | Br— | —Me | —CONH— | 2 |
| 78 | H | 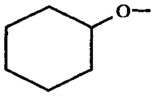 | H | 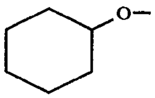 | —Me | —CONH— | 2 |
| 79 | H | 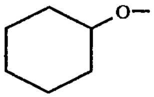 | H | H | —Me | —CONMe— | 2 |
| 80 | H | 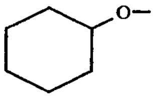 | Me— | H | —Me | —CONMe— | 2 |
| 81 | H | 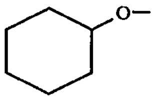 | Et— | H | —Me | —CONMe— | 2 |
| 82 | H | 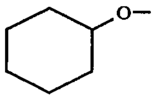 | iPr— | H | —Me | —CONMe— | 2 |
| 83 | H | 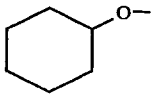 | Me—O— | H | —Me | —CONMe— | 2 |
| 84 | H | 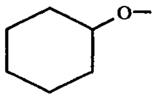 | Et—O— | H | —Me | —CONMe— | 2 |

TABLE 1-continued
| | | | | | | | |
|---|---|---|---|---|---|---|---|
| 85 | H | 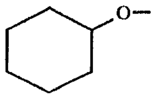 | iPr—O— | H | —Me | —CONMe— | 2 |
| 86 | —OH | 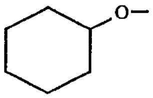 | H | H | —Me | —CONMe— | 2 |
| 87 | H | 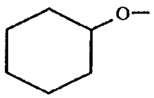 | H | H | —Me | —CONH— | 1 |
| 88 | H | 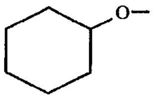 | Me— | H | —Me | —CONH— | 1 |
| 89 | H | 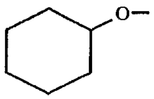 | Et— | H | —Me | —CONH— | 1 |
| 90 | H | 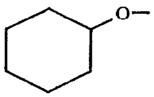 | iPr— | H | —Me | —CONH— | 1 |
| 91 | H | 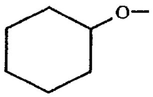 | Me—O— | H | —Me | —CONH— | 1 |
| 92 | H | 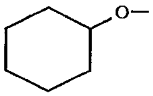 | Et—O— | H | —Me | —CONH— | 1 |
| 93 | H | 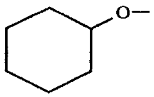 | iPr—O— | H | —Me | —CONH— | 1 |

TABLE 1-continued
| | | | | | | | |
|---|---|---|---|---|---|---|---|
| 94 | —OH | 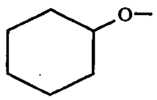 | H | H | —Me | —CONH— | 1 |
| 95 | —Me | 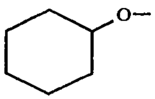 | H | H | —Me | —CONH— | 1 |
| 96 | —F | 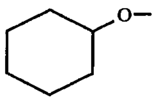 | H | H | —Me | —CONH— | 1 |
| 97 | —Cl | 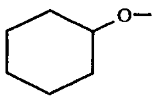 | H | H | —Me | —CONH— | 1 |
| 98 | —Br | 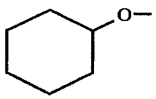 | H | H | —Me | —CONH— | 1 |
| 99 | H | 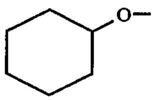 | H | F— | —Me | —CONH— | 1 |
| 100 | H | 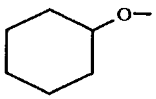 | H | Cl— | —Me | —CONH— | 1 |
| 101 | H | 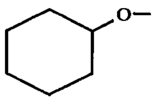 | H | Br— | —Me | —CONH— | 1 |

TABLE 1-continued
| | | | | | | | |
|---|---|---|---|---|---|---|---|
| 102 | H | 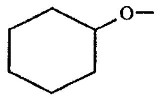 | H | 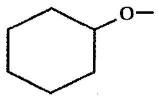 | —Me | —CONH— | 1 |
| 103 | H | 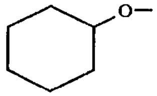 | H | H | —Me | —CONMe— | 1 |
| 104 | H | 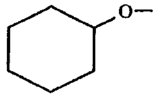 | Me— | H | —Me | —CONMe— | 1 |
| 105 | H | 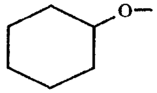 | Et— | H | —Me | —CONMe— | 1 |
| 106 | H | 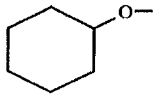 | iPr— | H | —Me | —CONMe— | 1 |
| 107 | H | 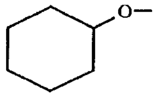 | Me—O— | H | —Me | —CONMe— | 1 |
| 108 | H | 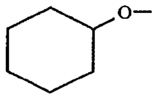 | Et—O— | H | —Me | —CONMe— | 1 |
| 109 | H | 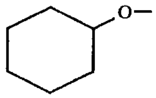 | iPr—O— | H | —Me | —CONMe— | 1 |
| 110 | —OH | 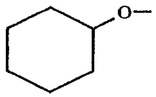 | H | H | —Me | —CONMe— | 1 |

TABLE 1-continued
| | | | | | | | |
|---|---|---|---|---|---|---|---|
| 111 | H | 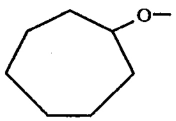 | H | H | —Me | —CONH— | 2 |
| 112 | H | 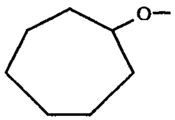 | Me— | H | —Me | —CONH— | 2 |
| 113 | H | 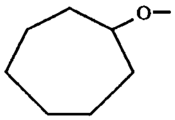 | Et— | H | —Me | —CONH— | 2 |
| 114 | H | 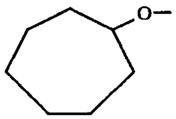 | iPr— | H | —Me | —CONH— | 2 |
| 115 | H | 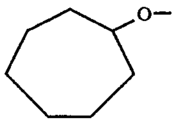 | Me—O— | H | —Me | —CONH— | 2 |
| 116 | H | 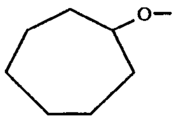 | Et—O— | H | —Me | —CONH— | 2 |
| 117 | H | 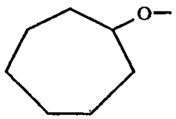 | iPr—O— | H | —Me | —CONH— | 2 |

TABLE 1-continued
| | | | | | | | |
|---|---|---|---|---|---|---|---|
| 118 | —OH | 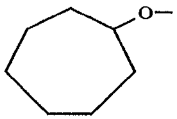 | H | H | —Me | —CONH— | 2 |
| 119 | —Me | 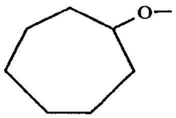 | H | H | —Me | —CONH— | 2 |
| 120 | —F | 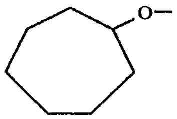 | H | H | —Me | —CONH— | 2 |
| 121 | —Cl | 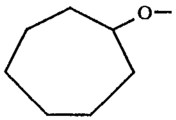 | H | H | —Me | —CONH— | 2 |
| 122 | —Br | 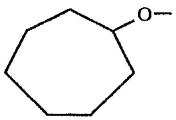 | H | H | —Me | —CONH— | 2 |
| 123 | H | 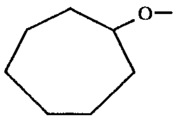 | H | F— | —Me | —CONH— | 2 |
| 124 | H | 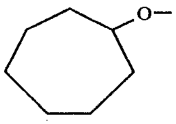 | H | Cl— | —Me | —CONH— | 2 |

TABLE 1-continued
| | | | | | | | |
|---|---|---|---|---|---|---|---|
| 125 | H | 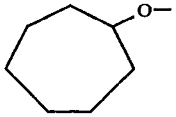 | H | Br— | —Me | —CONH— | 2 |
| 126 | H | 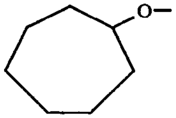 | H | 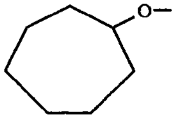 | —Me | —CONH— | 2 |
| 127 | H | 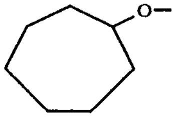 | H | H | —Me | —CONMe— | 2 |
| 128 | H | 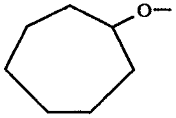 | Me— | H | —Me | —CONMe— | 2 |
| 129 | H | 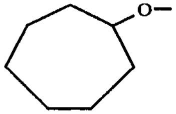 | Et— | H | —Me | —CONMe— | 2 |
| 130 | H | 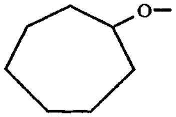 | iPr— | H | —Me | —CONMe— | 2 |
| 131 | H | 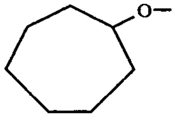 | Me—O— | H | —Me | —CONMe— | 2 |

TABLE 1-continued
| | | | | | | | |
|---|---|---|---|---|---|---|---|
| 132 | H | 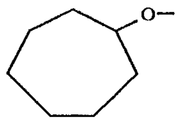 | Et—O— | H | —Me | —CONMe— | 2 |
| 133 | H | 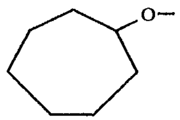 | iPr—O— | H | —Me | —CONMe— | 2 |
| 134 | —OH | 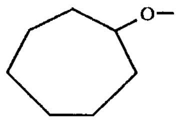 | H | H | —Me | —CONMe— | 2 |
| 135 | H | 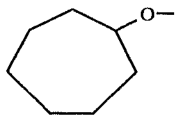 | H | H | —Me | —CONH— | 1 |
| 136 | H | 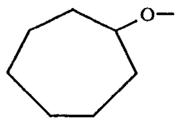 | Me— | H | —Me | —CONH— | 1 |
| 137 | H | 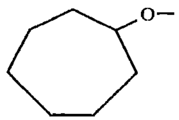 | Et— | H | —Me | —CONH— | 1 |
| 138 | H | 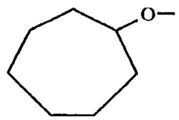 | iPr— | H | —Me | —CONH— | 1 |

TABLE 1-continued
| | | | | | | | |
|---|---|---|---|---|---|---|---|
| 139 | H | 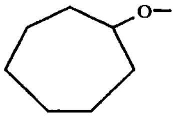 | Me—O— | H | —Me | —CONH— | 1 |
| 140 | H | 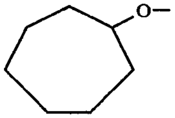 | Et—O— | H | —Me | —CONH— | 1 |
| 141 | H | 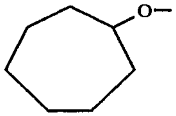 | iPr—O— | H | —Me | —CONH— | 1 |
| 142 | —OH | 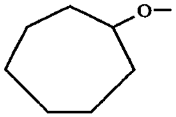 | H | H | —Me | —CONH— | 1 |
| 143 | —Me | 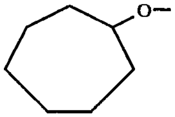 | H | H | —Me | —CONH— | 1 |
| 144 | —F | 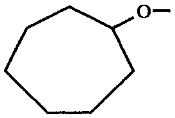 | H | H | —Me | —CONH— | 1 |
| 145 | —Cl | 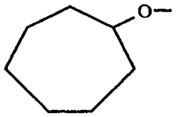 | H | H | —Me | —CONH— | 1 |

TABLE 1-continued
| | | | | | | | |
|---|---|---|---|---|---|---|---|
| 146 | —Br | 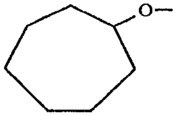 | H | H | —Me | —CONH— | 1 |
| 147 | H | 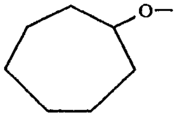 | H | F— | —Me | —CONH— | 1 |
| 148 | H | 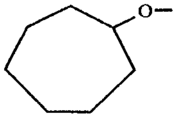 | H | Cl— | —Me | —CONH— | 1 |
| 149 | H | 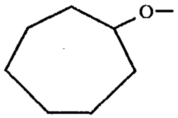 | H | Br— | —Me | —CONH— | 1 |
| 150 | H | 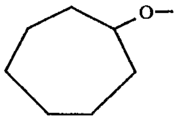 | H | 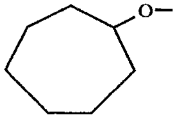 | —Me | —CONH— | 1 |
| 151 | H | 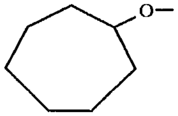 | H | H | —Me | —CONMe— | 1 |
| 152 | H | 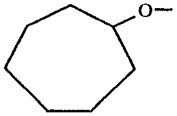 | Me— | H | —Me | —CONMe— | 1 |

TABLE 1-continued
| | | | | | | | |
|---|---|---|---|---|---|---|---|
| 153 | H | 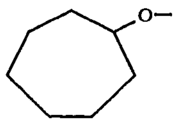 | Et— | H | —Me | —CONMe— | 1 |
| 154 | H | 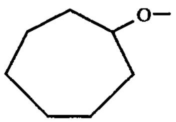 | iPr— | H | —Me | —CONMe— | 1 |
| 155 | H | 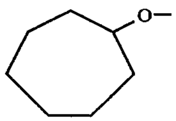 | Me—O— | H | —Me | —CONMe— | 1 |
| 156 | H | 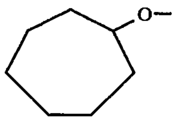 | Et—O— | H | —Me | —CONMe— | 1 |
| 157 | H | 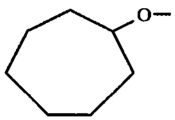 | iPr—O— | H | —Me | —CONMe— | 1 |
| 158 | —OH | 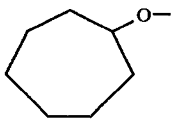 | H | H | —Me | —CONMe— | 1 |
| 159 | H | 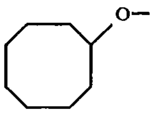 | H | H | —Me | —CONH— | 2 |

TABLE 1-continued
| | | | | | | | |
|---|---|---|---|---|---|---|---|
| 160 | H | 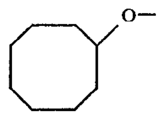 | Me— | H | —Me | —CONH— | 2 |
| 161 | H | 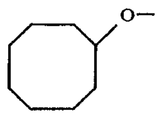 | Et— | H | —Me | —CONH— | 2 |
| 162 | H | 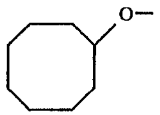 | iPr— | H | —Me | —CONH— | 2 |
| 163 | H | 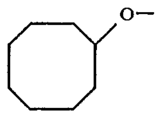 | Me—O— | H | —Me | —CONH— | 2 |
| 164 | H | 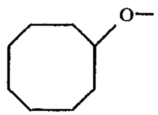 | Et—O— | H | —Me | —CONH— | 2 |
| 165 | H | 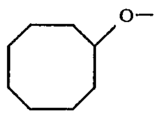 | iPr—O— | H | —Me | —CONH— | 2 |
| 166 | —OH | 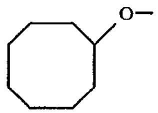 | H | H | —Me | —CONH— | 2 |
| 167 | —Me | 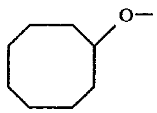 | H | H | —Me | —CONH— | 2 |

TABLE 1-continued
| | | | | | | | |
|---|---|---|---|---|---|---|---|
| 168 | —F | 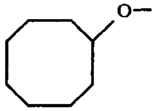 | H | H | —Me | —CONH— | 2 |
| 169 | —Cl | 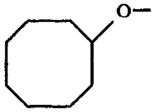 | H | H | —Me | —CONH— | 2 |
| 170 | —Br | 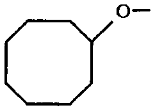 | H | H | —Me | —CONH— | 2 |
| 171 | H | 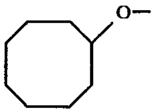 | H | F— | —Me | —CONH— | 2 |
| 172 | H | 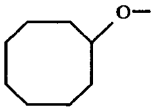 | H | Cl— | —Me | —CONH— | 2 |
| 173 | H | 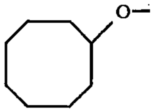 | H | Br— | —Me | —CONH— | 2 |
| 174 | H | 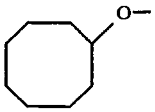 | H | 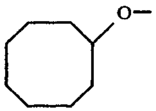 | —Me | —CONH— | 2 |
| 175 | H | 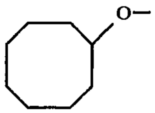 | H | H | —Me | —CONMe— | 2 |

TABLE 1-continued
| | | | | | | | |
|---|---|---|---|---|---|---|---|
| 176 | H | 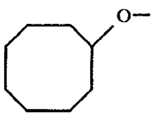 | Me— | H | —Me | —CONMe— | 2 |
| 177 | H | 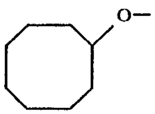 | Et— | H | —Me | —CONMe— | 2 |
| 178 | H | 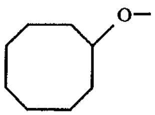 | iPr— | H | —Me | —CONMe— | 2 |
| 179 | H | 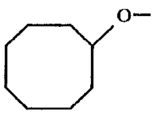 | Me—O— | H | —Me | —CONMe— | 2 |
| 180 | H | 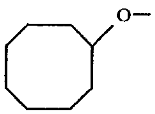 | Et—O— | H | —Me | —CONMe— | 2 |
| 181 | H | 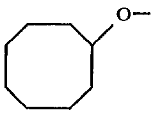 | iPr—O— | H | —Me | —CONMe— | 2 |
| 182 | —OH | 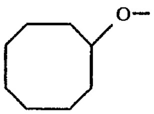 | H | H | —Me | —CONMe— | 2 |
| 183 | H | 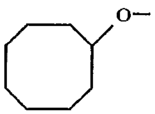 | H | H | —Me | —CONH— | 1 |

TABLE 1-continued
| | | | | | | | |
|---|---|---|---|---|---|---|---|
| 184 | H | 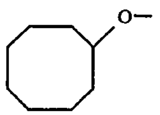 | Me— | H | —Me | —CONH— | 1 |
| 185 | H | 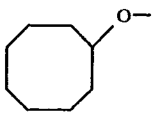 | Et— | H | —Me | —CONH— | 1 |
| 186 | H | 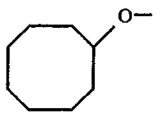 | iPr— | H | —Me | —CONH— | 1 |
| 187 | H | 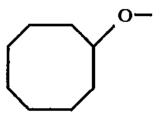 | Me—O— | H | —Me | —CONH— | 1 |
| 188 | H | 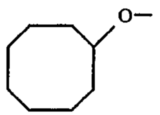 | Et—O— | H | —Me | —CONH— | 1 |
| 189 | H | 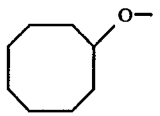 | iPr—O— | H | —Me | —CONH— | 1 |
| 190 | —OH | 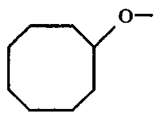 | H | H | —Me | —CONH— | 1 |
| 191 | —Me | 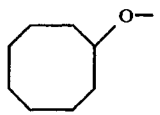 | H | H | —Me | —CONH— | 1 |

TABLE 1-continued
| | | | | | | | |
|---|---|---|---|---|---|---|---|
| 192 | —F | 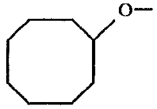 | H | H | —Me | —CONH— | 1 |
| 193 | —Cl | 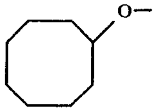 | H | H | —Me | —CONH— | 1 |
| 194 | —Br | 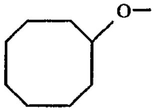 | H | H | —Me | —CONH— | 1 |
| 195 | H | 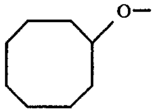 | H | F— | —Me | —CONH— | 1 |
| 196 | H | 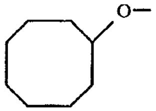 | H | Cl— | —Me | —CONH— | 1 |
| 197 | H | 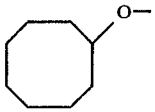 | H | Br— | —Me | —CONH— | 1 |
| 198 | H | 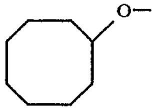 | H | 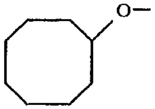 | —Me | —CONH— | 1 |
| 199 | H | 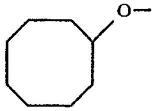 | H | H | —Me | —CONMe— | 1 |

TABLE 1-continued
| | | | | | | | |
|---|---|---|---|---|---|---|---|
| 200 | H | 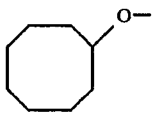 | Me— | H | —Me | —CONMe— | 1 |
| 201 | H | 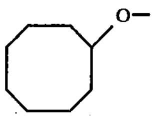 | Et— | H | —Me | —CONMe— | 1 |
| 202 | H | 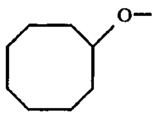 | iPr— | H | —Me | —CONMe— | 1 |
| 203 | H | 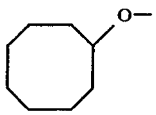 | Me—O— | H | —Me | —CONMe— | 1 |
| 204 | H | 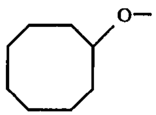 | Et—O— | H | —Me | —CONMe— | 1 |
| 205 | H | 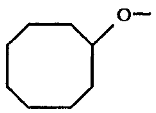 | iPr—O— | H | —Me | —CONMe— | 1 |
| 206 | —OH | 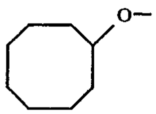 | H | H | —Me | —CONMe— | 1 |
| 207 | H | 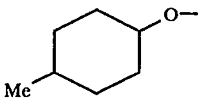 | H | H | —Me | —CONH— | 2 |

TABLE 1-continued
| | | | | | | | |
|---|---|---|---|---|---|---|---|
| 208 | H | 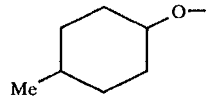 | Me— | H | —Me | —CONH— | 2 |
| 209 | H | 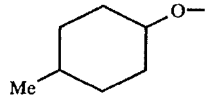 | Et— | H | —Me | —CONH— | 2 |
| 210 | H | 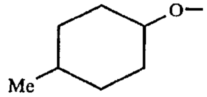 | iPr— | H | —Me | —CONH— | 2 |
| 211 | H | 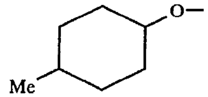 | Me—O— | H | —Me | —CONH— | 2 |
| 212 | H | 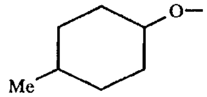 | Et—O— | H | —Me | —CONH— | 2 |
| 213 | H | 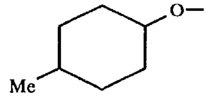 | iPr—O— | H | —Me | —CONH— | 2 |
| 214 | —OH | 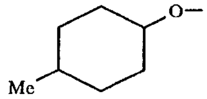 | H | H | —Me | —CONH— | 2 |
| 215 | —Me | 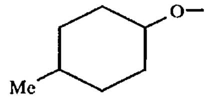 | H | H | —Me | —CONH— | 2 |
| 216 | —F | 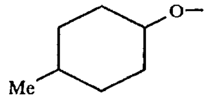 | H | H | —Me | —CONH— | 2 |

TABLE 1-continued
| | | | | | | | |
|---|---|---|---|---|---|---|---|
| 217 | —Cl | 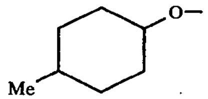 | H | H | —Me | —CONH— | 2 |
| 218 | —Br | 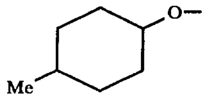 | H | H | —Me | —CONH— | 2 |
| 219 | H | 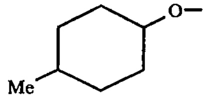 | H | F— | —Me | —CONH— | 2 |
| 220 | H | 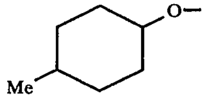 | H | Cl— | —Me | —CONH— | 2 |
| 221 | H | 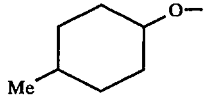 | H | Br— | —Me | —CONH— | 2 |
| 222 | H | 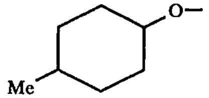 | H | 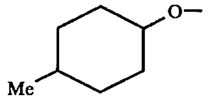 | —Me | —CONH— | 2 |
| 223 | H | 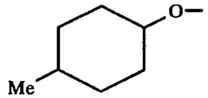 | H | H | —Me | —CONMe— | 2 |
| 224 | H | 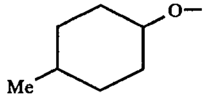 | Me— | H | —Me | —CONMe— | 2 |

| | | | | | | | |
|---|---|---|---|---|---|---|---|
| 225 | H | 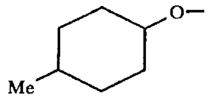 | Et— | H | —Me | —CONMe— | 2 |
| 226 | H | 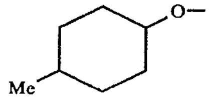 | iPr— | H | —Me | —CONMe— | 2 |
| 227 | H | 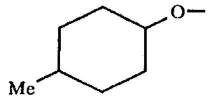 | Me—O— | H | —Me | —CONMe— | 2 |
| 228 | H | 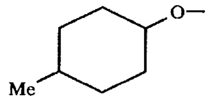 | Et—O— | H | —Me | —CONMe— | 2 |
| 229 | H | 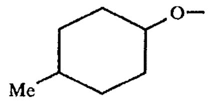 | iPr—O— | H | —Me | —CONMe— | 2 |
| 230 | —OH | 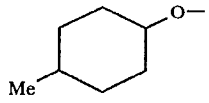 | H | H | —Me | —CONMe— | 2 |
| 231 | H | 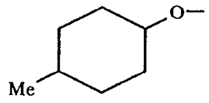 | H | H | —Me | —CONH— | 1 |
| 232 | H | 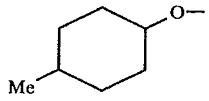 | Me— | H | —Me | —CONH— | 1 |
| 233 | H | 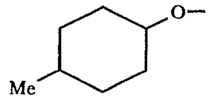 | Et— | H | —Me | —CONH— | 1 |

-continued
| | | | | | | | |
|---|---|---|---|---|---|---|---|
| 234 | H | 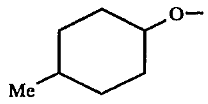 | iPr— | H | —Me | —CONH— | 1 |
| 235 | H | 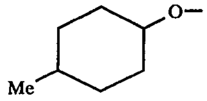 | Me—O— | H | —Me | —CONH— | 1 |
| 236 | H | 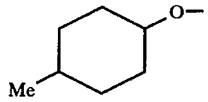 | Et—O— | H | —Me | —CONH— | 1 |
| 237 | H | 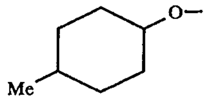 | iPr—O— | H | —Me | —CONH— | 1 |
| 238 | —OH | 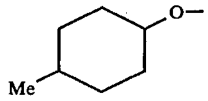 | H | H | —Me | —CONH— | 1 |
| 239 | —Me | 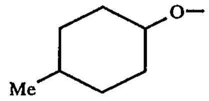 | H | H | —Me | —CONH— | 1 |
| 240 | —F | 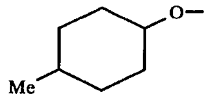 | H | H | —Me | —CONH— | 1 |
| 241 | —Cl | 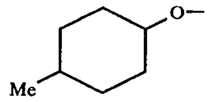 | H | H | —Me | —CONH— | 1 |

-continued
| | | | | | | | |
|---|---|---|---|---|---|---|---|
| 242 | —Br | 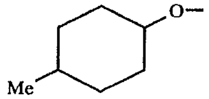 | H | H | —Me | —CONH— | 1 |
| 243 | H | 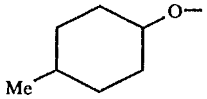 | H | F— | —Me | —CONH— | 1 |
| 244 | H | 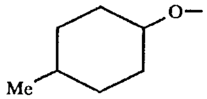 | H | Cl— | —Me | —CONH— | 1 |
| 245 | H | 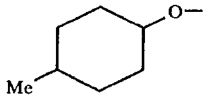 | H | Br— | —Me | —CONH— | 1 |
| 246 | H | 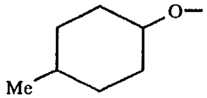 | H | 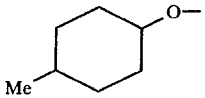 | —Me | —CONH— | 1 |
| 247 | H | 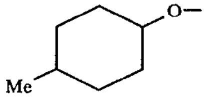 | H | H | —Me | —CONMe— | 1 |
| 248 | H | 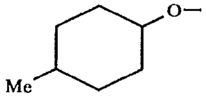 | Me— | H | —Me | —CONMe— | 1 |
| 249 | H | 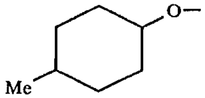 | Et— | H | —Me | —CONMe— | 1 |
| 250 | H | 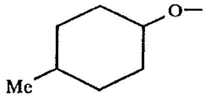 | iPr— | H | —Me | —CONMe— | 1 |

-continued
| | | | | | | | |
|---|---|---|---|---|---|---|---|
| 251 | H | 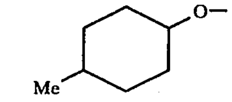 | Me—O— | H | —Me | —CONMe— | 1 |
| 252 | H | 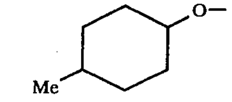 | Et—O— | H | —Me | —CONMe— | 1 |
| 253 | H | 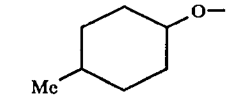 | iPr—O— | H | —Me | —CONMe— | 1 |
| 254 | —OH | 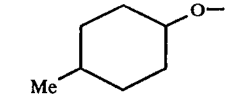 | H | H | —Me | —CONMe— | 1 |
| 255 | H | 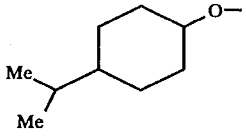 | H | H | —Me | —CONH— | 2 |
| 256 | H | 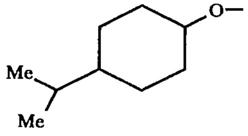 | Me— | H | —Me | —CONH— | 2 |
| 257 | H | 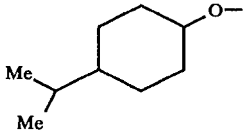 | Et— | H | —Me | —CONH— | 2 |

-continued
| | | | | | | | |
|---|---|---|---|---|---|---|---|
| 258 | H | 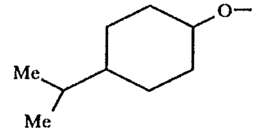 | iPr— | H | —Me | —CONH— | 2 |
| 259 | H | 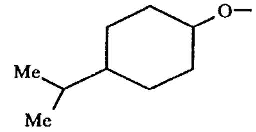 | Me—O— | H | —Me | —CONH— | 2 |
| 260 | H | 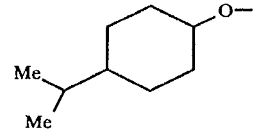 | Et—O— | H | —Me | —CONH— | 2 |
| 261 | H | 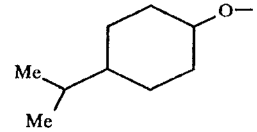 | iPr—O— | H | —Me | —CONH— | 2 |
| 262 | —OH | 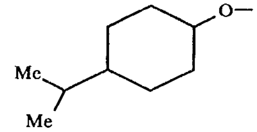 | H | H | —Me | —CONH— | 2 |
| 263 | —Me | 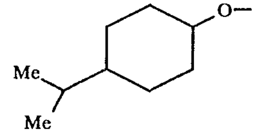 | H | H | —Me | —CONH— | 2 |
| 264 | —F | 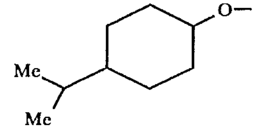 | H— | H | —Me | —CONH— | 2 |

-continued
| | | | | | | | |
|---|---|---|---|---|---|---|---|
| 265 | —Cl | 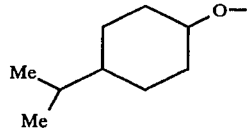 | H | H | —Me | —CONH— | 2 |
| 266 | —Br | 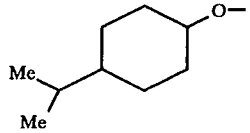 | H | H | —Me | —CONH— | 2 |
| 267 | H | 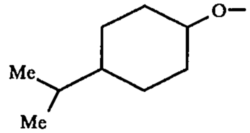 | H | F— | —Me | —CONH— | 2 |
| 268 | H | 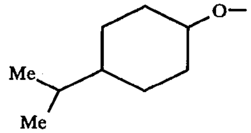 | H | Cl— | —Me | —CONH— | 2 |
| 269 | H | 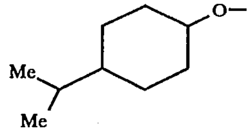 | H | Br— | —Me | —CONH— | 2 |
| 270 | H | 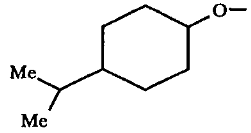 | H | 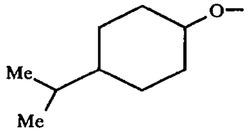 | —Me | —CONH— | 2 |
| 271 | H | 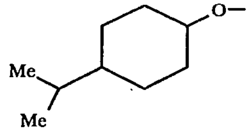 | H | H | —Me | —CONMe— | 2 |

-continued
| | | | | | | | |
|---|---|---|---|---|---|---|---|
| 272 | H | 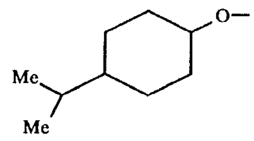 | Me— | H | —Me | —CONMe— | 2 |
| 273 | H | 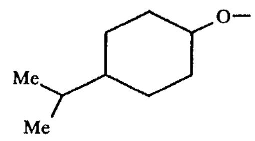 | Et— | H | —Me | —CONMe— | 2 |
| 274 | H | 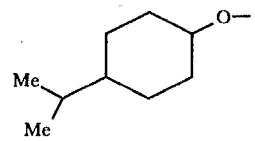 | iPr— | H | —Me | —CONMe— | 2 |
| 275 | H | 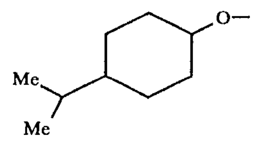 | Me—O— | H | —Me | —CONMe— | 2 |
| 276 | H | 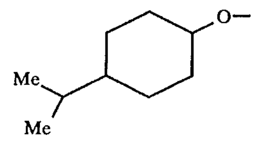 | Et—O— | H | —Me | —CONMe— | 2 |
| 277 | H | 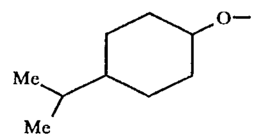 | iPr—O— | H | —Me | —CONMe— | 2 |
| 278 | —OH | 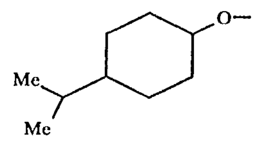 | H | H | —Me | —CONMe— | 2 |

-continued
| | | | | | | | |
|---|---|---|---|---|---|---|---|
| 279 | H | 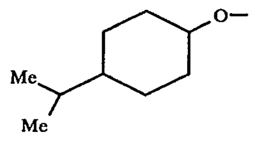 | H | H | —Me | —CONH— | 1 |
| 280 | H | 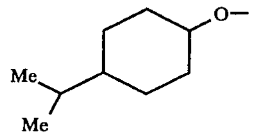 | Me— | H | —Me | —CONH— | 1 |
| 281 | H | 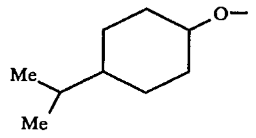 | Et— | H | —Me | —CONH— | 1 |
| 282 | H | 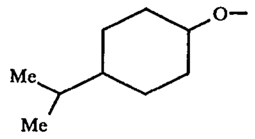 | iPr— | H | —Me | —CONH— | 1 |
| 283 | H | 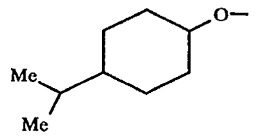 | Me—O— | H | —Me | —CONH— | 1 |
| 284 | H | 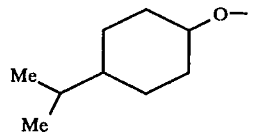 | Et—O— | H | —Me | —CONH— | 1 |
| 285 | H | 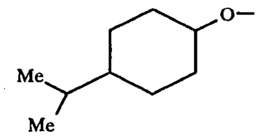 | iPr—O— | H | —Me | —CONH— | 1 |

-continued
| | | | | | | | |
|---|---|---|---|---|---|---|---|
| 286 | —OH | 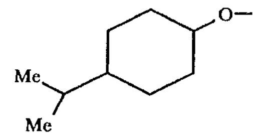 | H | H | —Me | —CONH— | 1 |
| 287 | —Me | 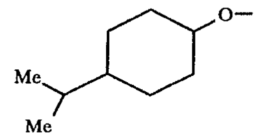 | H | H | —Me | —CONH— | 1 |
| 288 | —F | 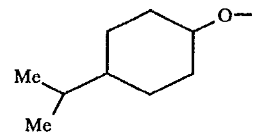 | H | H | —Me | —CONH— | 1 |
| 289 | —Cl | 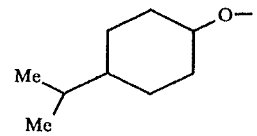 | H | H | —Me | —CONH— | 1 |
| 290 | —Br | 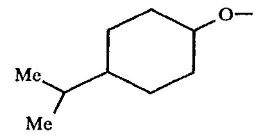 | H | H | —Me | —CONH— | 1 |
| 291 | H | 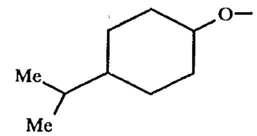 | H | F— | —Me | —CONH— | 1 |
| 292 | H | 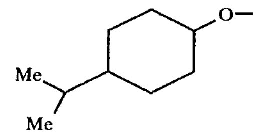 | H | Cl— | —Me | —CONH— | 1 |

-continued
| | | | | | | | |
|---|---|---|---|---|---|---|---|
| 293 | H | 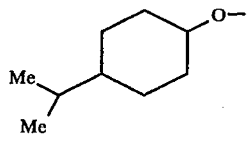 | H | Br— | —Me | —CONH— | 1 |
| 294 | H | 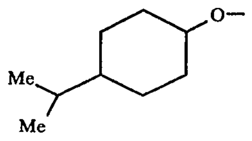 | H | 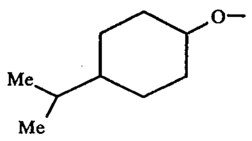 | —Me | —CONH— | 1 |
| 295 | H | 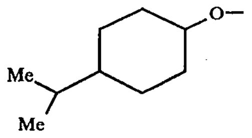 | H | H | —Me | —CONMe— | 1 |
| 296 | H | 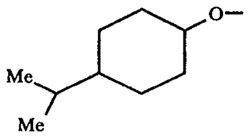 | Me— | H | —Me | —CONMe— | 1 |
| 297 | H | 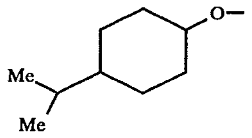 | Et— | H | —Me | —CONMe— | 1 |
| 298 | H | 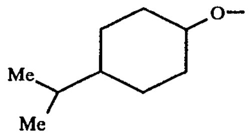 | iPr— | H | —Me | —CONMe— | 1 |
| 299 | H | 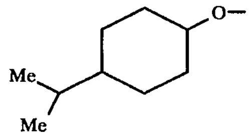 | Me—O— | H | —Me | —CONMe— | 1 |

-continued
| | | | | | | | |
|---|---|---|---|---|---|---|---|
| 300 | H | 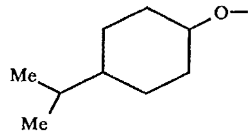 | Et—O— | H | —Me | —CONMe— | 1 |
| 301 | H | 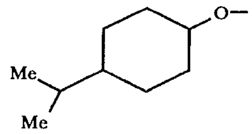 | iPr—O— | H | —Me | —CONMe— | 1 |
| 302 | —OH | 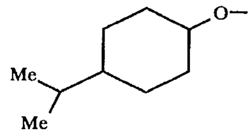 | H | H | —Me | —CONMe— | 1 |
| 303 | H | 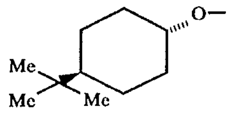 | H | H | —Me | —CONH— | 2 |
| 304 | H | 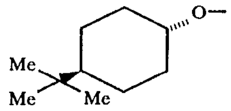 | Me— | H | —Me | —CONH— | 2 |
| 305 | H | 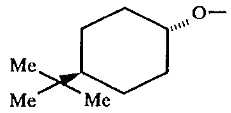 | Et— | H | —Me | —CONH— | 2 |
| 306 | H | 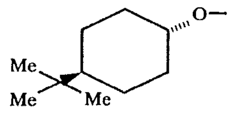 | iPr— | H | —Me | —CONH— | 2 |

-continued
| | | | | | | | |
|---|---|---|---|---|---|---|---|
| 307 | H | 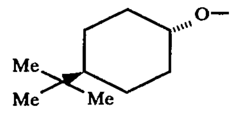 | Me—O— | H | —Me | —CONH— | 2 |
| 308 | H | 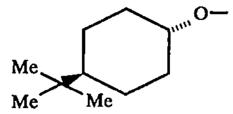 | Et—O— | H | —Me | —CONH— | 2 |
| 309 | H | 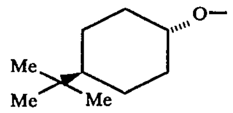 | iPr—O— | H | —Me | —CONH— | 2 |
| 310 | —OH | 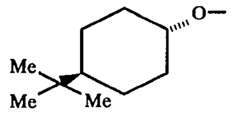 | H | H | —Me | —CONH— | 2 |
| 311 | —Me | 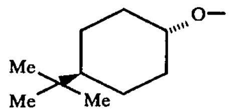 | H | H | —Me | —CONH— | 2 |
| 312 | —F | 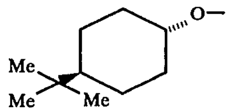 | H | H | —Me | —CONH— | 2 |
| 313 | —Cl | 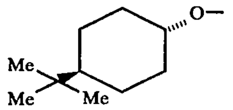 | H | H | —Me | —CONH— | 2 |
| 314 | —Br | 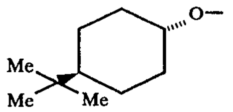 | H | H | —Me | —CONH— | 2 |

-continued
| | | | | | | | |
|---|---|---|---|---|---|---|---|
| 315 | H | 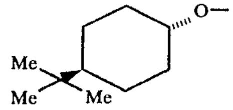 | H | F— | —Me | —CONH— | 2 |
| 316 | H | 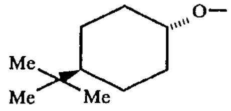 | H | Cl— | —Me | —CONH— | 2 |
| 317 | H | 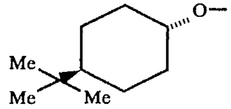 | H | Br— | —Me | —CONH— | 2 |
| 318 | H | 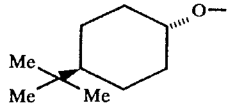 | H | 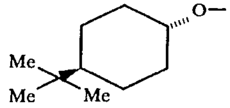 | —Me | —CONH— | 2 |
| 319 | H | 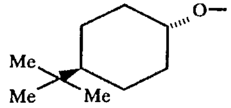 | H | H | —Me | —CONMe— | 2 |
| 320 | H | 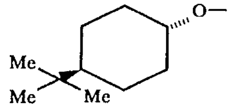 | Me— | H | —Me | —CONMe— | 2 |
| 321 | H | 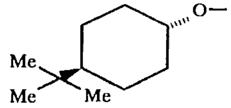 | Et— | H | —Me | —CONMe— | 2 |
| 322 | H | 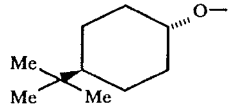 | iPr— | H | —Me | —CONMe— | 2 |

-continued
| | | | | | | | |
|---|---|---|---|---|---|---|---|
| 323 | H | 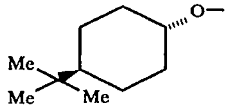 | Me—O— | H | —Me | —CONMe— | 2 |
| 324 | H | 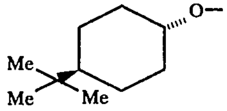 | Et—O— | H | —Me | —CONMe— | 2 |
| 325 | H | 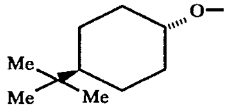 | iPr—O— | H | —Me | —CONMe— | 2 |
| 326 | —OH | 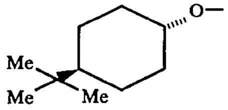 | H | H | —Me | —CONMe— | 2 |
| 327 | H | 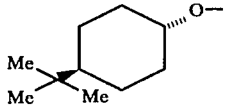 | H | H | —Me | —CONH— | 1 |
| 328 | H | 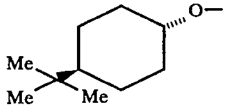 | Me— | H | —Me | —CONH— | 1 |
| 329 | H | 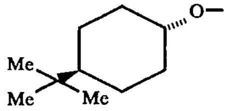 | Et— | H | —Me | —CONH— | 1 |
| 330 | H | 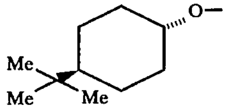 | iPr— | H | —Me | —CONH— | 1 |

-continued
| | | | | | | | |
|---|---|---|---|---|---|---|---|
| 331 | H | 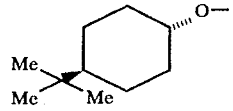 | Me—O— | H | —Me | —CONH— | 1 |
| 332 | H | 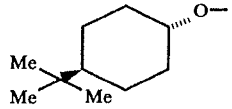 | Et—O— | H | —Me | —CONH— | 1 |
| 333 | H | 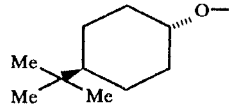 | iPr—O— | H | —Me | —CONH— | 1 |
| 334 | —OH | 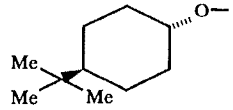 | H | H | —Me | —CONH— | 1 |
| 335 | —Me | 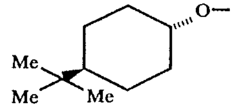 | H | H | —Me | —CONH— | 1 |
| 336 | —F | 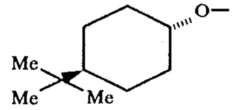 | H | H | —Me | —CONH— | 1 |
| 337 | —Cl | 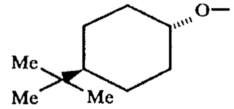 | H | H | —Me | —CONH— | 1 |
| 338 | —Br | 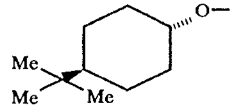 | H | H | —Me | —CONH— | 1 |

-continued
| | | | | | | | |
|---|---|---|---|---|---|---|---|
| 339 | H | 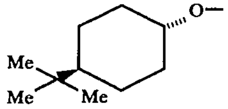 | H | F— | —Me | —CONH— | 1 |
| 340 | H | 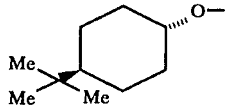 | H | Cl— | —Me | —CONH— | 1 |
| 341 | H | 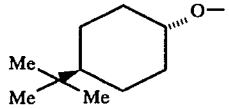 | H | Br— | —Me | —CONH— | 1 |
| 342 | H | 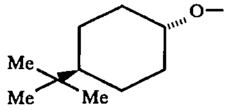 | H | 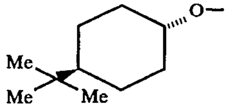 | —Me | —CONH— | 1 |
| 343 | H | 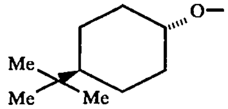 | H | H | —Me | —CONMe— | 1 |
| 344 | H | 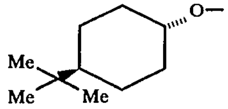 | Me— | H | —Me | —CONMe— | 1 |
| 345 | H | 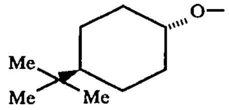 | Et— | H | —Me | —CONMe— | 1 |
| 346 | H | 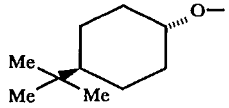 | iPr— | H | —Me | —CONMe— | 1 |

-continued
| | | | | | | | |
|---|---|---|---|---|---|---|---|
| 347 | H | 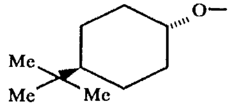 | Me—O— | H | —Me | —CONMe— | 1 |
| 348 | H | 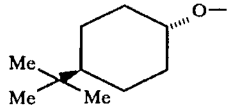 | Et—O— | H | —Me | —CONMe— | 1 |
| 349 | H | 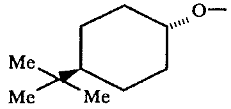 | iPr—O— | H | —Me | —CONMe— | 1 |
| 350 | —OH | 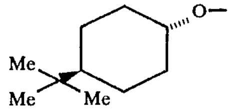 | H | H | —Me | —CONMe— | 1 |
| 351 | H | 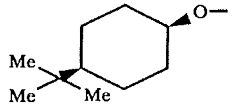 | H | H | —Me | —CONH— | 2 |
| 352 | H | 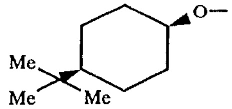 | Me— | H | —Me | —CONH— | 2 |
| 353 | H | 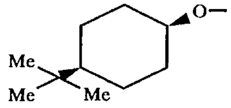 | Et— | H | —Me | —CONH— | 2 |
| 354 | H | 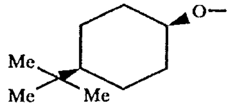 | iPr— | H | —Me | —CONH— | 2 |

-continued
| | | | | | | | |
|---|---|---|---|---|---|---|---|
| 355 | H | 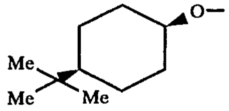 | Me—O— | H | —Me | —CONH— | 2 |
| 356 | H | 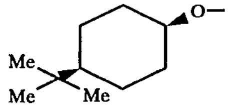 | Et—O— | H | —Me | —CONH— | 2 |
| 357 | H | 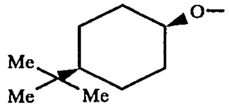 | iPr—O— | H | —Me | —CONH— | 2 |
| 358 | —OH | 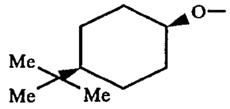 | H | H | —Me | —CONH— | 2 |
| 359 | —Me | 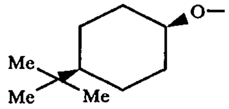 | H | H | —Me | —CONH— | 2 |
| 360 | —F | 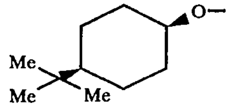 | H | H | —Me | —CONH— | 2 |
| 361 | —Cl | 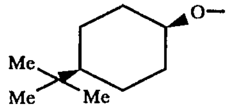 | H | H | —Me | —CONH— | 2 |
| 362 | —Br | 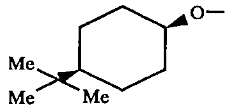 | H | H | —Me | —CONH— | 2 |

-continued
| | | | | | | | |
|---|---|---|---|---|---|---|---|
| 363 | H | 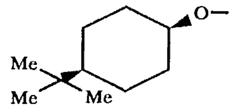 | H | F— | —Me | —CONH— | 2 |
| 364 | H | 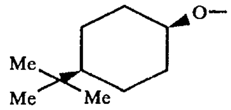 | H | Cl— | —Me | —CONH— | 2 |
| 365 | H | 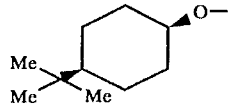 | H | Br— | —Me | —CONH— | 2 |
| 366 | H | 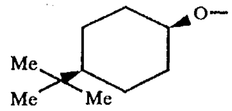 | H | 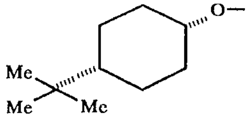 | —Me | —CONH— | 2 |
| 367 | H | 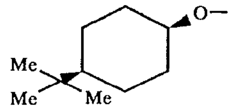 | H | H | —Me | —CONMe— | 2 |
| 368 | H | 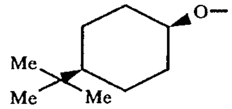 | Me— | H | —Me | —CONMe— | 2 |
| 369 | H | 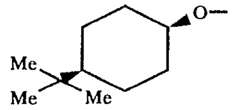 | Et— | H | —Me | —CONMe— | 2 |
| 370 | H | 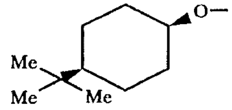 | iPr— | H | —Me | —CONMe— | 2 |

-continued
| | | | | | | | |
|---|---|---|---|---|---|---|---|
| 371 | H | 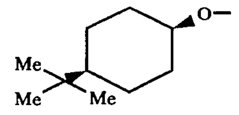 | Me—O— | H | —Me | —CONMe— | 2 |
| 372 | H | 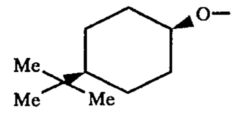 | Et—O— | H | —Me | —CONMe— | 2 |
| 373 | H | 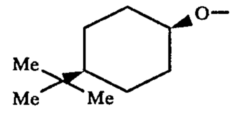 | iPr—O— | H | —Me | —CONMe— | 2 |
| 374 | —OH | 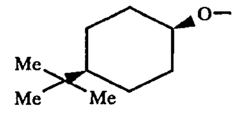 | H | H | —Me | —CONMe— | 2 |
| 375 | H | 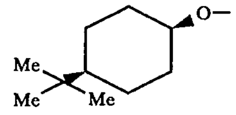 | H | H | —Me | —CONH— | 1 |
| 376 | H | 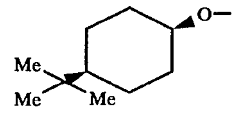 | Me— | H | —Me | —CONH— | 1 |
| 377 | H | 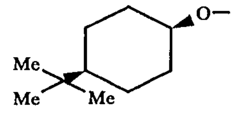 | Et— | H | —Me | —CONH— | 1 |
| 378 | H | 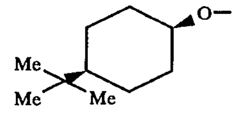 | iPr— | H | —Me | —CONH— | 1 |

-continued
| | | | | | | | |
|---|---|---|---|---|---|---|---|
| 379 | H | 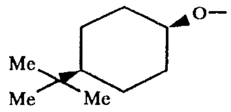 | Me—O— | H | —Me | —CONH— | 1 |
| 380 | H | 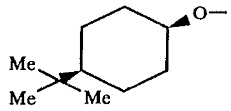 | Et—O— | H | —Me | —CONH— | 1 |
| 381 | H | 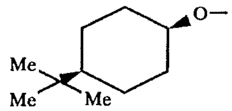 | iPr—O— | H | —Me | —CONH— | 1 |
| 382 | —OH | 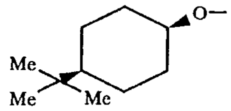 | H | H | —Me | —CONH— | 1 |
| 383 | —Me | 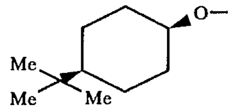 | H | H | —Me | —CONH— | 1 |
| 384 | —F | 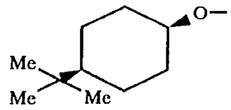 | H | H | —Me | —CONH— | 1 |
| 385 | —Cl | 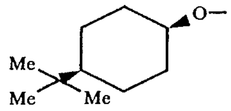 | H | H | —Me | —CONH— | 1 |
| 386 | —Br | 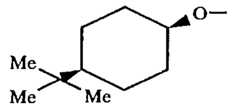 | H | H | —Me | —CONH— | 1 |

-continued
| | | | | | | | |
|---|---|---|---|---|---|---|---|
| 387 | H | 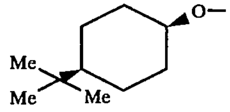 | H | F— | —Me | —CONH— | 1 |
| 388 | H | 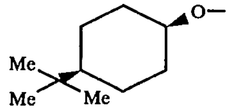 | H | Cl— | —Me | —CONH— | 1 |
| 389 | H | 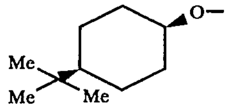 | H | Br— | —Me | —CONH— | 1 |
| 390 | H | 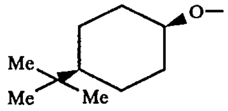 | H | 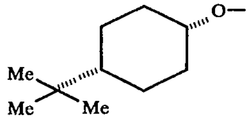 | —Me | —CONH— | 1 |
| 391 | H | 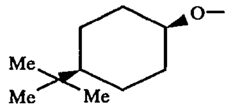 | H | H | —Me | —CONMe— | 1 |
| 392 | H | 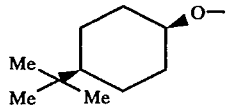 | Me— | H | —Me | —CONMe— | 1 |
| 393 | H | 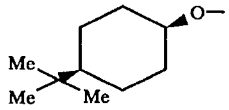 | Et— | H | —Me | —CONMe— | 1 |
| 394 | H | 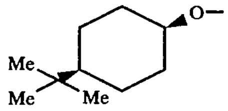 | iPr— | H | —Me | —CONMe— | 1 |

-continued
| | | | | | | | |
|---|---|---|---|---|---|---|---|
| 395 | H | 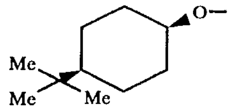 | Me—O— | H | —Me | —CONMe— | 1 |
| 396 | H | 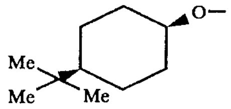 | Et—O— | H | —Me | —CONMe— | 1 |
| 397 | H | 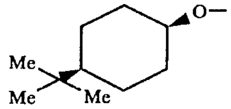 | iPr—O— | H | —Me | —CONMe— | 1 |
| 398 | —OH | 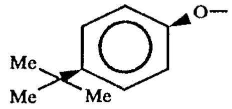 | H | H | —Me | —CONMe— | 1 |
| 399 | H | 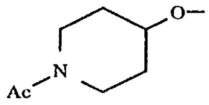 | H | H | —Me | —CONH— | 2 |
| 400 | H | 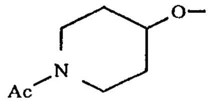 | H | H | —Me | —CONH— | 1 |
| 401 | H | 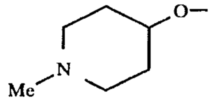 | H | H | —Me | —CONH— | 2 |
| 402 | H | 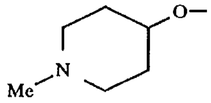 | H | H | —Me | —CONH— | 1 |

-continued
| | | | | | | | |
|---|---|---|---|---|---|---|---|
| 403 | H | 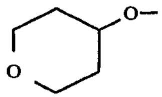 | H | H | —Me | —CONH— | 2 |
| 404 | H | 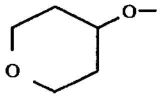 | H | H | —Me | —CONH— | 1 |
| 405 | H | Me— | H | H | —Me | —CONH— | 2 |
| 406 | H | Et— | H | H | —Me | —CONH— | 2 |
| 407 | H | nPr— | H | H | —Me | —CONH— | 2 |
| 408 | H | iPr— | H | H | —Me | —CONH— | 2 |
| 409 | H | Me—O— | H | H | —Me | —CONH— | 2 |
| 410 | H | Et—O— | H | H | —Me | —CONH— | 2 |
| 411 | H | nPr—O— | H | H | —Me | —CONH— | 2 |
| 412 | H | iPr—O— | H | H | —Me | —CONH— | 2 |
| 413 | H | 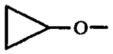 | H | H | —Me | —CONH— | 2 |
| 414 | H | nBu—O— | H | H | —Me | —CONH— | 2 |
| 415 | H | iBu—O— | H | H | —Me | —CONH— | 2 |
| 416 | H | 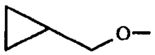 | H | H | —Me | —CONH— | 2 |
| 417 | H | 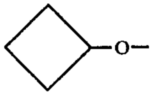 | H | H | —Me | —CONH— | 2 |
| 418 | H | 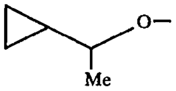 | H | H | —Me | —CONH— | 2 |
| 419 | H | 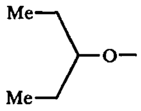 | H | H | —Me | —CONH— | 2 |

-continued
| | | | | | | | |
|---|---|---|---|---|---|---|---|
| 420 | H | 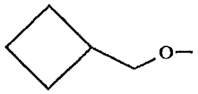 | H | H | —Me | —CONH— | 2 |
| 421 | H | 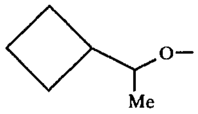 | H | H | —Me | —CONH— | 2 |

| | | | | | | | |
|---|---|---|---|---|---|---|---|
| 422 | H | 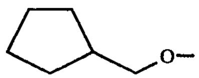 | H | H | —Me | —CONH— | 2 |
| 423 | H | 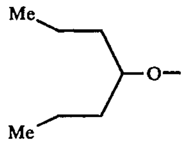 | H | H | —Me | —CONH— | 2 |
| 424 | H | 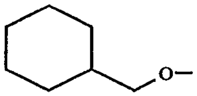 | H | H | —Me | —CONH— | 2 |
| 425 | H | 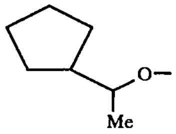 | H | H | —Me | —CONH— | 2 |
| 426 | H | 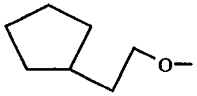 | H | H | —Me | —CONH— | 2 |
| 427 | H | 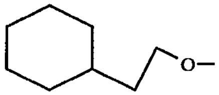 | H | H | —Me | —CONH— | 2 |
| 428 | H | 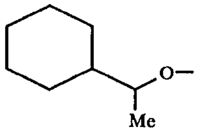 | H | H | —Me | —CONH— | 2 |
| 429 | H | 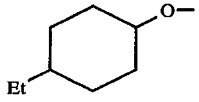 | H | H | —Me | —CONH— | 2 |

-continued
| | | | | | | | |
|---|---|---|---|---|---|---|---|
| 430 | H | 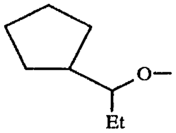 | H | H | —Me | —CONH— | 2 |
| 431 | H | 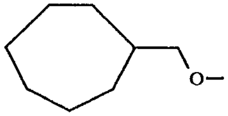 | H | H | —Me | —CONH— | 2 |
| 432 | H | 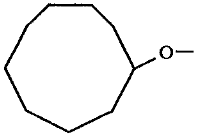 | H | H | —Me | —CONH— | 2 |
| 433 | H | 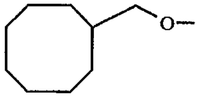 | H | H | —Me | —CONH— | 2 |
| 434 | H | 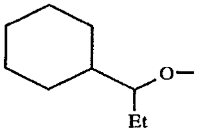 | H | H | —Me | —CONH— | 2 |
| 435 | H | 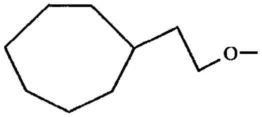 | H | H | —Me | —CONH— | 2 |
| 436 | H | 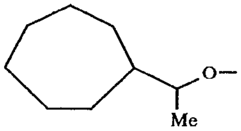 | H | H | —Me | —CONH— | 2 |

-continued
| | | | | | | | |
|---|---|---|---|---|---|---|---|
| 437 | H | 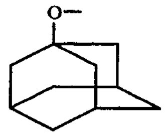 | H | H | —Me | —CONH— | 2 |
| 438 | H | 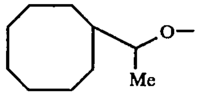 | H | H | —Me | —CONH— | 2 |
| 439 | H | 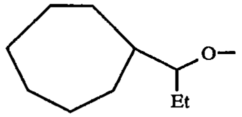 | H | H | —Me | —CONH— | 2 |
| 440 | H | 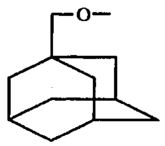 | H | H | —Me | —CONH— | 2 |
| 441 | H | 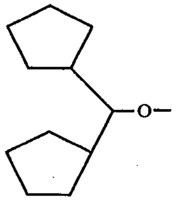 | H | H | —Me | —CONH— | 2 |
| 442 | H | 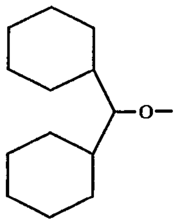 | H | H | —Me | —CONH— | 2 |
| 443 | H | Me— | H | H | —Me | —CONH— | 1 |
| 444 | H | Et— | H | H | —Me | —CONH— | 1 |

-continued
| | | | | | | | |
|---|---|---|---|---|---|---|---|
| 445 | H | nPr— | H | H | —Me | —CONH— | 1 |
| 446 | H | iPr— | H | H | —Me | —CONH— | 1 |
| 447 | H | Me—O— | H | H | —Me | —CONH— | 1 |
| 448 | H | Et—O— | H | H | —Me | —CONH— | 1 |
| 449 | H | nPr—O— | H | H | —Me | —CONH— | 1 |
| 450 | H | iPr—O— | H | H | —Me | —CONH— | 1 |
| 451 | H | 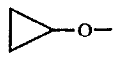 | H | H | —Me | —CONH— | 1 |
| 452 | H | nBu—O— | H | H | —Me | —CONH— | 1 |
| 453 | H | iBu—O— | H | H | —Me | —CONH— | 1 |
| 454 | H | 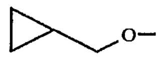 | H | H | —Me | —CONH— | 1 |
| 455 | H | 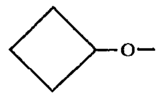 | H | H | —Me | —CONH— | 1 |
| 456 | H | 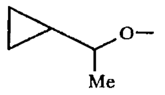 | H | H | —Me | —CONH— | 1 |
| 457 | H | 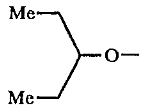 | H | H | —Me | —CONH— | 1 |
| 458 | H | 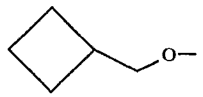 | H | H | —Me | —CONH— | 1 |
| 459 | H | 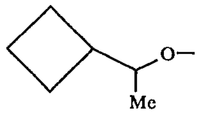 | H | H | —Me | —CONH— | 1 |
| 460 | H | 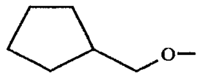 | H | H | —Me | —CONH— | 1 |

-continued
| | | | | | | | |
|---|---|---|---|---|---|---|---|
| 461 | H | 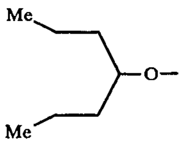 | H | H | —Me | —CONH— | 1 |
| 462 | H | 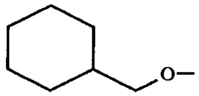 | H | H | —Me | —CONH— | 1 |
| 463 | H | 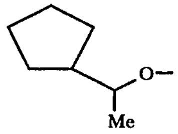 | H | H | —Me | —CONH— | 1 |
| 464 | H | 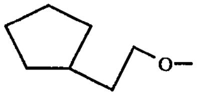 | H | H | —Me | —CONH— | 1 |
| 465 | H | 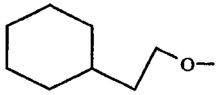 | H | H | —Me | —CONH— | 1 |
| 466 | H | 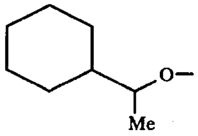 | H | H | —Me | —CONH— | 1 |
| 467 | H | 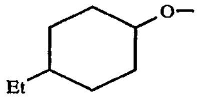 | H | H | —Me | —CONH— | 1 |
| 468 | H | 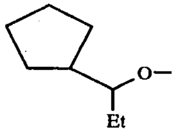 | H | H | —Me | —CONH— | 1 |

-continued
| | | | | | | | |
|---|---|---|---|---|---|---|---|
| 469 | H | 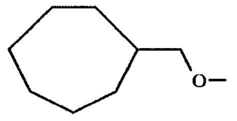 | H | H | —Me | —CONH— | 1 |
| 470 | H | 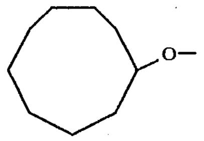 | H | H | —Me | —CONH— | 1 |
| 471 | H | 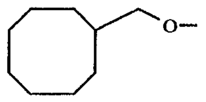 | H | H | —Me | —CONH— | 1 |
| 472 | H | 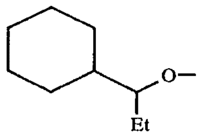 | H | H | —Me | —CONH— | 1 |
| 473 | H | 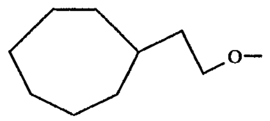 | H | H | —Me | —CONH— | 1 |
| 474 | H | 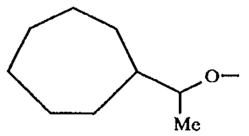 | H | H | —Me | —CONH— | 1 |
| 475 | H | 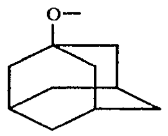 | H | H | —Me | —CONH— | 1 |

-continued
| | | | | | | | |
|---|---|---|---|---|---|---|---|
| 476 | H | 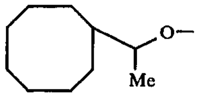 | H | H | —Me | —CONH— | 1 |
| 477 | H | 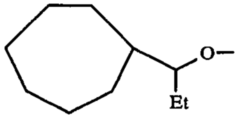 | H | H | —Me | —CONH— | 1 |
| 478 | H | 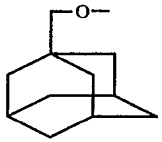 | H | H | —Me | —CONH— | 1 |
| 479 | H | 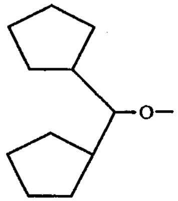 | H | H | —Me | —CONH— | 1 |
| 480 | H | 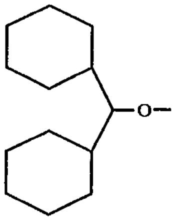 | H | H | —Me | —CONH— | 1 |
| 481 | H | 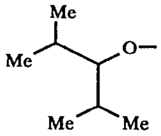 | H | H | —Me | —CONH— | 2 |

-continued
| | | | | | | | |
|---|---|---|---|---|---|---|---|
| 482 | H | 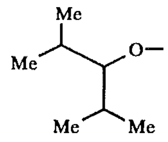 | Me— | H | —Me | —CONH— | 2 |
| 483 | H | 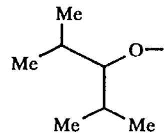 | Et— | H | —Me | —CONH— | 2 |
| 484 | H | 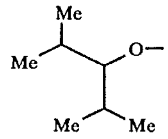 | iPr— | H | —Me | —CONH— | 2 |
| 485 | H | 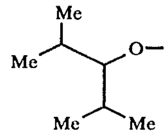 | Me—O— | H | —Me | —CONH— | 2 |
| 486 | H | 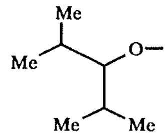 | Et—O— | H | —Me | —CONH— | 2 |
| 487 | H | 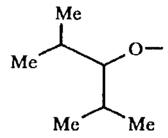 | iPr—O— | H | —Me | —CONH— | 2 |
| 488 | —OH | 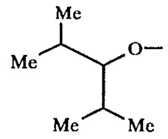 | H | H | —Me | —CONH— | 2 |

-continued
| | | | | | | | |
|---|---|---|---|---|---|---|---|
| 489 | —Me | 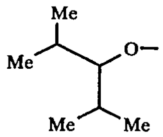 | H | H | —Me | —CONH— | 2 |
| 490 | —F | 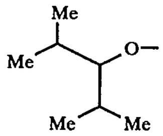 | H | H | —Me | —CONH— | 2 |
| 491 | —Cl | 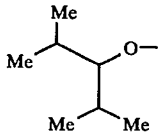 | H | H | —Me | —CONH— | 2 |
| 492 | —Br | 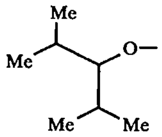 | H | H | —Me | —CONH— | 2 |
| 493 | H | 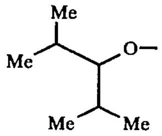 | H | F— | —Me | —CONH— | 2 |
| 494 | H | 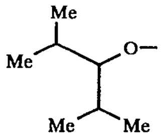 | H | Cl— | —Me | —CONH— | 2 |
| 495 | H | 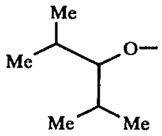 | H | Br— | —Me | —CONH— | 2 |

-continued
| | | | | | | | |
|---|---|---|---|---|---|---|---|
| 496 | H | 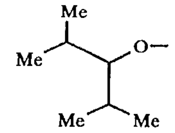 | H | 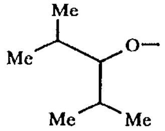 | —Me | —CONH— | 2 |
| 497 | H | 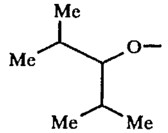 | H | H | —Me | —CONMe— | 2 |
| 498 | H | 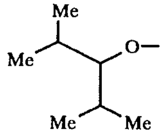 | Me— | H | —Me | —CONMe— | 2 |
| 499 | H | 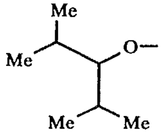 | Et— | H | —Me | —CONMe— | 2 |
| 500 | H | 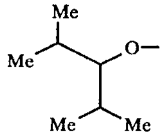 | iPr— | H | —Me | —CONMe— | 2 |
| 501 | H | 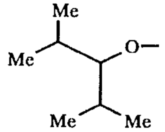 | Me—O— | H | —Me | —CONMe— | 2 |
| 502 | H | 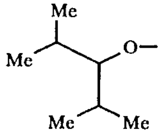 | Et—O— | H | —Me | —CONMe— | 2 |

-continued
| | | | | | | | |
|---|---|---|---|---|---|---|---|
| 503 | H | 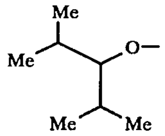 | iPr—O— | H | —Me | —CONMe— | 2 |
| 504 | —OH | 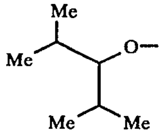 | H | H | —Me | —CONMe— | 2 |
| 505 | H | 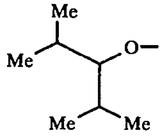 | H | H | —Me | —CONH— | 1 |
| 506 | H | 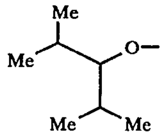 | Me— | H | —Me | —CONH— | 1 |
| 507 | H | 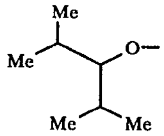 | Et— | H | —Me | —CONH— | 1 |
| 508 | H | 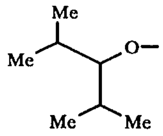 | iPr— | H | —Me | —CONH— | 1 |
| 509 | H | 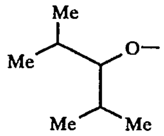 | Me—O— | H | —Me | —CONH— | 1 |

-continued
| | | | | | | | |
|---|---|---|---|---|---|---|---|
| 510 | H | 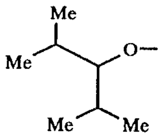 | Et—O— | H | —Me | —CONH— | 1 |
| 511 | H | 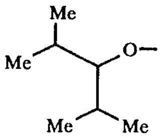 | iPr—O— | H | —Me | —CONH— | 1 |
| 512 | —OH | 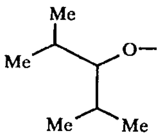 | H | H | —Me | —CONH— | 1 |
| 513 | —Me | 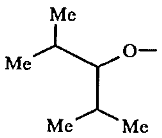 | H | H | —Me | —CONH— | 1 |
| 514 | —F | 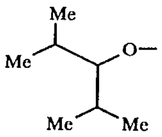 | H | H | —Me | —CONH— | 1 |
| 515 | —Cl | 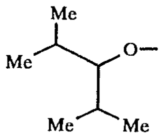 | H | H | —Me | —CONH— | 1 |
| 516 | —Br | 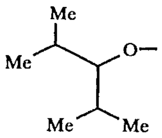 | H | H | —Me | —CONH— | 1 |

-continued
| | | | | | | | |
|---|---|---|---|---|---|---|---|
| 517 | H | 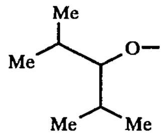 | H | F— | —Me | —CONH— | 1 |
| 518 | H | 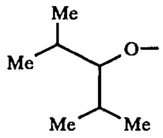 | H | Cl— | —Me | —CONH— | 1 |
| 519 | H | 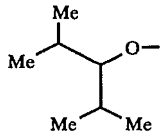 | H | Br— | —Me | —CONH— | 1 |
| 520 | H | 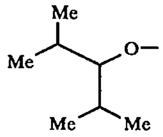 | H | 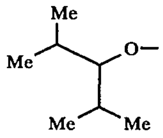 | —Me | —CONH— | 1 |
| 521 | H | 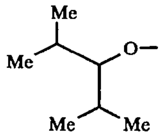 | H | H | —Me | —CONMe— | 1 |
| 522 | H | 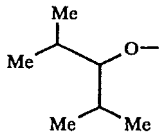 | Me— | H | —Me | —CONMe— | 1 |
| 523 | H | 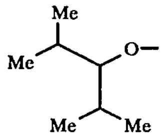 | Et— | H | —Me | —CONMe— | 1 |

-continued
| | | | | | | | |
|---|---|---|---|---|---|---|---|
| 524 | H | 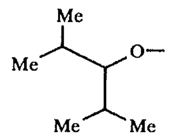 | iPr— | H | —Me | —CONMe— | 1 |
| 525 | H | 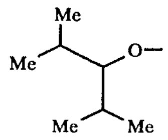 | Me—O— | H | —Me | —CONMe— | 1 |
| 526 | H | 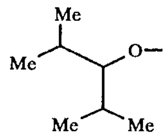 | Et—O— | H | —Me | —CONMe— | 1 |
| 527 | H | 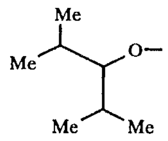 | iPr—O— | H | —Me | —CONMe— | 1 |
| 528 | —OH | 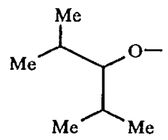 | H | H | —Me | —CONMe— | 1 |
| 529 | H | 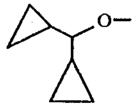 | H | H | —Me | —CONH— | 2 |
| 530 | H | 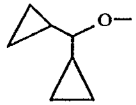 | Me— | H | —Me | —CONH— | 2 |

-continued
| | | | | | | | |
|---|---|---|---|---|---|---|---|
| 531 | H | 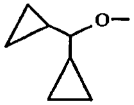 | Et— | H | —Me | —CONH— | 2 |
| 532 | H | 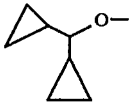 | iPr— | H | —Me | —CONH— | 2 |
| 533 | H | 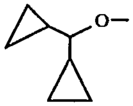 | Me—O— | H | —Me | —CONH— | 2 |
| 534 | H | 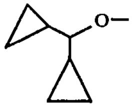 | Et—O— | H | —Me | —CONH— | 2 |
| 535 | H | 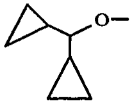 | iPr—O— | H | —Me | —CONH— | 2 |
| 536 | —OH | 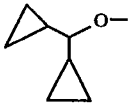 | H | H | —Me | —CONH— | 2 |
| 537 | —Me | 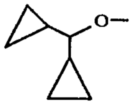 | H | H | —Me | —CONH— | 2 |
| 538 | —F | 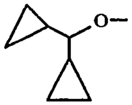 | H | H | —Me | —CONH— | 2 |

-continued
| | | | | | | | |
|---|---|---|---|---|---|---|---|
| 539 | —Cl | 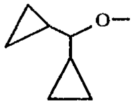 | H | H | —Me | —CONH— | 2 |
| 540 | —Br | 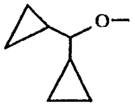 | H | H | —Me | —CONH— | 2 |
| 541 | H | 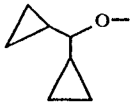 | H | F— | —Me | —CONH— | 2 |
| 542 | H | 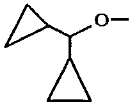 | H | Cl— | —Me | —CONH— | 2 |
| 543 | H | 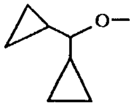 | H | Br— | —Me | —CONH— | 2 |
| 544 | H | 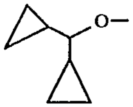 | H | 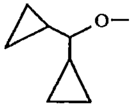 | —Me | —CONH— | 2 |
| 545 | H | 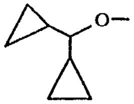 | H | H | —Me | —CONMe— | 2 |
| 546 | H | 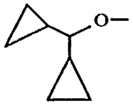 | Me— | H | —Me | —CONMe— | 2 |

-continued
| | | | | | | | |
|---|---|---|---|---|---|---|---|
| 547 | H | 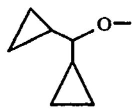 | Et— | H | —Me | —CONMe— | 2 |
| 548 | H | 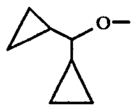 | iPr— | H | —Me | —CONMe— | 2 |
| 549 | H | 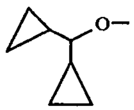 | Me—O— | H | —Me | —CONMe— | 2 |
| 550 | H | 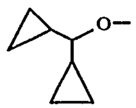 | Et—O— | H | —Me | —CONMe— | 2 |
| 551 | H | 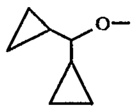 | iPr—O— | H | —Me | —CONMe— | 2 |
| 552 | —OH | 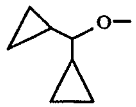 | H | H | —Me | —CONMe— | 2 |
| 553 | H | 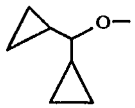 | H | H | —Me | —CONH— | 1 |
| 554 | H | 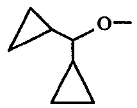 | Me— | H | —Me | —CONH— | 1 |

-continued
| | | | | | | | |
|---|---|---|---|---|---|---|---|
| 555 | H | 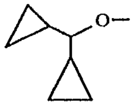 | Et— | H | —Me | —CONH— | 1 |
| 556 | H | 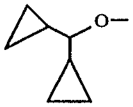 | iPr— | H | —Me | —CONH— | 1 |
| 557 | H | 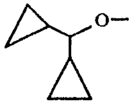 | Me—O— | H | —Me | —CONH— | 1 |
| 558 | H | 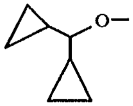 | Et—O— | H | —Me | —CONH— | 1 |
| 559 | H | 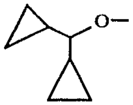 | iPr—O— | H | —Me | —CONH— | 1 |
| 560 | —OH | 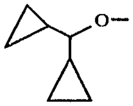 | H | H | —Me | —CONH— | 1 |
| 561 | —Me | 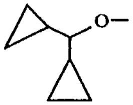 | H | H | —Me | —CONH— | 1 |
| 562 | —F | 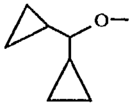 | B | H | —Me | —CONH— | 1 |

-continued
| | | | | | | | |
|---|---|---|---|---|---|---|---|
| 563 | —Cl | 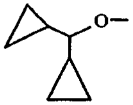 | H | H | —Me | —CONH— | 1 |
| 564 | —Br | 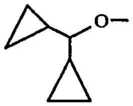 | H | H | —Me | —CONH— | 1 |
| 565 | H | 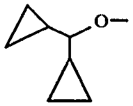 | H | F— | —Me | —CONH— | 1 |
| 566 | H | 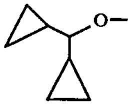 | H | Cl— | —Me | —CONH— | 1 |
| 567 | H | 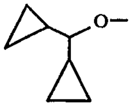 | H | Br— | —Me | —CONH— | 1 |
| 568 | H | 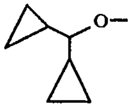 | H | 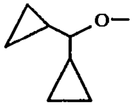 | —Me | —CONH— | 1 |
| 569 | H | 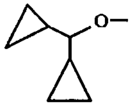 | H | H | —Me | —CONMe— | 1 |
| 570 | H | 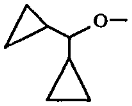 | Me— | H | —Me | —CONMe— | 1 |

-continued
| | | | | | | | |
|---|---|---|---|---|---|---|---|
| 571 | H | 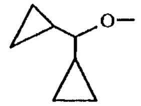 | Et— | H | —Me | —CONMe— | 1 |
| 572 | H | 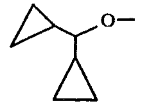 | iPr— | H | —Me | —CONMe— | 1 |
| 573 | H | 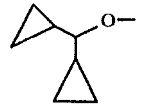 | Me—O— | H | —Me | —CONMe— | 1 |
| 574 | H | 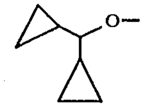 | Et—O— | H | —Me | —CONMe— | 1 |
| 575 | H | 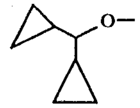 | iPr—O— | H | —Me | —CONMe— | 1 |
| 576 | —OH | 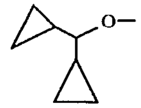 | H | H | —Me | —CONMe— | 1 |
| 577 | H | 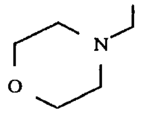 | H | H | —Me | —CONH— | 2 |
| 578 | H | 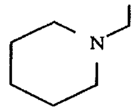 | H | H | —Me | —CONH— | 2 |

-continued
| | | | | | | | |
|---|---|---|---|---|---|---|---|
| 579 | H | 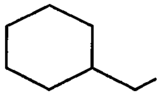 | H | H | —Me | —CONH— | 2 |
| 580 | H | 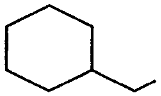 | H | H | —Me | —CONH— | 1 |
| 581 | H | 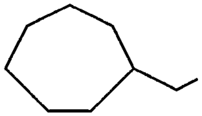 | H | H | —Me | —CONH— | 2 |
| 582 | H | 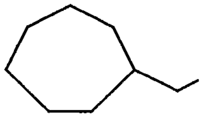 | H | H | —Me | —CONH— | 1 |
| 583 | H | 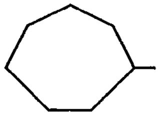 | H | H | —Me | —CONH— | 2 |
| 584 | H | 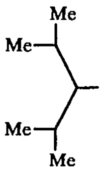 | H | H | —Me | —CONH— | 2 |
| 585 | H | 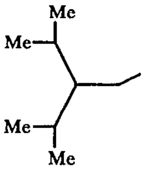 | H | H | —Me | —CONH— | 2 |

-continued
| | | | | | | | |
|---|---|---|---|---|---|---|---|
| 586 | H | 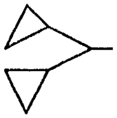 | H | H | —Me | —CONH— | 2 |
| 587 | H | 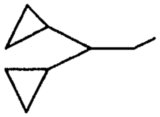 | H | H | —Me | —CONH— | 2 |
| 588 | H | 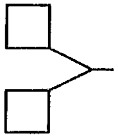 | H | H | —Me | —CONH— | 2 |
| 589 | H | 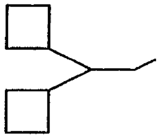 | H | H | —Me | —CONH— | 2 |
| 590 | H | 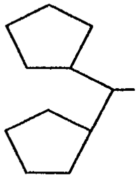 | H | H | —Me | —CONH— | 2 |
| 591 | H | 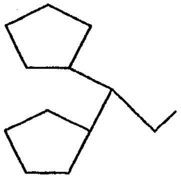 | H | H | —Me | —CONH— | 2 |

-continued
| | | | | | | | |
|---|---|---|---|---|---|---|---|
| 592 | H | 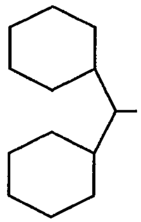 | H | H | —Me | —CONH— | 2 |
| 593 | H | 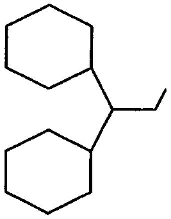 | H | H | —Me | —CONH— | 2 |
| 594 | H | 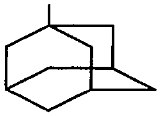 | H | H | —Me | —CONH— | 2 |
| 595 | H | 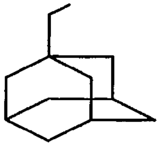 | H | H | —Me | —CONH— | 2 |
| 596 | H | 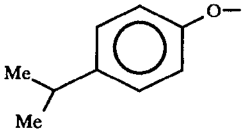 | H | Br— | —Me | —CONH— | 2 |
| 597 | H | 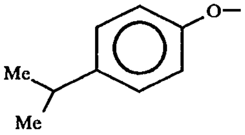 | H | 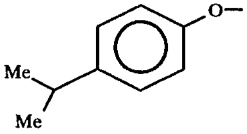 | —Me | —CONH— | 2 |

-continued
| | | | | | | |
|---|---|---|---|---|---|---|
| 598 | H | $-OCH_2O-$ | H | —Me | —CONH— | 2 |
| 599 | H | $-OCH_2O-$ | H | —Me | —CONH— | 1 |
| 600 | H | $-OCH_2CH_2O-$ | H | —Me | —CONH— | 2 |
| 601 | H | $-OCH_2CH_2O-$ | H | —Me | —CONH— | 1 |
| 602 | H | 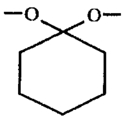 | H | —Me | —CONH— | 2 |
| 603 | H | 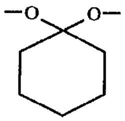 | H | —Me | —CONH— | 1 |
| 604 | H | 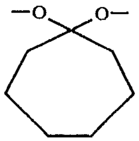 | H | —Me | —CONH— | 2 |
| 605 | H | 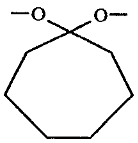 | H | —Me | —CONH— | 1 |
| 606 | H | 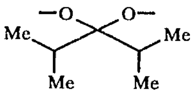 | H | —Me | —CONH— | 2 |
| 607 | H | 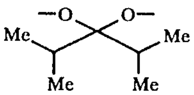 | H | —Me | —CONH— | 1 |
| 608 | H | 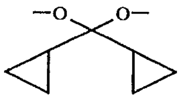 | H | —Me | —CONH— | 2 |

-continued
| | | | | | | | |
|---|---|---|---|---|---|---|---|
| 609 | H | 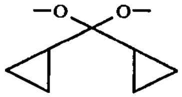 | | H | —Me | —CONH— | 1 |
| 610 | H | t-Bu— | H | t-Bu— | —Me | —CONH— | 2 |
| 611 | H | t-Bu— | H | t-Bu— | —Me | —CONMe— | 2 |
| 612 | H | t-Bu— | H | t-Bu— | —Me | —CONH— | 1 |
| 613 | H | t-Bu— | H | t-Bu— | —Me | —CONMe— | 1 |
| 614 | H | iPr— | H | iPr— | —Me | —CONH— | 2 |
| 615 | H | iPr— | H | iPr— | —Me | —CONH— | 1 |
| 616 | H | $—C(CH_3)_2CH_2CH_2C(CH_3)_2—$ | | H | —Me | —CONH— | 2 |
| 617 | H | $—C(CH_3)_2CH_2CH_2C(CH_3)_2—$ | | H | —Me | —CONH— | 1 |
| 618 | H | $—C(CH_3)_2CH_2CH_2C(CH_3)_2—$ | | H | —Me | —CONMe— | 2 |
| 619 | H | $—C(CH_3)_2CH_2CH_2C(CH_3)_2—$ | | H | —Me | —CONEt— | 2 |
| 620 | H | 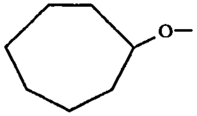 | H | H | —Me | $—SO_2NH—$ | 2 |
| 621 | H | 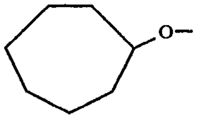 | H | H | —Me | $—SO_2NH—$ | 1 |
| 622 | H | 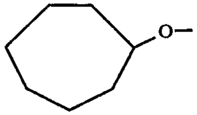 | H | H | —Me | $—SO_2NMe—$ | 2 |
| 623 | H | 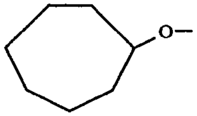 | H | H | —Me | $—SO_2NEt—$ | 2 |

TABLE 2
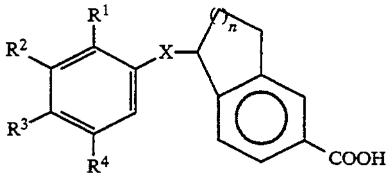
| Compd. No. | $R^1$ | $R^2$ | $R^3$ | $R^4$ | X | n |
|---|---|---|---|---|---|---|
| 624 | H | 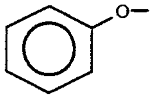 | H | H | —CONH— | 2 |
| 625 | H | 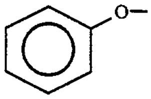 | H | H | —CONH— | 1 |
| 626 | H | 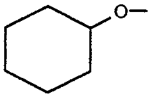 | H | H | —CONH— | 2 |
| 627 | H | 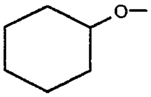 | H | H | —CONH— | 1 |
| 628 | H | 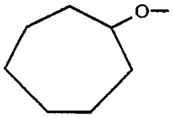 | H | H | —CONH— | 2 |
| 629 | H | 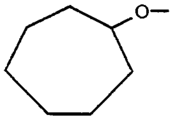 | H | H | —CONH— | 1 |
| 630 | H | 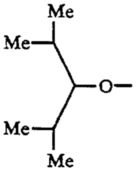 | H | H | —CONH— | 2 |
| 631 | H | 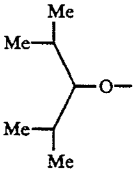 | H | H | —CONH— | 1 |
| 632 | H | 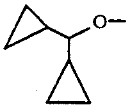 | H | H | —CONH— | 2 |
| 633 | H | 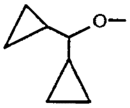 | H | H | —CONH— | 1 |

TABLE 2-continued
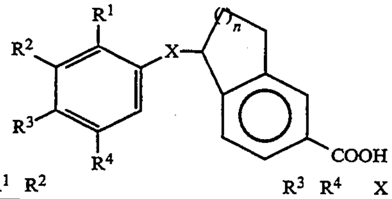
| Compd. No. | R1 | R2 | R3 | R4 | X | n |
|---|---|---|---|---|---|---|
| 634 | H | 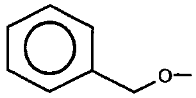 | H | H | —CONH— | 2 |
| 635 | H | 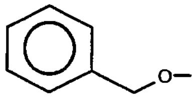 | H | H | —CONH— | 1 |
| 636 | H | 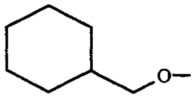 | H | H | —CONH— | 2 |
| 637 | H | 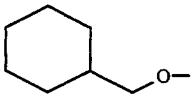 | H | H | —CONH— | 1 |
| 638 | H | 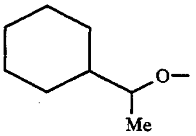 | H | H | —CONH— | 2 |
| 639 | H | 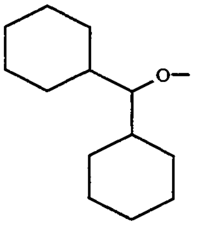 | H | H | —CONH— | 2 |
TABLE 3
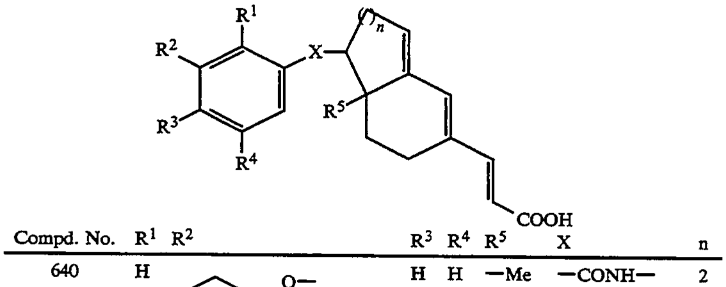
| Compd. No. | R1 | R2 | R3 | R4 | R5 | X | n |
|---|---|---|---|---|---|---|---|
| 640 | H | 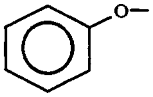 | H | H | —Me | —CONH— | 2 |
| 641 | H | 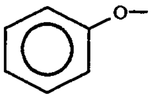 | H | H | —Me | —CONH— | 1 |

TABLE 3-continued
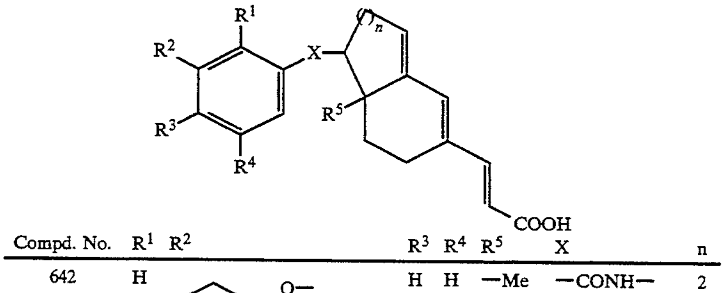
| Compd. No. | $R^1$ | $R^2$ | $R^3$ | $R^4$ | $R^5$ | X | n |
|---|---|---|---|---|---|---|---|
| 642 | H | 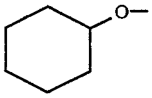 | H | H | —Me | —CONH— | 2 |
| 643 | H | 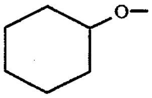 | H | H | —Me | —CONH— | 1 |
| 644 | H | 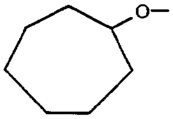 | H | H | —Me | —CONH— | 2 |
| 645 | H | 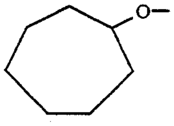 | H | H | —Me | —CONH— | 1 |
| 646 | H | 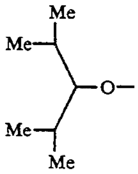 | H | H | —Me | —CONH— | 2 |
| 647 | H | 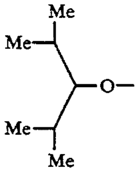 | H | H | —Me | —CONH— | 1 |
| 648 | H | 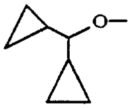 | H | H | —Me | —CONH— | 2 |
| 649 | H | 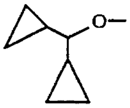 | H | H | —Me | —CONH— | 1 |
| 650 | H | 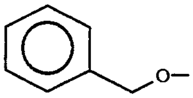 | H | H | —Me | —CONH— | 2 |
| 651 | H | 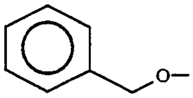 | H | H | —Me | —CONH— | 1 |

TABLE 3-continued
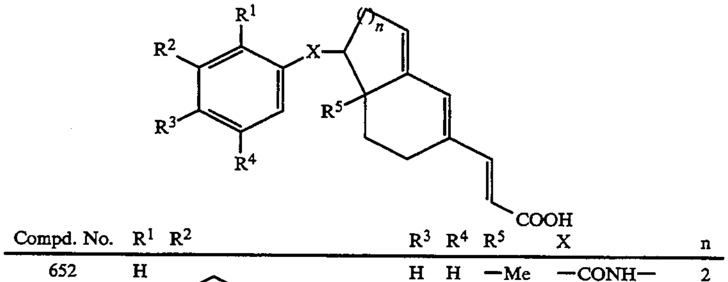
| Compd. No. | $R^1$ | $R^2$ | $R^3$ | $R^4$ | $R^5$ | X | n |
|---|---|---|---|---|---|---|---|
| 652 | H | 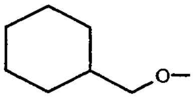 | H | H | —Me | —CONH— | 2 |
| 653 | H | 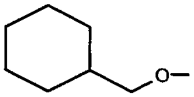 | H | H | —Me | —CONH— | 1 |
| 654 | H | 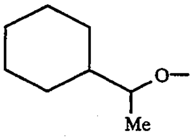 | H | H | —Me | —CONH— | 2 |
| 655 | H | 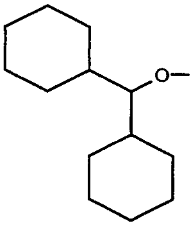 | H | H | —Me | —CONH— | 2 |
TABLE 4
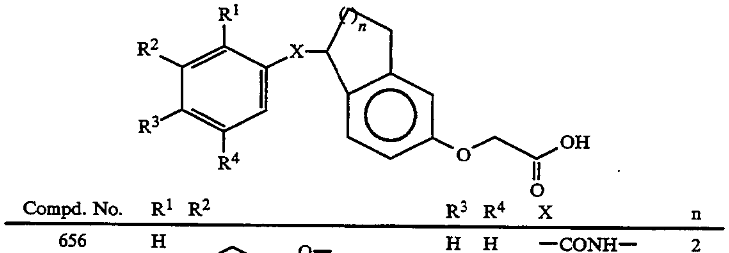
| Compd. No. | $R^1$ | $R^2$ | $R^3$ | $R^4$ | X | n |
|---|---|---|---|---|---|---|
| 656 | H | 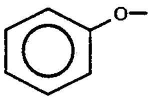 | H | H | —CONH— | 2 |
| 657 | H | 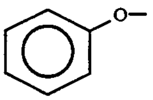 | H | H | —CONH— | 1 |
| 658 | H | 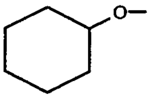 | H | H | —CONH— | 2 |
| 659 | H | 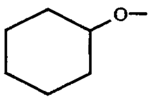 | H | H | —CONH— | 1 |

TABLE 4-continued
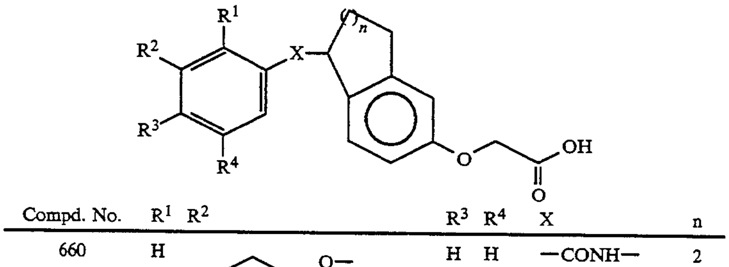
| Compd. No. | $R^1$ | $R^2$ | $R^3$ | $R^4$ | X | n |
|---|---|---|---|---|---|---|
| 660 | H | 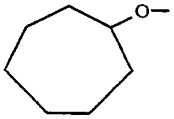 | H | H | —CONH— | 2 |
| 661 | H | 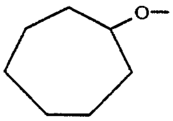 | H | H | —CONH— | 1 |
| 662 | H | 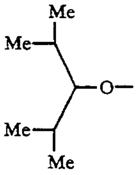 | H | H | —CONH— | 2 |
| 663 | H | 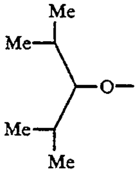 | H | H | —CONH— | 1 |
| 664 | H | 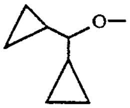 | H | H | —CONH— | 2 |
| 665 | H | 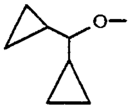 | H | H | —CONH— | 1 |
| 666 | H | 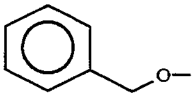 | H | H | —CONH— | 2 |
| 667 | H | 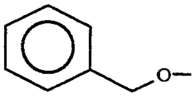 | H | H | —CONH— | 1 |
| 668 | H | 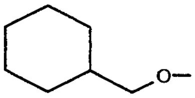 | H | H | —CONH— | 2 |
| 669 | H | 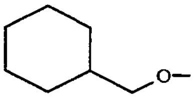 | H | H | —CONH— | 1 |

TABLE 4-continued

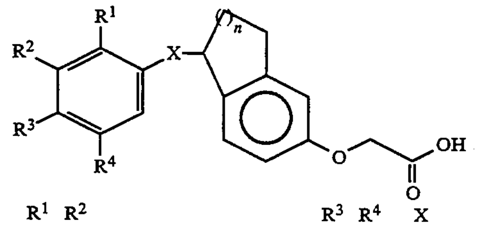

| Compd. No. | $R^1$ | $R^2$ | $R^3$ | $R^4$ | X | n |
|---|---|---|---|---|---|---|
| 670 | H | 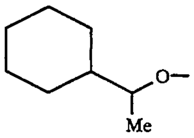 | H | H | —CONH— | 2 |
| 671 | H | 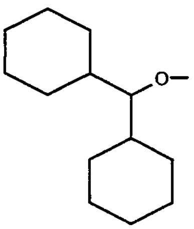 | H | H | —CONH— | 2 |

In Tables 1-4, Me means a methyl group, Et means an ethyl group, Pr means a propyl group, iPr means an isopropyl group, Bu means a butyl group, and Ac means an acetyl group.

The compounds of the general formula (I) can form a salt with a base. The base may be selected from those which can form a salt with the compound of the general formula (I). Examples of the salts are metal salts (e.g. sodium salt, magnesium, aluminium salt, etc.), ammonium salt, and amine salts (e.g. methylamine, ethylamine, diethylamine, triethylamine, pyrolidine, piperidine, morpholine, pyridine, aniline, etc.).

The compounds of the general formula (I) can be prepared, for example, in the manner as shown in the following synthetic route.

(1) Of the compounds of the general formula (I), the compounds wherein X is —$CONR^{13}$— are prepared as follows:

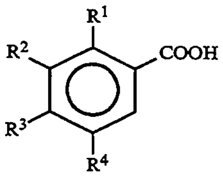

(III)

+

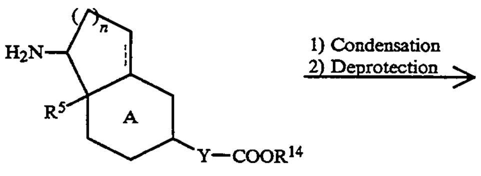

(IV)

-continued

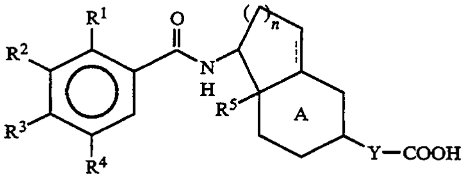

(Ia)

In the above formulae, $R^1$, $R^2$, $R^3$, $R^4$, $R^5$, n, Y and A have the same significance as defined in the general formula (I) above, and $R^{14}$ represents an alkyl group having 1 to 5 carbon atoms.

For example, the benzoic acid derivatives of the general formula (III) is allowed to condense with amino acid derivatives of the general formula (IV) in an appropriate solvent such as methylene chloride, chloroform, tetrahydrofuran, benzene or the like, or without solvent, in the presence or absence of a condensing agent and an organic base, or in the presence of a condensing agent without base. The condensing agent includes inorganic condensing agents such as phosphorus oxychloride, thionyl chloride or the like and organic condensing agents such as dicyclohexylcarbodi-imide, carbodiimidazole, oxalyl chloride, tosyl chloride or the like. The condensed product is subjected to hydrolysis with an alkali to give the objective compound (Ia). The hydrolysis is carried out in a mixture of water and methanol containing an alkali metal hydroxide such as sodium hydroxide or the like, or in a mixture of water, methanol and tetrahydrofuran.

The compound of the general formula (I) in which Y is a single bond can be prepared, for example, by condensing the compound of the general formula (III) with the amine derivative of the general formula (V) below using the method mentioned above, to give the compound of the general formula (VI) below, and this compound is allowed to react with carbon monoxide in the presence of an organic base, phosphine and palladium (II) in an alkanol (ROH) solvent or in a mixture of alkanol (ROH) of 1-5 carbon atoms with tetrahydrofuran, ether, methylene chloride or the like, to give alkoxycarbonyl compound of the general formula (VII) below, which is then subjected to hydrolysis with an alkali to give the objective compound. (The alkali-hydrolysis is carried out as described above.)

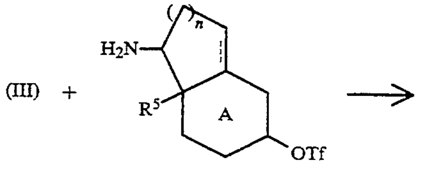

(V)

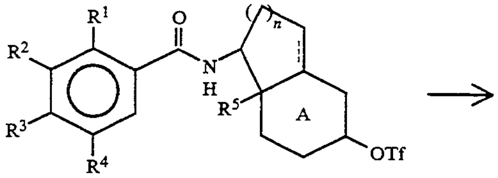

(VI)

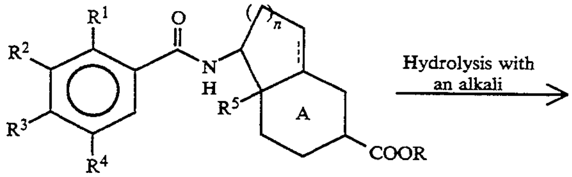

(VII)

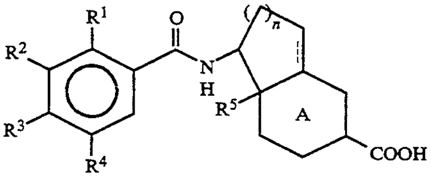

(VIII)

In the above formulae $R^1$, $R^2$, $R^3$, $R^4$, $R^5$, n and A have the same significance as defined above, R represents an alkyl group of 1 to 5 alkyl group, and Tf represents trifluoro-methanesulfonyl group.

(2) Production of the compound of the general formula (I) in which X is $-SO_2NR^{13}-$

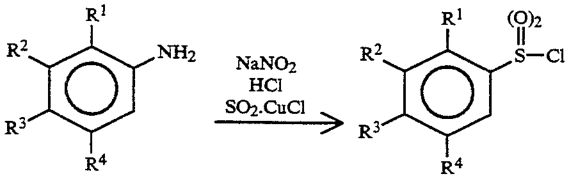

(IX) (X)

In the above formulae, $R^1$, $R^2$, $R^3$ and $R^4$ have the same significance as defined above.

For example, the aniline derivative of the general formula (IX) above is allowed to react with sodium nitrite or potassium nitrite in an appropriate solvent such as aqueous acetic acid, diluted hydrochloric acid or the like, to give a diazonium salt, which is allowed to react with cupric chloride and sulfur dioxide to give the sulfonyl chloride derivative of the general formula (X) above.

The compound of the general formula (XI) below can be prepared by reacting the compound of the general formula (X) with the compound of the general formula (IV) above in the presence or absence of an organic base such as triethylamine, pyridine or the like, in a halogen type solvent such as methylene chloride or the like and subjecting the resultant product to alkali-hydrolysis according to the method as described above.

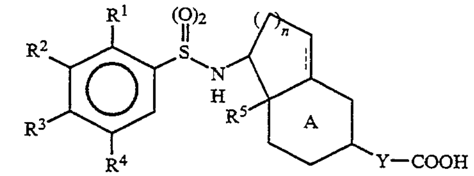

(XI)

In the above formulae (XI), $R^1$, $R^2$, $R^3$, $R^4$, $R^5$, n, Y and A have the same significance as defined in the general formula (I).

(3) Production of amino acid derivatives of the general formula (IV):

i) Production of compounds of the general formula (IV) in which Y is a single bond or —CH=CH—:

The starting 8a-methyl-3,4,8,8a-tetrahydro-1,6(2H,7H)naphthalenedione and 7a-methyl-7,7a-tetrahydro-1,5(6H)indadione are known compounds, and their optical activity is also known. Furthermore, the starting 6-hydrotetralone and 5-hydroxyindanone are known compounds.

The starting compounds are treated at temperature from −40° C. to room temperature in the presence of 1 mol equivalent of anhydrous trifluoromethanesulfonic acid and tertiary amine such as triethylamine, pyridine or the like, in an inert solvent such as methylene chloride, tetrahydrofuran or the like (Step a), and the resultant product is allowed to react with carbon monoxide or the like in the presence of an organic base, phosphine and palladium (II) in a mixture of alcohol (1-5 carbon atoms) with tetrahydrofuran or ether to give an alkoxy compound (Step b). This product is treated with a reducing agent such as sodium cyanoborohydride or the like in the presence of ammonium salt such as ammonium acetate, ammonium chloride or the like, in an alkanol solvent (1-5 carbon atoms) or in a mixture of alkanol (1-5 carbon atoms) with tetrahydrofuran or ether for subjecting only the ketone group to reductive amination (Step c).

The compound wherein Y is —CH=CH— can be prepared by using an alkyl acrylate or the like in place of carbon monoxide in Step b.

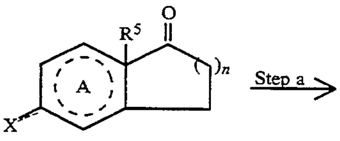

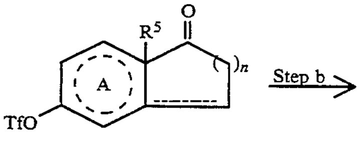

-continued

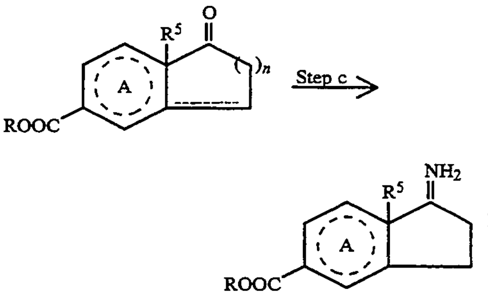

In the above formulae, $R^5$, X, n and A have the same significance as defined in the general formula (I), and R represents an alkyl group having 1-5 carbon atoms.

ii) Production of the compound of the general formula (IV) in which Y is —$OCH_2$—:

For example, 6-hydroxytetralone or 5-hydroxyindanone is allowed to react with α-haloacetic acid ester in the presence of a base such as sodium hydride, triethylamine or the like in a solvent such as methylene chloride, tetrahydrofuran, DMF or the like, and the resultant product is subjected to reductive animation to give the product.

The benzoic acid derivative of the formula (III) and aniline derivative of the formula (IX) are commercially available or can be prepared in a conventional manner from commercially available materials.

When the compounds of the present invention are used as medicaments, they can be formulated together with one or more conventional carriers suitable for the desired administering route. For example, formulations such as tablets, capsules, granules, powders, solutions or the like are prepared for oral route. Excipients, binders, lubricants, coloring agents, disintegrators, or the like, which are usually employed for the preparation of pharmaceutical formulations, can be used for preparing solid formulations for oral route. Examples of the excipients are lactose, starch, talc, magnesium stearate, crystalline cellulose, methyl cellulose, carboxymethyl cellulose, glycerin, sodium alginate, arabic gum and the like. Examples of the binders are polyvinyl alcohol, polyvinyl ether, ethyl cellulose, arabic gum, shellac, refined sugar and the like. Examples of the lubricants are magnesium stearate, talc, and the like. Additionally, coloring agents and disintegrators may be used. Further, tablets may be coated in a conventional manner. Liquid formulations include aqueous or oily suspensions, solutions, syrups, elixirs and the like, and can be prepared in a conventional manner. Injections may be prepared by adding pH adjusting agents, buffers, stabilizers, isotonic agents, topical anesthetics, or the like to the compound of the present invention. Subcutaneous, intramuscular or intravenous injections may be prepared in a conventional manner. For preparing suppositories, oily bases such as cacao oil, polyethylene glycol, Witepsol (Trademark of Dynamite Novel Company) or the like may be used.

Appropriate dosage of the formulation thus obtained varies depending upon symptoms, body weight, age or the like of particular patients. In general, appropriate daily dose to adult is in the range from about 0.01 to 2000 mg, and the daily dose is preferably administered in multiple doses of 1–4 times a day.

Appropriate salts of the compound (I) may be prepared using a non-toxic base. Such appropriate salts include those formed with inorganic bases (e.g. sodium slat, potassium salt, etc.), those formed with organic bases (e.g. triethylamine, etc.), and ammonium salts.

EXAMPLES

The present invention will be explained in more detail below by examples and reference examples. The examples are representative only and should not be construed as limiting in any respect.

EXAMPLE 1

Preparation of
5-(4'-phenoxybenzoylamino)-10-methyl-$\Delta^{1(2),8(9)}$-octalin-2-carboxylic acid (Compound No. 1 in Table 1)

To a solution of 4-phenoxybenzoic acid (410 mg, 1.91 mmol) in methylene chloride ( 4.0 ml) was added thionyl chloride (0.8 ml), and the resultant mixture was refluxed for 1 hour. The mixture was concentrated, and the residue was dissolved in methylene chloride (4.0 ml) and the resulting solution was dropwise added to a solution of 5-amino-10-methyl-$\Delta^{1(2),8(9)}$-octalin-2-carboxylic acid methyl ester (420 mg, 1.92 mmol), triethylamine (0.84 ml) and methylene chloride (4.2 ml) under ice cooling. The mixture was stirred at room temperature for 30 minutes, poured into chilled water (50 ml) and extracted with ethyl acetate. The organic extract was concentrated to dryness, and the residue was dissolved in 10% methanolic water (23 ml), mixed with potassium hydroxide (1.09 g, 16.5 mmol) and refluxed for 4 hours. The product was extracted with acidic chloroform, dried over magnesium sulfate and concentrated. The resulting residue was chromatographed on a silica gel column, eluting with chloroform-methanol to give the titled compound (464 mg, yield 60%) as white crystals.

m.p.96°-101° C.

$^1$H-NMR($CDCl_3$, 250MHz)δppm=7.73(d, 2H, 8.7Hz), 7.36(t-like, 2H, 7.4Hz), 7.1-7.2(m, 2H), 6.9-7.1(m, 4H), 5.96(br-d, 1H, 8.7Hz), 5.90(br-s, 1H), 4.10-4.25(m, 1H), 4.10-4.25(m, 1H), 2.10-2.60(m, 4H), 1.75-1.95(m, 3H), 1.40-1.55(m, 1H), 1.01(s, 1H)

IR(KBr):ν($cm^{-1}$)=3296, 2938, 1674, 1634, 1588, 1543, 1489, 1244, 1169.

EXAMPLE 2

Preparation of
5-(3'-phenoxybenzoylamino)-10-methyl-$\Delta^{1(2),8(9)}$-octalin-2-carboxylic acid (Compound No. 10 in Table 1)

The reaction was effected with 3-phenoxybenzoic acid (542 mg, 2.53 mmol) in the same manner as in Example 1 to give the titled compound (412 mg, yield 40%).

m.p.181°-186° C.

$^1$H-NMR($CDCl_3$, 250MHz)δ(ppm)=7.33-7.49 (m, 5H), 7.10-7.20 (m, 5H), 5.98(d, 1H, J=9.7Hz), 5.91(t, 1H, J=3.7Hz), 4.13-4.26(m, 1H), 2.14-2.59(m, 3H), 1.82-1.92(m, 4H), 1.40-1.53(m, 1H), 1.02(s, 3H)

IR(KBr):ν($cm^{-1}$)=3285, 3069, 9240, 1672, 1634, 1580, 1555, 1483, 1427, 1306, 1275, 1233.

EXAMPLE 3

Preparation of
5-(2'-phenoxybenzoylamino)-10-methyl-$\Delta^{1(2),8(9)}$-octalin-2-carboxylic acid (Compound No. 12 in Table 1)

The reaction was effected with 2-phenoxybenzoic acid (488 mg, 2.28 mmol) as in the same manner as in Example 1 to give the titled compound (330 mg, yield 36% ).

m.p.75°–77° C.

$^1$H-NMR($CDCl_3$, 250MHz)δ=8.23(dd, 1H, 1.8Hz, 7.9Hz), 7.73(br-d, 1H, 8.0Hz), 7.3–7.42(m, 3H), 7.1–7.3 (m, 3H), 7.00(d, 2H, 7.9Hz), 6.87(d, 1H, 8.2Hz), 5.85(br-s, 1H), 4.1–4.2(m, 1H), 2.2–2.5(m, 3H), 2.0–2.2(m, 1H), 1.8–1.9(m, 1H), 1.6–1.8(m, 2H), 1.2–1.4(m, 1H), 0.84(s, 3H)

IR(KBr):ν($cm^{-1}$)=3403, 3069, 2932, 1640, 1601, 1534, 1478, 1449, 1223, 753.

EXAMPLE 4

Preparation of 5-[3'-(p-isopropylphenoxy)benzoylamino]-10-methyl-$\Delta^{1(2),8(9)}$-octalin-2-carboxylic acid (Compound No. 16 in Table 1)

The reaction was effected with 3-(p-isopropylphenoxy)benzoic acid (177 mg, 0.74 mmol) in the same manner as in Example 1 to give the titled compound (253 mg, yield 77%).

m.p.146°–149° C.

$^1$H-NMR($CDCl_3$, 250MHz)δ=7.3–7.45(m, 3H), 7.15–7.23(m, 3H), 7.10(dd, 1.4Hz, 8.0Hz), 6.90–6.96(m, 2H), 5.98(br-d, 1H, 8.7Hz), 5.90(br-s, 1H), 4.1–4.2(m, 1H), 2.80–2.95(m, 1H), 2.10–2.60(m, 4H)1.70–1.95(m, 3H), 1.35–1.50(m, 1H), 1.22, 1.25(each s, each 3H), 0.99(s, 3H)

IR(KBr):ν($cm^{-1}$)=3312, 2959, 2930, 2870, 1674, 1636, 1582, 1541, 1507, 1480, 1429, 1306, 1279, 1236.

EXAMPLE 5

Preparation of 5-[3'-(m-isopropylphenoxy)benzoylamino]-10-methyl-$\Delta^{1(2),8(9)}$-octalin-2-carboxylic acid (Compound No. 17 in Table 1)

The reaction was effected with 3-(m-isopropylphenoxy)benzoic acid (704 mg, 2.75 mmol) in the same manner as in Example 1 to give the titled compound (612 mg, yield 50%).

m.p.83°–86° C.

$^1$H-NMR($CDCl_3$, 250MHz)δ=7.3–7.47(m, 3H), 7.25(dd, 1H, 7.9Hz, 7.8Hz), 7.17(br-s, 1H), 7.10(ddd, 1.3Hz, 2.2Hz, 7.9Hz), 7.00(br-d, 1H, 7.8Hz), 6.90(dd, 1H, 2.1Hz, 1.8Hz), 6.79(ddd, 1H, 0.8Hz, 2.2Hz, 7.9Hz), 5.95(d, 1H, 9.7Hz), 5.90(dd, 1H, 3.8Hz, 3.7Hz), 4.11–4.23 (m, 1H), 2.87(dq, 1H, each 6.9Hz), 2.52(dd, 1H, 4.7Hz, 19Hz), 2.10–2.47(m, 3H), 1.76–1.90(m, 3H), 1.37–1.49(m, 1H), 1.22(d, 6H, 6.9Hz), 1.02(s, 3H)

IR(KBr):ν($cm^{-1}$)=3285, 3071, 2961, 2870, 2822, 1672, 1634, 1576, 1555, 1481, 1427, 1308, 1273, 1244.

EXAMPLE 6

Preparation of 5-[3'-(o-isopropylphenoxy)benzoylamino]-10-methyl-$\Delta^{1(2),8(9)}$-octalin- 2-carboxylic acid (Compound No. 18 in Table 1)

The reaction was effected with 3-(o-isopropylphenoxy)benzoic acid (347 mg, 1.44 mmol) in the same manner as in Example 1 to give the titled compound (344 mg, yield 54% ).

m.p.192°–194° C.

$^1$H-NMR($CDCl_3$, 250MHz)δ=7.3–7.4 (m, 4H), 7.1–7.2(m, 2H), 6.98(dd-like, 1H, 1.4Hz, 8.0Hz), 6.80–6.90(m, 1H), 5.98(br-d, 1H, 8.7Hz), 5.90(br-s, 1H), 4.1–4.25(m, 1H), 3.1–3.3(m, 1H), 2.1–2.6 (m, 4H), 1.7–1.9(m, 3H), 1.3–1.5(m, 1H), 1.21, 1.19(each s, each 3H), 0.99(s, 3H)

IR(KBr):ν($cm^{-1}$)=3291, 3071, 2961, 2870, 2824, 2629, 1674, 1634, 1578, 1555, 1483, 1451, 1429, 1306, 1275, 1235, 1184.

EXAMPLE 7

Preparation of 5-[3'-(p-tolyloxy)benzoylamino]-10-methyl-$\Delta^{1(2),8(9)}$-octalin-2-carboxylic acid (Compound No. 21 in Table 1)

To a mixture of 3-(p-tolyloxy)benzoic acid (414 mg, 1.81 mmol), 5-amino-10-methyl-$\Delta^{1(2),8(9)}$-octalin-2-carboxylic acid methyl ester (401 mg, 1.81 mmol), triethylamine (1.26 mg, 9.05 mmol) and methylene chloride (4.1 ml) was added thionyl chloride (396 μl, 5.43 mmol) with ice cooling. The resultant mixture was stirred at room temperature for 30 minutes, poured into chilled water (50 ml), and extracted with ethyl acetate. The organic extract was concentrated, and the residue was dissolved in a mixture of 10% methanol (12 ml) and THF (3.7 ml), mixed with potassium hydroxide (566 mg, 8.57 mmol) and refluxed for 3 hours. The product was extracted with acidic chloroform, and the organic layer was dried and concentrated. The resultant residue was chromatographed on a silica gel column, eluting with chloroform-methanol to give the titled compound (263 mg, yield 35%).

m.p.168°–172° C.

$^1$H-NMR($CDCl_3$, 250MHz)δ=7.3–7.4(m, 3H), 7.0–7.2(m, 4H), 6.90 (d, 2H, 8.5Hz), 6.00(d, 1H, 9.6Hz), 5.89(br-s, 1H), 4.1–4.2(m, 1H), 2.1–2.6(m, 4H), 2.32(s, 3H), 1.7–1.9(m, 3H), 1.40 (ddd, 1H, 5.7Hz, 5.7Hz, 13Hz), 0.99 (s, 3H)

IR(KBr):ν($cm^{-1}$)=3283, 2940, 1672, 1634, 1580, 1559, 1507, 1481, 1427, 1306, 1275, 1238, 1209, 1186.

EXAMPLE 8

Preparation of 5-[3'-(p-t-butylphenoxy)benzoylamino]-10-methyl-$\Delta^{1(2),8(9)}$-octalin-2-carboxylic acid (Compound No. 24 in Table 1)

The reaction was effected with 3-(p-t-butylphenoxy)-benzoic acid (435 mg, 1.61 mmol) in the same manner as in Example 7 to give the titled compound (282 mg, yield 38%).

m.p.233°–238° C.

1H-NMR($CDCl_3$, 250MHz)δ=7.3–7.45(m, 5H), 7.16(d, 1H, 1.5Hz), 7.52(dd-like, 1H, 1Hz, 1.5Hz, 8.0Hz), 6.94(d, 2H, 8.9Hz), 5.96 (br-d, 1H, 8.7Hz), 5.86(br-s, 1H), 4.05–4.20(m, 1H), 2.10–2.60(m, 4H), 1.75–1.95 (m, 3H), 1.40–1.55 (m, 1H), 1.30 (s, 9H), 0.99(s, 3H)

IR(KBr):ν($cm^{-1}$)=3266, 2965, 2870, 1680, 1634, 1613, 1580, 1543, 1508, 1480, 1426, 1306, 1279, 1236.

EXAMPLE 9

Preparation of 5-{3''-[p-(2'-methylpropyl]phenoxy)benzoylamino}-10-methyl-$\Delta^{1(2),8(9)}$-octalin-2-carboxylic acid (Compound No. 30 in Table 1)

The reaction was effected with 3-p-(2'-methylpropyl)phenoxybenzoic acid (246 mg, 0.91 mmol) in the same manner as in Example 7 to give the titled compound (290 mg, yield 69%).

m.p.142°–148° C.

$^1$H-NMR($CDCl_3$, 250MHz)δ=7.3–7.45 (m, 3H), 7.18(s-like, 1H), 7.06–7.13(m, 3H), 6.92(d, 2H, 11.3Hz), 5.95(d, 1H, 9.7Hz), 5.90 (br-s, 1H), 4.10–4.22(m, 1H), 4.52(dd, 1H, 4.1Hz, 18.3Hz), 2.44(d, 2H, 7.2Hz), 2.15–4.60(m, 3H), 1.75–1.95(m, 4H), 1.42(ddd, 1H, 5.7Hz, 5.7Hz, and 13Hz), 0.99(s, 3H), 0.89(d, 6H, 6.5Hz)

IR(KBr):ν($cm^{-1}$)=3289, 2959, 2870, 1672, 1638, 1609, 1584, 1545, 1505, 1481, 1431, 1308, 1279, 1235.

EXAMPLE 10

Preparation of 5-[3'-(p-cyclopentylphenoxy)benzoylamino]-10-methyl-$\Delta^{1(2),8(9)}$-octalin-2-carboxylic acid (Compound No. 33 in Table 1)

The reaction was effected with 3-(p-cyclopenthylphenoxy)benzoic acid (488 mg, 1.73 mmol) in the same manner as in Example 7 to give the titled compound (240 mg, yield 30%).

m.p.229°–231° C.

$^1$H-NMR($CDCl_3$, 250MHz)δ=7.3–7.4 (m, 3H), 7.15–7.25 (m, 3H), 7.09 (ddd, 1H, 1.4Hz, 0, 8Hz, 9.2Hz), 6.93 (d, 2H, 8.5Hz), 5.96(d, 1H, 9.6Hz), 5.89(br-s, 1H), 4.05–4.20(m, 1H), 2.85–3.05(m, 1H), 1.95–2.30(m, 6H), 1.30–1.90(m, 10H), 0.99(s, 3H)

IR(KBr):ν($cm^{-1}$)=3337, 2944, 2868, 1676, 1638, 1613, 1578, 1543, 1505, 1483, 1426, 1323, 1304, 1275, 1236.

EXAMPLE 11

Preparation of 5-[3'-(p-cyclohexylphenoxy)benzoylamino]-10-methyl-$\Delta^{1(2),8(9)}$-octalin-2-carboxylic acid (Compound No. 36 in Table 1)

The reaction was effected with 3-(p-cyclohexylphenoxy)benzoic acid (415 mg, 1.40 mmol) in the same manner as in Example 7 to give the titled compound (263 mg, yield 33%).

m.p.124°–125° C.

$^1$H-NMR($CDCl_3$, 250MHz)δ=7.3–7.45(m, 3H), 7.1–7.2 (m, 3H), 7.10(ddd, 1H, 1.3Hz, 2.4Hz, 7.9Hz), 6.92(d, 2H, 8.5Hz), 5.97(br-d, 1H, 9.5Hz), 5.89(br-s, 1H), 4.10–4.25(m, 1H), 2.10–2.60(m, 5H), 1.65–1.95(m, 8H), 1.10–1.50(m, 6H), 0.99(s, 3H)

IR(KBr):ν($cm^{-1}$)=3443, 2926, 2851, 1676, 1636, 1580, 1541, 1507, 1480, 1429, 1306, 1273, 1238.

EXAMPLE 12

Preparation of 5-[3'-(p-N-methylaminocarbonylphenoxy)benzoylamino]-10-methyl-$\Delta^{1(2),8(9)}$-octalin-2-carboxylic acid (Compound No. 38 in Table 1)

The reaction was effected with 3-(p-N-methylaminocarbonylphenoxy)benzoic acid (448 mg, 1.19 mmol) in the same manner as in Example 7 to give the titled compound (35 mg, yield 6.4%).

m.p.123°–127° C.

$^1$H-NMR($CDCl_3$, 250MHz)δ=7.72(d, 2H, 8.6Hz), 7.35–7.55(m, 3H), 7.10–7.20(m, 2H), 6.97(d, 2H, 8.6Hz), 6.30 (br-d-like), 6.10(br-d, 1H, 9.5Hz), 5.87 (br-s, 1H), 2.96, 2.98(each s, total 3H), 2.1–2.6 (m, 4H), 1.6–1.9 (m, 3H), 1.3–1.5(m, 1H), 0.99(s, 3H)

IR(KBr):ν($cm^{-1}$)=3337, 3069, 2936, 1684, 1636, 1578, 1543, 1501, 1316, 1240, 1177.

EXAMPLE 13

Preparation of 5-[3'-(3,5-dimethylphenoxy)benzoylamino]-10-methyl-$\Delta^{1(2),8(9)}$-octalin-2-carboxylic acid (Compound No. 42 in Table 1)

The reaction was effected with 3-(3',5'-dimethylphenoxy) benzoic acid (271 mg, 1.12 mmol) in the same manner as in Example 7 to give the titled compound (135 mg, yield 28%).

m.p.137°–142° C.

$^1$H-NMR($CDCl_3$, 250MHz)δ=7.3–7.45(m, 3H), 7.18(d, 1H, 2.0Hz), 7.09(ddd, 1H, 1.2Hz, 2.2Hz, 9.0 Hz), 6.76(d, 1H, 0.6Hz), 6.62(d, 2H, 0.6Hz), 5.97(br-d, 1H, 9.6Hz), 5.89(dd, 1H, each 3.7Hz), 4.10–4.25 (m, 1H), 2.1–2.6(m, 4H), 2.27(s, 6H), 2.7–2.95(m, 3H), 1.43(ddd, 1H, 5.7Hz, 5.7Hz and 13Hz), 0.99(s, 3H)

IR(KBr):ν($cm^{-1}$)=3290, 2938, 1676, 1636, 1578, 1541, 1476, 1456, 1296, 1275, 1225, 1142.

EXAMPLE 14

Preparation of 5-[3'-(5",6",7",8"-tetrahydro-2"-naphtoxy)benzoylamino]-10-methyl-$\Delta^{1(2),8(9)}$-octalin-2-carboxylic acid (Compound No. 45 in Table 1)

The reaction was effected with 3-(5',6',7',8'-tetrahydro-2'-naphtoxy)benzoic acid (324 mg, 1.21 mmol) in the same manner as in Example 7 to give the titled compound (131 mg, yield 24%).

m.p.141°–151° C.

$^1$H-NMR($CDCl_3$, 250MHz)δ=7.30–7.50 (m, 3H), 7.20(br-s, 1H), 7.11(ddd, 1H, 1.5Hz, 2.5Hz, 7.8Hz), 7.04(d, 1H, 8.1Hz), 6.70–6.80 (m, 2H), 5.97(d, 1H, 9.7Hz), 5.92(br-s, 1H), 4.12–4.25(m, 1H), 2.7–2.8(m, 4H), 2.54(dd, 1H, 4.7Hz, 18.1Hz), 2.2–2.5(m, 3H), 1.70–2.0 (m, 7H), 1.45(ddd, 1H, 5.2Hz, 5.2Hz and 12.5Hz), 1.02(s, 3H)

IR(KBr):ν($cm^{-1}$)=3287, 2934, 2859, 2633, 1674, 1636, 1580, 1557, 1497, 1481, 1427, 1306, 1275, 1248, 1188, 1146.

EXAMPLE 15

Preparation of 5-(3'-benzyloxy-benzoylamino)-10-methyl-$\Delta^{1(2),8(9)}$-octalin-2-carboxylic acid (Compound No. 46 in Table 1)

The reaction was effected with 3-benzyloxybenzoic acid (516 mg, 2.26 mmol) in the same manner as in Example 1 to give the titled compound (325 mg, yield 34.5%).

m.p.175°–177° C.

$^1$H-NMR($CDCl_3$, 250MHz)δ=7.30–7.47 (m, 8H), 7.21(s, 1H), 7.13 (dd, 1H, 2.5Hz, 8.0Hz), 5.99(d, 1H, J=9.7Hz), 5.92(t, 1H, J=3.7Hz), 5.13(s, 2H), 4.16–4.26(m, 1H), 2.31–2.60(m, 4H), 1.80–1.92(m, 3H), 1.47(dt, 1H, J=5.5Hz, 12.8Hz)

IR(KBr):ν($cm^{-1}$)=3291, 3065, 3036, 2942, 2910, 2870, 1680, 1640, 1611, 1580, 1549, 1483, 1454, 1426, 1304, 1285, 1235.

EXAMPLE 16

Preparation of 5-(3'-diphenylmethyloxybenzoylamino)-10-methyl-$\Delta^{1(2),8(9)}$-octalin-2-carboxylic acid (Compound No. 50 in Table 1)

The reaction was effected with 3-diphenylmethyloxybenzoic acid (498 mg, 1.64 mmol) in the same manner as in Example 1 to give the titled compound (204 mg, yield 25%).

m.p.89°-91° C.

$^1$H-NMR($CDCl_3$, 250MHz)δ=7.1-7.5(m, 14H), 7.0-7.1(m, 1H), 6.25(s, 1H), 5.8-5.9(m, 2H), 4.0-4.2(m, 1H), 2.1-2.6(m, 4H), 2.7-2.9(m, 3H), 1.35-1.5(m, 1H), 0.96(s, 3H)

IR(KBr):ν($cm^{-1}$)=3308, 3063, 3030, 2934, 1684, 1634, 1580, 1524, 1483, 1454, 1429, 1273, 1233, 1186, 1020, 748, 700.

EXAMPLE 17

Preparation of 5-(3'-cyclopentyloxybenzoylamino)-10-methyl-$\Delta^{1(2),8(9)}$-octalin-2-carboxylic acid (Compound No. 51 in Table 1)

The reaction was effected with 3-cyclopentyloxybenzoic acid (413 mg, 2.0 mmol) in the same manner as in Example 1 to give the titled compound (230 mg, yield 29%).

m.p.175°-176° C.

$^1$H-NMR($CDCl_3$, 250MHz)δ=7.26-7.36(m, 3H), 7.21(s, 1H), 7.02(dd, 1H, J=2.5Hz, 8.0Hz), 6.01(d, 1H, J=9.7Hz), 5.92(t, 1H, J=3.7Hz), 4.80-4.88(m, 1H), 4.16-4.26(m, 1H), 2.22-2.59(m, 3H), 1.56-2.00(m, 12H), 1.46(dt, 1H, J=5.5Hz, 12.8Hz), 1.03(s, 3H)

R(KBr):ν($cm^{-1}$)=3291, 2936, 2870, 1680, 1636, 1589, 1555, 1485, 1426, 1319, 1275, 1242.

EXAMPLE 18

Preparation of 5-(3'-cyclohexyloxybenzoylamino)-10-methyl-$\Delta^{1(2),8(9)}$-octalin-2-carboxylic acid (Compound No. 63 in Table 1)

The reaction was effected with 3-cyclohexyloxybenzoic acid (530 mg, 2.41 mmol) in the same manner as in Example 1 to give the titled compound (292 mg, yield 29.0%).

m.p.192°-194 ° C.

$^1$H-NMR($CDCl_3$, 250MHz)δ=7.21-7.37(m, 4H), 7.04(dd, 1H), 2.5Hz, 8.0Hz), 6.01(d, 1H, J=9.3Hz), 5.92(t, 1H, J=3.7Hz), 4.15-4.38 (m, 2H), 2.21-2.59(m, 4H), 1.76-2.05(m, 7H), 1.29-1.64 (m, 7H), 1.03 (s, 3H)

IR(KBr):ν($cm^{-1}$)=3312, 2936, 2865, 1672, 1636, 1609, 1576, 1539, 1481, 1429, 1304, 1287, 1236, 1051.

EXAMPLE 19

Preparation of 5-(3'-cycloheptyloxybenzoylamino)-10-methyl-$\Delta^{1(2),8(9)}$-octalin-2-carboxylic acid (Compound No. 111 in Table 1)

The reaction was effected with 3-cycloheptyloxybenzoic acid (2.17 mg, 9.26 mmol) in the same manner as in Example 7 to give the titled compound (2.8 mg, yield 71%).

m.p.224°-226 ° C.

$^1$H-NMR($CDCl_3$, 250MHz)δ=7.1-7.4(m, 4H), 6.98-7.02(m, 1H), 6.01(br-d, 1H, 9.7Hz), 5.92(t-like 1H, J≐1.0Hz), 4.20-4.35(m, 1H), 4.1-4.3(m, 1H), 2.1-2.6(m, 4H), 2.0-2.1(m, 2H), 1.3-1.9(m, 8H), 1.03(s, 3H)

IR(KBr):ν($cm^{-1}$)=3304, 2932, 2863, 1674, 1638, 1609, 1576, 1545, 1483, 1456, 1427, 1323, 1306, 1277, 1236, 1188, 1022, 750.

EXAMPLE 20

Preparation of 5-(3'-cyclooctyloxybenzoylamino)-10-methyl-$\Delta^{1(2),8(9)}$-octalin-2-carboxylic acid (Compound No. 159 in Table 1)

The reaction was effected with 3-cyclooctyloxybenzoic acid (268 mg, 1.08 mmol) in the same manner as in Example 7 to give the titled compound (358 mg, yield 76%).

m.p.214°-218° C.

$^1$H-NMR($CDCl_3$, 250MHz)δ=7.2-7.35(m, 3H), 7.17(d, 1H, 1.4Hz), 7.00(dd, 1H, 2.4Hz, 8.0Hz), 5.98(d, 1H, 10Hz), 5.90(t, 1H, 3.6Hz), 4.4-4.5(m, 1H),4.18(ddd, 1H, 5.2Hz, 10Hz and 10Hz), 2.53(dd, 1H, 5.6Hz, 19Hz), 2.1-2.4(m, 3H), 1.4-2.0(m, 18H), 1.01(s, 3H)

IR(KBr):ν($cm^{-1}$)=3299, 2928, 1676, 1638, 1609, 1576, 1549, 1478, 1424, 1323, 1287.

EXAMPLE 21

Preparation of 5-[3'-(4-methylcyclohexyloxy)benzoylamino]-10-methyl-$\Delta^{1(2),8(9)}$-octalin-2-carboxylic acid (Compound No. 207 in Table 1)

The reaction was effected with 3-(4-methylcyclohexyloxy) benzoic acid (423 mg, 1.81 mmol) in the same manner as in Example 1 to give the titled compound (375 mg, yield 49.0%).

m.p.194°-199° C.

$^1$H-NMR($CDCl_3$, 250MHz)δ=7.21-7.40(m, 4H), 7.06(dd, 1H, J=2.5Hz, 8.0Hz), 5.92(t, 1H, J=3.7Hz), 5.51(d, 1H, J=9.7Hz), 4.14-4.61(m, 2H), 2.23-2.60(m, 3H), 1.34-2.07(m, 14H), 1.03 (s, 3H), 0.94(d, 3H, J=5.0Hz)

IR(KBr):ν($cm^{-1}$)=3293, 2932, 2870, 2633, 1674, 1637, 1578, 1545, 1481, 1427, 1277, 1236, 1124, 1036.

EXAMPLE 22

Preparation of 5-[3-(4-isopropylcyclohexyloxy)benzoylamino]-10-methyl-$\Delta^{1(2),8(9)}$-octalin-2-carboxylic acid (Compound No. 255 in Table 1)

The reaction was effected with 3-(4-isopropylcyclohexyloxy)benzoic acid (474 mg, 1.81 mmol) in the same manner as in Example 1 to give the titled compound (185 mg, yield 23%).

m.p.128°-129° C. 1H-NMR($CDCl_3$, 250MHz)δ=7.20-7.40(m, 4H), 7.10(s-like, 1H), 6.95-7.05(m, 1H), 5.99(br-d, 1H, 9.8Hz), 5.86(t-like, 1H, J≐1Hz), 4.1-4.3(m, 2H), 2.1-2.6(m, 6H), 1.8-2.0 (m, 5H), 1.1-1.6(m, 7H), 1.02(s, 3H), 0.88(s, 6H)

IR(KBr):ν($cm^{-1}$)=3324, 2938, 2868, 2627 , 1678, 1636, 1580, 1535, 1483, 1431, 1275, 1238, 1132, 1080, 1040, 1003.

EXAMPLE 23

Preparation of 5-[3-(4-trans-t-butylcyclohexyloxy)benzoylamino]-10-methyl-$\Delta^{1(2),8(9)}$-octalin-2-carboxylic acid (Compound No. 303 in Table 1)

The reaction was effected with 3-(4-trans-t-butylcyclo-hexyloxy)benzoic acid (237 mg, 0.86 mmol) in the same manner as in Example 1 to give the titled compound (154 mg, yield 38.5%).

m.p.129°-134° C.

$^1$H-NMR($CDCl_3$, 250MHz)δ=7.21–7.39(m, 4H), 7.04(ddd, 1H, J=2.5Hz, 2.5Hz, 8.0Hz), 6.03(d, 1H, 9.7Hz, 5.92(t, 1H, J=3.7Hz), 4.14–4.29(m, 1H), 2.15–2.61(m, 6H), 1.82–1.96(m, 5H), 1.31–1.54 (m, 3H), 1.09–1.18(m, 3H), 1.03(s, 3H), 0.88(s, 9H)

IR(KBr):ν($cm^{-1}$)=3439, 2946, 2866, 1678, 1638, 1582, 1528, 1481, 1275, 1236, 1049, 1030.

EXAMPLE 24

Preparation of 5-[3′-(4″-cis-t-butylcyclohexyloxy)benzoylamino]-10-methyl-$\Delta^{1(2),8(9)}$-octalin-2-carboxylic acid (Compound No. 351 in Table 1)

The reaction was effected with 3-(4-cis-t-butylcyclohexyloxy)benzoic acid (320 mg, 1.16 mmol) in the same manner as in Example 1 to give the titled compound (102 mg, yield 52.6%).

m.p.137°-139° C.

$^1$H-NMR($CDCl_3$, 250MHz)δ=7.21–7.37 (m, 4H), 7.06(ddd, 1H, J=2.5Hz, 2.5Hz, 8Hz), 5.92(t, 1H, J=3.7Hz), 4.61(br s, 1H), 4.16–4.27 (m, 1H), 2.06–2.62(m, 7Hz), 1.81–1.96(m, 3H), 1.39–1.62(m, 7H), 1.03(s, 3H), 0.88(s, 9H)

IR(KBr):ν($cm^{-1}$)=3319, 2943, 2868, 1676, 1636, 1582, 1530, 1481, 1429, 1306, 1273, 1236, 1182, 1007.

EXAMPLE 25

Preparation of 5-[3′-(N-acetyl-4″-piperidinyloxy)benzoylamino]-10-methyl-$\Delta^{1(2),8(9)}$-octalin-2-carboxylic acid (Compound No. 399 in Table 1)

The reaction was effected with 3-(N-acetyl-4′-piperidinyloxy)benzoic acid (203 mg, 0.77 mmol) in the same manner as in Example 7 to give the titled compound (303 mg, yield 87%).

m.p.68°-72° C.

$^1$H-NMR($CDCl_3$, 250MHz)δ=7.40(d-like, 1H), 7.35(d, 1H, 7.9Hz), 7.25–7.29(m, 1H), 7.19(d, 1H, 1.5Hz), 7.06 (ddd, 1H, 1.6Hz, 0.8Hz, 7 . 1Hz), 6.02(br-d, 1H, 9.7Hz), 5.93 (t, 1H, 3.7Hz), 4.61–4.67 (m, 1H), 4.14–4.23(m, 1H), 3.3–3.9(m, 4H), 2.1–2.6 (m, 4H), 2.13 (s, 1H), 1.7–2.0(m, 3H), 1.4–1.6(m, 1H), 1.04(s, 3H)

IR(KBr):ν($cm^{-1}$)=3384, 2934, 1698, 1632, 1580, 1539, 1483, 1454, 1364, 1318, 1233, 1034.

EXAMPLE 26

Preparation of 5-[3′-(N-methyl-4″-piperidinyloxy)benzoylamino]-10-methyl-$\Delta^{1(2),8(9)}$-octalin-2-carboxylic acid (Compound No. 401 in Table 1)

The reaction was effected with 3-(N-methyl-4′-piperidinyloxy)benzoic acid (168 mg, 0.62 mmol) in the same manner as in Example 7 to give the titled compound (70 mg, yield 26%).

m.p.63°-65° C.

$^1$H-NMR($CDCl_3$, 250MHz)δ=7.35–7.45(m, 3H), 7.11(d, 1H, 1.9Hz), 7.08(ddd, 1H, 2.7Hz, 2.5Hz, 6.5Hz), 6.84(br-d, 1H, 9.6Hz), 5.88 (br-s, 1H), 4.75(br-s, 1H), 4.1–4.3(m, 1H), 3.2–3.4(m, 4H), 2.82 (s, 3H), 1.8–2.6 (m, 11H), 1.4–1.6 (m, 1H), 1.04(s, 3H)

IR(KBr):ν($cm^{-1}$)=3420, 2938, 2722, 1692, 1640, 1582, 1537, 1481, 1235, 1040, 754, 691.

EXAMPLE 27

Preparation of 5-[3′-(4″-tetrahydropyranyl)oxybenzoylamino]-10-methyl-$\Delta^{1(2),8(9)}$-octalin-2-carboxylic acid (Compound No. 403 in Table 1)

The reaction was effected with 3-(4′-tetrahydropyranyl) oxybenzoic acid (313 mg, 1.41 mmol) in the same manner as in Example 7 to give the titled compound (229 mg, yield 39% ).

m.p.83°-85° C.

$^1$H-NMR($CDCl_3$, 250MHz)δ=7.39(d, 1H, 1.4Hz), 7.34(d, 1H, 7.8Hz), 7.20(s-like, 1H), 7.06(ddd, 1H, 1.3Hz, 1.1Hz, 8.2Hz), 6.03(d, 1H, 9.6Hz), 5.92(s-like, 1H), 4.5–4.7(m, 1H), 4.1–4.3(m, 1H), 3.9–4.1 (m, 2H), 3.5–3.7(m, 2H), 1.7–2.6(m, 11H), 1.3–1.5(m, 1H), 1.03(s, 3H)

IR(KBr):ν($cm^{-1}$)=3422, 2934, 1688, 1636, 1580, 1539, 1483, 1431, 1304, 1233, 1186.

EXAMPLE 28

Preparation of 5-[3′-(4″-heptyloxy)benzoylamino]-10-methyl-$\Delta^{1(2),8(9)}$-octalin-2-carboxylic acid (Compound No. 423 in Table 1)

The reaction was effected with 3-(4′-heptyloxy)benzoic acid (296 mg, 1.26 mmol) in the same manner as in Example 7 to give the titled compound (297 mg, yield 56%).

m.p.153°-156° C.

$^1$H-NMR($CDCl_3$, 250MHz)δ=7.1–7.3(m, 4H), 7.00(dd, 1H, 1.4Hz, 8.0Hz), 5.98(d, 1H, 10Hz), 5.90(t, 1H, 3.4Hz), 4.31(t, 1H, 5.7Hz), 4.18(ddd, 1H, 5.2Hz, 10Hz and 10Hz), 2.53(dd, 1H, 5.6Hz, 18.7Hz), 2.1–2.5(m, 3H), 1.3–2.0(m, 12H), 1.01(s, 3H), 0.90(t, 6H, 7.2Hz)

IR (KBr):ν($cm^{-1}$)=3297, 2959, 2872, 1684, 1636, 1580, 1541, 1305, 1277, 1235.

EXAMPLE 29

Preparation of 5-[3′-(2″,4″-dimethyl-3″-pentyloxy)benzoylamino]-10-methyl-$\Delta^{1(2),8(9)}$-octalin-2-carboxylic acid (Compound No. 481 in Table 1)

The reaction was effected with 3-(2′,4′-dimethyl-3′-pentyloxy)benzoic acid (235 mg, 0.99 mmol) in the same manner as in Example 7 to give the titled compound (203 mg, yield 51%).

m.p.190°-192° C.

$^1$H-NMR($CDCl_3$, 250MHz)δ=7.10–7.40(m, 4H), 7.04(dd, 1H, 2.7Hz, 8.1Hz), 5.97(d, 1H, 9.6Hz), 5.90(dd, 1H, each 3.7Hz), 4.10–4.15(m, 1H), 3.96(t, 1H, 5.8Hz), 2.1–2.6(m, 4H), 1.3–2.1(m, 6H), 1.01, 0.96, 0.93, 0.90(each s, each 3H), 0.92(s, 6H)

IR(KBr):ν($cm^{-1}$)=3347, 2965, 1682, 1638, 1578, 1541, 1508, 1474, 1458, 1426, 1285, 1236, 1123.

EXAMPLE 30

Preparation of 5-(3′-dicyclopropylmethoxybenzoylamino)-10-methyl-$\Delta^{1(2),8(9)}$-octalin-2-carboxylic acid (Compound No. 529 in Table 1)

The reaction was effected with 3-dicyclopropylmethoxybenzoic acid (307 mg, 1.32 mmol) in the same manner as in Example 7 to give the titled compound (203 mg, yield 36%).

m.p.129°-132° C.

$^1$H-NMR($CDCl_3$, 250MHz)δ=7.23-7.40(m, 3H), 7.18(br-s, 1H), 7.03(ddd, 1H, 1.5Hz, 6.0Hz, 7.4Hz, 5.98(d, 1H, 9.65Hz), 5.90 (br-s, 1H), 4.12-4.23(m, 1H), 3.53(t, 1H, 7.0Hz), 2.52(dd, 1H, 5.2Hz, 18Hz), 2.1-2.5(m, 3H), 1.7-1.95(m, 3H), 1.44(ddd, 1H, 5.5Hz, 5.5Hz and 13.1Hz), 1.0-1.2(m, 2H), 1.01(s, 3H), 0.6-0.8(m, 4H), 0.4-0.6(m, 4H)

IR(KBr):ν($cm^{-1}$)=3341, 3081, 3009, 2938, 1672, 1634, 1580, 1545, 1485, 1429, 1304, 1233, 1211, 1003, 982.

EXAMPLE 31

Preparation of 5-(3'-cyclohexylmethoxybenzoylamino)-10-methyl-$\Delta^{1(2),8(9)}$-octalin-2-carboxylic acid (Compound No. 424 in Table 1)

The reaction was effected with 3-cyclohexylmethoxybenzoic acid (472 mg, 2.01 mmol) in the same manner as in Example 7 to give the titled compound (406 mg, yield 48%).

m.p.159°-161° C.

$^1$H-NMR($CDCl_3$, 250MHz)δ=7.1-7.4(m, 4H), 7.01 (dd, 1H, 1.3Hz, 7.0Hz), 5.99(d, 1H, 9.7Hz), 5.90(dd, 1H, each 3.9Hz), 4.1-4.3(m, 1H), 3.78(d, 2H, 6.1Hz), 2.1-2.6 (m, 4H), 1.6-1.95(m, 9H), 1.45(ddd, 5.5Hz, 12.7Hz and 12.7Hz), 0.90-1.30(m, 5H), 1.01(s, 3H)

IR(KBr):ν($cm^{-1}$)=3275, 2930, 2853, 1680, 1636, 1611, 1582, 1543, 1449, 1429, 1319, 1277, 1240, 1038.

EXAMPLE 32

Preparation of 5-(3'-dicyclohexylmethoxybenzoylamino)-10-methyl-$\Delta^{1(2),8(9)}$-octalin-2-carboxylic acid (Compound No. 442 in Table 1)

The reaction was effected with 3-dicyclohexylmethoxybenzoic acid (293 mg, 0.93 mmol) in the same manner as in Example 7 to give the titled compound (257 mg, yield 54%).

m.p.142°-146° C.

$^1$H-NMR($CDCl_3$, 250MHz)δ=7.1-7.35(m, 4H), 7.03(dd, 1H, 1.8Hz, 8.0Hz), 5.98(d, 1H, 9.7Hz), 5.90 (dd, 1H, each 3.6Hz), 4.1-4.3(m, 1H), 3.99(t, 1H, 5.8Hz), 2.1-2.6(m, 4H), 1.5-1.95(m, 15H), 1.4-1.5 (m, 1H), 1.0-1.3(m, 10H), 1.02(s, 3H)

IR(KBr):ν($cm^{-1}$)=3447, 2928, 2853, 1682, 1636, 1580, 1541, 1522, 1481, 1456, 1316, 1277, 1235.

EXAMPLE 33

Preparation of 5-[3'-(4''-morpholinomethyl)benzoylamino]-10-methyl-$\Delta^{1(2),8(9)}$-octalin-2-carboxylic acid (Compound No. 577 in Table 1)

The reaction was effected with 3-(4''-morpholinomethyl)benzoic acid (500 mg, 2.26 mmol) in the same manner as in Example 1 to give the titled compound (327 mg, yield 35.1%).

m.p. (amorphous)

$^1$H-NMR($CDCl_3$, 250MHz)δ=7.76(s, 1H), 7.64 (d, 1H, J=7.5Hz), 7.50(d, 1H, J=7.5Hz), 7.40(t, 1H, J=7.5Hz), 7.10(d, 1H, J=1.9Hz), 5.87(t, 1H, J=3.5Hz), 3.91-4.25(m, 5H), 3.70(s, 2H, 2.85-3.17 (m, 4H), 2.16-2.54(m, 4H), 1.81-1.92 (m, 3H), 1.36-1.51 (m, 1H), 1.12 (s, 3H)

IR(KBr):ν($cm^{-1}$)=3395, 2935, 1687, 1642, 1539, 1454, 1304, 1263, 1213, 1127, 1078.

EXAMPLE 34

Preparation of 5-[3'-(1''-piperidinomethyl)benzoylamino]-10-methyl-$\Delta^{1(2),8(9)}$-octalin-2-carboxylic acid (Compound No. 578 in Table 1)

The reaction was effected with 3-(1-piperidinomethyl)benzoic acid (338 mg, 1.54 mmol) in the same manner as in Example 1 to give the titled compound (328 mg, yield 52.2%).

m.p. (amorphous)

$^1$H-NMR($CDCl_3$, 250MHz)δ=8.54(s, 1H), 7.96(t, 1H, J=1.8Hz), 7.39, 7.51(m, 3H), 7.11(d, 1H, J=1.9Hz), 5.82(t, 1H, J=3.5Hz), 4.00-4.28(m, 3H), 2.84-3.22 (m, 4H), 1.76-2.53(m, 9H), 1.54-1.71 (m, 2H), 1.35-1.50(m, 1H), 1.12(s, 3H)

IR(KBr):ν($cm^{-1}$)=3422, 2942, 1644, 1541, 1454, 1316, 1213, 1046.

EXAMPLE 35

Preparation of 5-(3'-cyclohexylmethylbenzoylamino)-10-methyl-$\Delta^{1(2),8(9)}$-octalin-2-carboxylic acid (Compound No. 579 in Table 1)

The reaction was effected with 3-cyclohexylmethylbenzoic acid (352 mg, 1.61 mmol) in the same manner as in Example 7 to give the titled compound (296 mg, yield 63%).

m.p.182°-183° C.

$^1$H-NMR($CDCl_3$, 250MHz)δ=7.45-7.60(m, 2H), 7.15-7.40(m, 3H), 5.98(d, 1H, 12.2Hz), 5.90(br-s, 1H), 4.1-4.3(m, 1H), 2.52(d, 2H, 6.9Hz), 2.1-2.6(m, 4H), 1.35-2.00(m, 10H), 0.8-1.3(m, 5H), 1.02(s, 3H)

IR(KBr):ν($cm^{-1}$)=3277, 2924, 2851, 1674, 1634, 1541, 1451, 1426, 1306, 1275.

EXAMPLE 36

Preparation of 5-(3'-cycloheptylmethylbenzoylamino)-10-methyl-$\Delta^{1(2),8(9)}$-octalin-2-carboxylic acid (Compound No. 581 in Table 1)

The reaction was effected with 3-cycloheptylmethyl benzoic acid (50.8 mg, 0.219 mmol) in the same manner as in Example 7 to give the titled compound (45.5mg, yield 49%).

m.p.171°-173° C.

$^1$H-NMR($CDCl_3$, 250MHz)δ=7.59(br-s, 1H), 7.52(ddd, 1H, 1.2Hz, 1.2Hz and 8.0Hz), 7.1-7.4(m, 3H), 5.98(d, 1H, 8.9Hz), 5.92(br-s, 1H), 2.57(d, 2H, 7.2Hz), 2.1-2.6(m, 4H), 1.1-1.95(m, 17H), 1.02(s, 3H)

IR(KBr):ν($cm^{-1}$)=3293, 2922, 2853, 1684, 1636, 1541, 1458, 1275, 1088.

EXAMPLE 37

Preparation of 5-[3-bromo-5-(p-isopropylphenoxy) benzoylamino]-10-methyl-$\Delta^{1(2),8(9)}$-octalin-2-carboxylic acid (Compound No. 596 in Table 1)

The reaction was effected with 3-bromo-5-(p-isopropylphenoxy)benzoic acid (498 mg, 1.49 mmol) in the same manner as in Example 1 to give the titled compound (520 mg, yield 67%).

m.p.62°-65° C.

$^1$H-NMR($CDCl_3$, 250MHz)δ=7.51(dd, 1H, each 1.4Hz), 7.31(dd, 1H, each 1.4Hz), 7.15-7.25(m, 4H), 6.95(d, 2H, 8.6Hz), 5.85-5.95(m, 2H), 4.05-4.20(m, 1H), 2.84–2.97(m, 1H), 2.1–2.6 (m, 4H), 2.75–2.90 (m, 3H), 1.35–2.50(m,1H), 1.23, 1.26 (each s, each 3H)

IR(KBr):ν($cm^{-1}$)=3308, 3079, 2961, 1682, 1638, 1570, 1541, 1426, 1305, 1277, 1238, 1206, 1171, 858.

EXAMPLE 38

Preparation of 5-[3',5'-di(p-isopropylphenoxy)benzoylamino]-10-methyl-$\Delta^{1(2),8(9)}$-octalin-2-carboxylic acid (Compound No. 597 in Table 1)

The reaction was effected with 3,5-di(p-isopropylphenoxy)benzoic acid (478 mg, 1.22 mmol) in the same manner as in Example 1 to give the titled compound (340 mg, yield 48%).

m.p.158°–159° C.

$^1$H-NMR($CDCl_3$, 250MHz)δ=7.10–7.20(m, 5H), 7.02(d, 2H, 2.2Hz), 6.94(d, 4H, 8.6Hz), 6.71 (dd, 1H, each 2.2Hz), 5.82–5.90(m, 2H), 4.02–4.20(m, 1H), 2.80–2.95(m, 2H), 2.10–2.60(m, 4H), 2.70–2.90(m, 3H), 1.30–1.50(m, 3H), 1.30–1.50(m, 1H), 1.21, 1.24(each s, each 3H), 0.95(s, 3H)

IR(KBr):ν($cm^{-1}$)=3291, 2963, 2936, 2872, 1682, 1640, 1609, 1588, 1555, 1505, 1435, 1327, 1283, 1217, 1173, 1123, 1005, 835.

EXAMPLE 39

Preparation of 5-(3'-cycloheptyloxy-4'-methoxybenzoylamino)-10-methyl-$\Delta^{1(2),8(9)}$-octalin-2-carboxylic acid (Compound No. 139 in Table 1)

The reaction was effected with 3-cycloheptyloxy-4-methoxybenzoic acid (319 mg, 1.21 mmol) in the same manner as in Example 7 to give the titled compound (278 mg, yield 50%).

m.p.127°–129° C.

$^1$H-NMR($CDCl_3$, 250MHz)δ=7.38(d, 1H, 2.0Hz), 7.17–7.21(m, 2H), 6.85(d, 1H, 8.5Hz), 5.89–5.95 (m, 2H), 4.39–4.50 (m, 1H), 4.11–4.23 (m, 1H), 3.87(s, 3H), 2.52(dd, 1H, 5.0Hz, 18.1Hz), 2.01–2.48 (m, 5H), 1.35–1.95(m, 14H), 1.01(s, 3H)

IR(KBr):ν($cm^{-1}$)=3447, 3291, 2932,. 2861, 1680, 1634, 1507, 1269.

EXAMPLE 40

Preparation of 5-(3',4'-methylenedioxybenzoylamino)-10-methyl-$\Delta^{1(2),8(9)}$-octalin-2-carboxylic acid (Compound No. 598 in Table 1)

The reaction was effected with piperonylic acid (217 mg, 1.31 mmol) in the same manner as in Example 7 to give the titled compound (293 mg, yield 61%).

m.p.(amorphous)

$^1$H-NMR($CDCl_3$, 250MHz)δ=7.20–7.30(m, 2H), 7.18(d, 1H, 1.7Hz), 6.82(d, 1H, 7.4Hz), 6.01(s, 2H), 5.91–5.95(m, 2H), 4.10–4.21(m, 1H), 4.52(dd, 1H, 4.1Hz, 18Hz), 2.1–2.5(m, 3H), 1.75–1.95(m, 3H), 1.42(ddd, 1H, 5.5Hz, 12.7Hz and 12.7Hz), 1.00(s, 3H)

IR(KBr):ν($cm^{-1}$)=3314, 2934, 1699, 1636, 1541, 1505, 1487, 1439, 1259, 1209, 1182, 1038.

EXAMPLE 41

Preparation of 5-(3',4'-ethylenedioxybenzoylamino)-10-methyl-$\Delta^{1(2),8(9)}$-octalin-2-carboxylic acid (Compound No. 600 in Table 1)

The reaction was effected with 3,4-ethylenedioxybenzoic acid (214 mg, 1.19 mmol) in the same manner as in Example 7 to give the titled compound (188 mg, yield 43%).

m.p. (amorphous)

$^1$H-NMR($CDCl_3$, 250MHz)δ=7.27–7.30(m, 2H), 7.17(br-s, 1H), 6.89(d, 1H, 8.3Hz), 5.84–5.90(m, 2H), 4.27(s, 4H), 4.08–4.25 (m, 1H), 2.51(dd, 1H, 4.5Hz, 18.4Hz), 2.10–2.47(m, 3H), 1.75–1.90 (m, 3H), 1.42 (ddd, 1H, 5.7Hz, 5.7Hz, 13.1Hz), 1.00(s, 3H)

IR(KBr):ν($cm^{-1}$)=3341, 2936, 1684, 1634, 1615, 1582, 1541, 1501, 1316, 1289, 1260, 1067.

EXAMPLE 42

Preparation of 5-(3',4'-cyclohexylidenedioxybenzoylamino)-10-methyl-$\Delta^{1(2),8(9)}$-octalin-2-carboxylic acid (Compound No. 602 in Table 1)

The reaction was effected with 3,4-cyclohexylidenedioxybenzoic acid (303 mg, 1.29 mmol) in the same manner as in Example 7 to give the titled compound (250 mg, yield 46%).

m.p.104°–105° C.

$^1$H-NMR($CDCl_3$, 250MHz)δ=7.24(dd, 1H, 1.8Hz, 8.1Hz), 7.14–7.18 (m, 2H), 6.73(d, 1H, 8.1Hz), 5.8–5.95(m, 2H), 4.15(ddd, 1H, 4.9Hz, 10Hz and 10Hz), 2.51 (dd, 1H, 5.3Hz, 19Hz), 2.15–2.45(m, 3H), 1.82–1.95 (m, 7H), 1.35–1.60 (m, 5H), 0.99(s, 3H)

IR(KBr):ν($cm^{-1}$)=3301, 2940, 1866, 1674, 1636, 1559, 1541, 1491, 1437, 1360, 1306, 1283, 1258.

EXAMPLE 43

Preparation of 5-(3',5'-di-t-butylbenzoylamino)-10-methyl-$\Delta^{1(2),8(9)}$-octalin-2-carboxylic acid (Compound No. 610 in Table 1)

The reaction was effected with 3,5-di-t-butylbenzoic acid (243 mg, 1.04 mmol) in the same manner as in Example 7 to give the titled compound (143 mg, yield 32%).

m.p.99°–101° C.

$^1$H-NMR($CDCl_3$, 250MHz)δ=7.55–7.57 (m, 3H), 7.18(br-s, 1H), 5.90–5.96(m, 2H), 4.16–4.30(m, 1H), 2.53(dd, 1H, 5.0Hz, 19Hz), 2.10–2.50(m, 3H), 1.70–1.90(m, 3H), 1.46(ddd, 1H, 5.7Hz, 5.7Hz, 13Hz), 1.34(s, 18H), 1.02(s, 3H)

IR(KBr):ν($cm^{-1}$)=3293, 2961, 1682, 1634, 1595, 1539, 1474, 1458, 1424, 1364, 1265, 1213, 706.

EXAMPLE 44

Preparation of 5-(5',6',7',8'-tetrahydro-5',5',8',8'-tetramethylnaphthalene-2'-carbonylamino)-10-methyl-$\Delta^{1(2),8(9)}$-octalin-2-carboxylic acid (Compound No. 616 in Table 1)

The reaction was effected with 5,6,7,8-tetrahydro-5,5,8,8-tetramethylnaphthalene-2-carboxylic acid (207 mg, 0.89 mmol) in the same manner as in Example 7 to give the titled compound (232 mg, yield 62% ).

m.p.109°–110° C.

$^1$H-NMR($CDCl_3$, 250MHz)δ=7.80(d,1H, 1.8Hz), 7.41(dd, 1H, 1.9Hz, 8.2Hz), 7.33(d, 1H, 8.2Hz), 7.17(d, 1H, 1.5Hz), 5.95(d, 1H, 9.7Hz), 5.90(dd, 1H, each 3.7Hz), 4.10–4.25(m, 1H), 2.10–2.60(m, 4H), 1.78 –1.95 (m, 3H), 1.68 (s, 4H), 1.44(ddd, 1H, 5.5Hz, 12.7Hz and 12.7Hz), 1.29, 1.30(each s, each 3H), 1.27(s, 6H), 1.01(s, 3H)

IR(KBr):ν($cm^{-1}$)=3310, 2961, 1684, 1634, 1559, 1539, 1267.

EXAMPLE 45

Preparation of (5R,10R)-5-(3'-cycloheptyloxybenzoylamino)-10-methyl-$\Delta^{1(2),8(9)}$-octalin-2-carboxylic acid (Compound No. 111 in Table 1)

The reaction was effected with 3-cycloheptyloxybenzoic acid (359 mg, 1.53 mmol) and (5R,10R)-5-amino-10-methyl-$\Delta^{1(2),8(9)}$-octalin-2-carboxylic acid methyl ester (339 mg, 1.53 mmol) in the same manner as in Example 7 to give the titled compound (370 mg, yield 57%).

$[\alpha]_D^{26}=+135°$ (c=0.50, MeOH)

m.p.133°-135° C.

$^1$H-NMR(CDCl$_3$, 250MHz)δ=7.1-7.4(m, 4H), 6.98-7.02(m, 1H), 6.01(br-d, 1H, 9.7Hz), 5.92(t-like, 1H, J≐1.0Hz), 4.20-4.35 (m, 1H), 4.1-4.3 (m, 1H), 2.1-2.6 (m, 4H), 2.0-2.1(m, 2H), 1.3-1.9(m, 8H), 1.03(s, 3H).

EXAMPLE 46

Preparation of (5S,10S)-5-(3'-cycloheptyloxybenzoylamino)-10-methyl-$\Delta^{1(2),8(9)}$-octalin-2-carboxylic acid (Compound No. 111 in Table 1)

The reaction was effected with 3-cycloheptyloxybenzoic acid (280 mg, 1.19 mmol) and (5S,10S)-5-amino-10-methyl-$\Delta^{1(2),8(9)}$-octalin-2-carboxylic acid methyl ester (264 mg, 1.19 mmol) in the same manner as in Example 7 to give the titled compound (271 mg, yield 54%).

$[\alpha]_D^{26}=-128°$ (c=0.50, MeOH)

$^1$H-NMR(CDCl$_3$, 250MHz)δ=7.1-7.4(m, 4H, 6.98-7.02(m, 1H), 6.01(br-d, 1H, 9.7Hz), 5.92(t-like, 1H, J≐1.0Hz), 4.20-4.35 (m, 1H), 4.1-4.3(m, 1H), 2.1-2.6(m, 4H), 2.0-2.1(m, 2H), 1.3-1.9 (m, 8H), 1.03(s, 3H).

EXAMPLE 47

Preparation of (5S,10S)-5-(3'-dicyclopropylmethoxybenzoylamino)-10-methyl-$\Delta^{1(2),8(9)}$-octalin-2-carboxylic acid (Compound No. 529 in Table 1)

The reaction was effected with 3-dicyclopropylmethoxybenzoic acid (105 mg, 0.48 mmol) and (5S,10S)-5-amino-10-methyl-$\Delta^{1(2),8(9)}$-octalin-2-carboxylic acid methyl ester (110 mg, 0.48 mmol) in the same manner as in Example 7 to give the titled compound (56 mg, yield 27%).

$[\alpha]_D^{27}=-126°$(c=0.50, MeOH)

m.p.97°-99° C.

$^1$H-NMR(CDCl$_3$, 250MHz)δ=7.23-7.40(m, 3H), 7.18(br-s, 1H), 7.03(ddd, 1H, 1.5Hz, 6.0Hz, 7.4Hz), 5.98(d, 1H, 9.65Hz), 5.90(br-s, 1H), 4.12-4.23(m, 1H), 3.53(t, 1H, 7.0Hz), 2.52(dd, 1H, 5.2Hz, 18Hz), 2.1-2.5(m, 3H), 1.7-1.95(m, 3H), 1.44(ddd, 1H, 5.5Hz, 5.5Hz and 13.1Hz), 1.0-1.2(m, 2H), 1.01(s, 3H), 0.6-0.8(m, 4H), 0.4-0.6(m, 4H).

EXAMPLE 48

Preparation of (5S,10S)-5-[3'-(2",4"-dimethyl-3"-pentyloxy)benzoylamino]-10-methyl-$\Delta^{1(2),8(9)}$-octalin-2-carboxylic acid (Compound No. 481 in Table 1)

The reaction was effected with 3-(2',4'-dimethy-3'-pentyloxy)benzoic acid (124 mg, 0.52 mmol) and (5S,10S)-5-amino-10-methyl-$\Delta^{1(2),8(9)}$-octalin-2-carboxylic acid methyl ester (116 mg, 0.52 mmol) in the same manner as in Example 7 to give the titled compound (216 mg, yield 66%).

$[\alpha]_D^{26}=-170°$(c=1.0, MeOH)

m.p.116°-118° C.

$^1$H-NMR(CDCl$_3$, 250MHz)δ=7.10-7.40(m, 4H), 7.04(dd, 1H, 2.7Hz, 8.1Hz), 5.97(d, 1H, 9.6Hz), 5.90(dd, 1H, each 3.7Hz), 4.10-4.15(m, 1H), 3.96(t, 1H, 5.8Hz), 2.1-2.6(m, 4H), 1.3-2.1(m, 6H), 1.01, 0.96, 0.93, 0.90(each s, each 3H), 0.92(s, 6H)

IR(KBr):ν(cm$^{-1}$)=3328, 2965, 2874, 1682, 1634, 1580, 1532, 1481, 1429, 1316, 1275, 1236, 1213, 1186, 1005, 752.

EXAMPLE 49

Preparation of (5S,10S)-N-methyl-5-[3'-(2",4"-dimethyl-3"-pentyloxy)benzoylamino]-10-methyl-$\Delta^{1(2),8(9)}$-octalin-2-carboxylic acid (Compound No. 497 in Table 1)

The reaction was effected with 3-(2',4'-dimethy-3'-pentyloxy)benzoic acid (137 mg, 0.58 mmol) and (5S,10S)-5-amino-10-methyl-$\Delta^{1(2),8(9)}$-octalin-2-carboxylic acid methyl ester (128 mg, 0.58 mmol) in the same manner as in Example 7 to give the titled compound (238 mg, yield 99%). This compound was dissolved in dimethylformamide (1 ml) and mixed with sodium hydride (27 mg, 0.66mmol), 0.5 hours later mixed with methyl iodide (0.055 ml, 0.89 mmol), and the resultant mixture was stirred for 3 hours. The reaction mixture was poured into chilled water, extracted with diethyl ether, and the extract was concentrated. The product was hydrolyzed and purified in the same manner as in Example 7 to give the titled compound (170 mg, yield 70%).

$[\alpha]_D^{27}=-166°$(c=0.33, MeOH)

m.p.(amorphous)

$^1$H-NMR(CDCl$_3$, DMSO-d$_6$, 373K, 250MHz)δ=7.27(dd, 1H, each 7.9Hz), 6.96(dd, 1H, 1.8Hz, 7.9Hz), 6.80-6.90(m, 3H), 5.76(br-s, 1H), 5.76(br-s, 1H), 3.99(t, 1H, 5.6Hz), 2.90(s, 3H), 2.1-2.5(m, 5H), 1.9-2.1(m, 2H), 1.65-1.85(m, 2H), 1.1-1.3(m, 1H), 1.05(s, 3H), 0.9-1.0(m, 12H)

IR(KBr):ν(cm$^{-1}$)=2965, 2874, 1701, 1684, 1634, 1578, 1456, 1404, 1364, 1316, 1256, 1209, 1005, 980, 793, 754.

EXAMPLE 50

Preparation of 5-(3'-cycloheptyloxy-4'-isopropyloxybenzoylamino)-10-methyl-$\Delta^{1(2),8(9)}$-octalin-2-carboxylic acid (Compound No. 117 in Table 1)

The reaction was effected with 3-cycloheptyloxy-4-isopropyloxybenzoic acid (157 mg, 0.54 mmol) and 5-amino-10-methyl-$\Delta^{1(2),8(9)}$-octalin-2-carboxylic acid methyl ester (125 mg, 0.54 mmol) in the same manner as in Example 7 to give the titled compound (128 mg, yield 48%).

m.p.143°-196° C.

$^1$H-NMR(CDCl$_3$, 250MHz)δ=7.38(d, 1H, 2.1Hz), 7.23(dd, 1H, 2.1Hz, 8.3Hz), 7.19(br-s, 1H), 6.89(d, 1H, 8.3Hz), 5.90-5.95 (m, 2H), 4.49-4.62(m, 1H), 4.30-4.46(m, 1H), 4.12-4.23(m, 1H), 2.53(dd, 1H, 5.1Hz, 19Hz), 2.15-2.48(m, 3H), 1.3-2.1(m, 16H), 1.32, 1.34(each s, each 3H), 1.01(s, 3H)

IR(KBr):ν(cm$^{-1}$)=2976, 2932, 2859, 1682, 1634, 1601, 1499, 1302, 1217, 1138, 1107, 1001, 954.

EXAMPLE 51

Preparation of 5-(3'-cycloheptyloxy-2-methylbenzoylamino)-10-methyl -$\Delta^{1(2),8(9)}$-octalin-2 -carboxylic acid (Compound No. 119 in Table 1)

The reaction was effected with 3-cycloheptyloxy-2-methylbenzoic acid (200 mg, 0.81 mmol) in the same manner as in Example 1 to give the titled compound (297 mg, yield 84.1%).

m.p.237°-239° C.

$^1$H-NMR(CDCl$_3$, 250MHz)δ=7.20(s, 1H), 7.16(dd, 1H, J=7.2Hz, 8.3Hz), 6.91(d, 1H, J=7.2Hz), 6.86(d, 1H, J=8.3Hz), 5.92(t, 1H, J=3.7Hz), 5.64(d, 1H, J=9.7Hz), 4.40-4.49(m, 1H), 4.14-4.24(m, 1H), 2.16-2.66(m, 3H), 2.29(s, 3H), 1.40-2.07(m, 17H), 0.96(s, 3H)

IR(KBr):ν(cm$^{-1}$)=3277, 2932, 2858, 1672, 1634, 1541, 1458, 1425, 1308, 1260, 1186, 1078.

EXAMPLE 52

Preparation of (1S,8S )-1-(3'-cycloheptyloxybenzoylamino)-8a-methyl-1,2,6,7-tetrahydroindene-5-carboxylic acid (Compound No. 135 in Table 1)

The reaction was effected with 3-cycloheptyloxybenzoic acid (104 mg, 0.44 mmol) and (1S,8S)-1-amino-8a-methyl-1,2,6,7-tetrahydroindene-5-carboxylic acid methyl ester (92 mg, 0.44 mmol) in the same manner as in Example 7 to give the titled compound (18 mg, yield 9.3%).

$^1$H-NMR(CDCl$_3$, 250MHz)δ=7.1-7.3(m, 4H), 6.89(dd, 1H, 1.8Hz, 7.4Hz), 6.73(br-d, 1H, 8.7Hz), 6.04(br-s, 1H), 4.3-4.5(m, 2H), 2.63(ddd, 1H, 3Hz, 7.6Hz, 17Hz), 2.1-2.5(m, 3H), 1.85-2.0(m, 3H), 1.30-1.8(m, 2H), 0.92(s, 1H)

IR(KBr):ν(cm$^{-1}$)=3380, 2930, 2857, 1686, 1640, 1580, 1483, 1238, 1181, 1086, 1019, 696.

EXAMPLE 53

Preparation of (1S,8S)-1-[3'-(2",4"-dimethyl-3"-pentyl)oxybenzoylamino]-8a-methyl-1,2,6,7-tetrahydroindene-5-carboxylic acid (Compound No. 505 in Table 1)

The reaction was effected with 3-(2',4'-dimethyl-3'-pentyl)oxybenzoic acid (64 mg, 0.27 mmol) and 1-amino-8a-methyl-1,2,6,7-tetrahydroindene-5-carboxylic acid methyl ester (56 mg, 0.27 mmol) in the same manner as in Example 7 to give the titled compound (25 mg, yield 22%).

$^1$H-NMR(CDCl$_3$, 250MHz)δ=7.1-7.4(m, 4H), 7.05(dd, 1H, 1.8Hz, 8.1Hz), 6.21(d, 1H, 8.8Hz), 5.87(br-s, 1H), 4.45-4.6(m, 1H), 3.96 (t, 1H, 5.7Hz), 2.81(ddd, 1H, 3.0Hz, 7.6Hz, 16.8Hz), 2.3-2.7(m, 3H), 1.9-2.1(m, 3H), 1.59 (ddd, 5.7Hz, 5.7Hz and 12.5Hz), 0.96, 0.95, 0.93, 0.92, 0.90(each s, each 3H)

IR(KBr):ν(cm$^{-1}$)=3374, 2965, 1686, 1638, 1580, 1539, 1481, 1283, 1240, 1198, 1003, 754.

EXAMPLE 54

Preparation of (1S,8S)-1-[3'-(dicyclopropylmethyloxy)benzoylamino]-8a-methyl-1,2,6,7-tetrahydroindene-5-carboxylic acid (Compound No. 553 in Table 1)

The reaction was effected with 3-(dicyclopropylmethyloxy)benzoic acid (72 mg, 0.31 mmol) and 1-amino-8a-methyl-1,2,6,7-tetrahydroindene-5-carboxylic acid methyl ester (64 mg, 0.31 mmol) in the same manner as in Example 7 to give the titled compound (29 mg, yield 22%).

$^1$H-NMR(CDCl$_3$, 250MHz)δ=7.2-7.4(m, 4H), 7.05(ddd, 1H, 2.2Hz, 2.2Hz, and 6.9Hz), 6.21(d, 1H, 8.9Hz), 5.87(br-s, 1H), 4.47-4.59 (m, 1H), 3.53(t, 1H, 7.0Hz), 2.81(ddd, 1H, 3Hz, 7.8Hz, 17Hz), 2.2-2.7(m, 3H), 2.04(dd, 1H, 4.2Hz, 13Hz), 1.59(ddd, 5.7Hz, 5.7Hz, and 12.5Hz), 1.0-1.2(m, 2H), 1.03(s, 3H), 0.4-0.6(m, 4H), 0.2-0.4(m, 4H)

IR(KBr):ν(cm$^{-1}$)=3364, 3083, 3009, 2961, 2930, 1686, 1638, 1582, 1539, 1483, 1296, 1240, 1198.

EXAMPLE 55

Preparation of 5-(3'-cycloheptyloxybenzenesulfonylamino)-10-methyl-$\Delta^{1(2),8(9)}$-octalin-2-carboxylic acid (Compound No. 620 in Table 1)

To a mixture of 5-amino-10-methyl-$\Delta^{1(2),8(9)}$-octalin-2-carboxylic acid methyl ester (108 mg, 0.49 mmol), triethylamine (0.65 ml) and methylene chloride (2.6 ml) was added 3-cycloheptyloxybenzenesulfonyl chloride (129 mg, 0.47 mmol), and the resultant mixture was stirred at room temperature for 1 hour, poured into chilled water and extracted with ethyl acetate. The extract was concentrated, and the residue was chromatographed on a silica gel column to give crude product (88 mg). This product was hydrolyzed in the same manner as in Example 7 to give the titled compound (62 mg, yield 30%).

m.p.124°-125° C.

$^1$H-NMR(CDCl$_3$, 250MHz)δ=7.30-7.40 (m, 3H), 7.09(br-s, 1H), 7.03(ddd, 1H, 2.4Hz and 6.8Hz), 5.77(t, 1H, 3.7Hz), 4.4-4.5(m, 1H), 4.38(br-d, 1H, 9.8Hz), 3.05-3.20 (m, 1H), 2.45(dd, 1H, 5.1Hz, 18.4Hz), 2.1-2.3(m, 3H), 1.3-2.1(m, 15H), 0.95-1.10(m, 1H), 0.87(s, 3H)

IR(KBr):ν(cm$^{-1}$)=3268, 2932, 2863, 2631, 2540, 1682, 1632, 1613, 1476, 1431, 1323, 1289, 1252, 1236, 1157, 1096, 1063.

EXAMPLE 56

Preparation of (5S,10S)-5-(3'-cycloheptyloxybenzenesulfonylamino)-10-methyl-$\Delta^{1(2),8(9)}$-octalin-2-carboxylic acid (Compound No. 620 in Table 1)

The reaction was effected with 3-cycloheptyloxy benzenesulfonyl chloride (142 mg, 0.51 mmol) and (5S,10S)-5-amino-10-methyl-$\Delta^{1(2),8(9)}$-octalin-2-carboxylic acid methyl ester (87 mg, 0.40 mmol) in the same manner as in Example 55 to give the titled compound (82 mg, yield 46%).

m.p.70°-72° C.

$^1$H-NMR(CDCl$_3$, 250MHz)δ=7.30-7.40(m, 3H), 7.09(br-s, 1H), 7.03(ddd, 1H, 2.4Hz and 6.8Hz), 5.77 (t, 1H, 3.7Hz), 4.4-4.5(m, 1H), 4.38(br-d, 1H, 9.8Hz), 3.05-3.20(m, 1H), 2.45(dd, 1H, 5.1Hz, 18.4Hz), 2.1-2.3(m, 3H), 1.3-2.1(m, 15H), 0.95-1.10(m, 1H), 0.87(s, 3H).

EXAMPLE 57

Preparation of 5-(3'-phenoxybenzoylamino)-5,6,7,8-tetrahydro-naphthalene-2-carboxylic acid (Compound No. 624 in Table 2)

The reaction was effected with 3-phenoxybenzoic acid (0.91 mg, 4.23 mmol) and 1-amino-6-trifluoromethanesulfonyl-1,2,3,4-tetrahydronaphthalene (1.5 g, 5.08 mmol) to give the condensation product (1.5 g, 73%). This product (0.537 mg, 1.09 mmol) was added to a mixture of palladium acetate (123 mg, 0.55 mmol), triphenyl phosphine (286 mg, 1.1 mmol), triethylamine (19.4 ml), methanol (50 ml) and tetrahydrofuran (50 ml), and the resultant mixture was reacted in an atmosphere of carbon monoxide for 24 hours. The reaction mixture was poured into water and extracted with ethyl acetate. The extract was concentrated, and the residue was hydrolyzed in the same manner as in Example 7 to give the titled compound (88 mg, yield 21%).

m.p.155°-160° C.

$^1$H-NMR($CDCl_3$+cat$CD_3OD$, 250MHz)δ=7.81(d-like, 2H, 4Hz), 7.30-7.55(m, 5H), 7.10-7.20(m, 2H), 6.95-7.10(m, 2H), 6.62-6.78 (m, 1H), 5.30-5.45(m, 1H), 2.80-2.95(m, 2H), 2.1-2.3 (m, 1H), 2.85-2.95 (m, 3H)

IR(KBr):ν($cm^{-1}$)=3274, 2936, 1694, 1632, 1578, 1534, 1481, 1429, 1269, 1233, 1200, 752, 691.

EXAMPLE 58

Preparation of 5-(3'-phenoxybenzoyl)amino-9-methyl-$\Delta^{1(2),8(9)}$-octalin-2-(2'-trans-propenoic acid) (Compound No. 640 in Table 3)

To a mixture of 3-phenoxybenzoic acid (93 mg, 0.44 mmol), triethylamine (0.31 ml, 2.2 mmol) and methylene chloride (3 ml) chilled at 0° C. was gradually added thionyl chloride (48 μl, 0.66 mmol), and the resultant mixture was stirred at 0° C. for 15 minutes. A solution of 5-amino-9-methyl-$\Delta^{1(2),8(9)}$-octalin-2-(2'-propenoic acid) methyl ester (114 mg, 0.44 mmol) in methylene chloride (3 ml) was added to the mixture, which was stirred at room temperature for 30 minutes. The reaction mixture was distributed between ethyl acetate and water, and the organic layer was washed with saturated brine and concentrated. The residue was dissolved in methanol (5 ml), mixed with 2N aqueous KOH (1 ml) and refluxed under heating for 1 hour. The reaction mixture was acidified with 2N hydrochloric acid, extracted with chloroform, dried and concentrated. The resulting residue was chromatographed on a silica gel column, eluting with chloroform-methanol to give the titled compound (60 mg, yield 32% ).

$^1$H-NMR($CDCl_3$, 250MHz)δ=7.34-7.49(m, 6H), 7.15(t, 2H, J=7.5Hz), 7.03(d, 2H, J=7.5Hz), 6.36(br s, 1H), 5.98(d, 1H, J=9.7Hz), 5.85(d, 1H, J=15.7Hz), 5.77(t, 1H, J=3.7Hz), 4.16-4.31 (m, 1H), 2.15-2.59(m, 3H), 1.82-1.92(m, 4H), 1.41-1.54(m, 1H), 1.03(s, 3H)

IR(KBr):ν($cm^{-1}$)=3426, 3289, 3065, 2938, 1674, 1634, 1605, 1580, 1547, 1481, 1318, 1277, 1232.

EXAMPLE 59

Preparation of 1-[5'-(3''-phenoxybenzoylamino)-5',6',7',8'-tetrahydro-2'-naphthyloxy]acetic acid (Compound No. 656 in Table 4)

The reaction was effected with 3-phenoxybenzoic acid (436 mg, 2.04 mmol) and 1-(5-amino-5',6',7',8'-tetrahydro-2'-naphthyloxy)acetic acid methyl ester (479 mg, 2.04 mmol) in the same manner as in Example 1 to give the titled compound (300 mg, yield 35%).

m.p.153°-1 57° C.

$^1$H-NMR($CDCl_3$+catDMSO-$d_6$, 250MHz)δ=7.35-7.45(m, 1H), 6.80-7.25(m, 9H), 6.58(dd, 1H, 2.7Hz, 8.5Hz), 5.1-5.2(m, 1H), 4.41(s, 2H), 2.5-2.7(m, 2H), 1.5-2.0(m, 4H)

IR(KBr):ν($cm^{-1}$)=3343, 2932, 2866, 1725, 1611, 1574, 1549, 1481, 1435, 1333, 1289, 1186, 1163, 1132, 1080, 760, 694.

EXAMPLE 60

Preparation of 1-[5'-(3''-benzyloxybenzoylamino)-5',6',7',8'-tetrahydro-2'-naphthyloxy]acetic acid (Compound No. 666 in Table 4)

The reaction was effected with 3-benzyloxybenzoic acid (398 mg, 1.74 mmol)and 1-(5'-amino-5',6',7',8'-tetrahydro-2'-naphthyloxy)acetic acid methyl ester (410 mg, 1.74 mmol ) in the same manner as in Example 1 to give the titled compound (127 mg, yield 17%).

m.p.(amorphous)

$^1$H-NMR($CDCl_3$+catDMSO-$d_6$, 250MHz)δ=7.1-7.4 (m, 8H), 6.95-7.05 (m, 1H), 6.5-6.8(m, 3H), 5.15-5.25 (m, 1H), 5.01(s, 2H), 4.47(s, 2H), 2.6-2.8(m, 2H), 1.95-2.10(m, 1H), 1.7-1.9(m, 3H)

IR(KBr):ν($cm^{-1}$)=3345, 2928, 2859, 1723, 1613, 1578, 1551, 1499, 1445, 1290, 1240, 1217, 1163, 1132, 1080, 1017, 756, 698.

REFERENCE EXAMPLE 1

Preparation of 5-amino-10-methyl-$\Delta^{1(2),8(9)}$-octalin-2-carboxylic acid methyl ester To a mixture of Wieland Mischer's ketone (38.5 g, 216 mmol), diisopropylethylamine (39.5 ml) and methylene chloride (770 ml) was added anhydrous trifluoromethanesulfonic acid (40 ml, 238 mmol) under ice cooling, and the resultant mixture was stirred at room temperature for 2 hours. The reaction mixture was mixed with hexane (120 ml), and the organic layer was washed with water, 3N hydrochloric acid, saturated aqueous sodium bicarbonate solution and saturated brine in this order, dried and concentrated to give monoenol triflate compound (63 g). This product was dissolved in a mixture of methanol (630 ml) and tetrahydrofuran (630 ml), mixed with palladium acetate (1.14 g, 5.08 mmol), trifphenyl phosphine (2.6 g, 10.1 mmol) and triethylamine (315 ml). Carbon monoxide was bubbled into the solution at room temperature for 50 hours. Then, the reaction mixture was diluted with hexane, poured into chilled water and extracted with ethyl acetate to give light yellow syrup (33 g). This product was dissolved in methanol (1.3 L), mixed with ammonium acetate (115 g, 1.45 mmol) and sodium cyanoborohydride (6.4 g, 102 mmol), and the mixture was refluxed for 6 hours. The reaction mixture was allowed to warm at room temperature, poured into chilled water and extracted with chloroform under weakly basic conditions. The organic layer was dried and concentrated. The residue was washed with hexane-diethyl ether to give the titled compound (16.2 g, yield 34%) as white powders.

$^1$H-NMR($CDCl_3$, 250MHz)δ=7.05(d, 1H), 5.78(t, 1H), 3.73(s, 3H), 2.62(d, 1H), 2.57(dd, 1H), 2.2-2.4(m,

3H), 1.95(ddd-like, 1H), 1.5–1.8(m, 3H), 1.1–1.3(m, 2H), 0.86(s, 3H).

REFERENCE EXAMPLE 2

Preparation of (5S,10S)-5-amino-10-methyl-$\Delta^{1(2),8(9)}$-octalin-2-carboxylic acid methyl ester The reaction was effected with (+)-Wieland Mischer's ketone (Fulka Company, $[\alpha]_D > +98°$ (c=1.0, benzene) (2.0 g, 11.2 mmol) in the same manner as in Reference Example 1 to give the titled compound (0.95 g, yield 57%).

$[\alpha]_D^{27} = -254°$(c=0.50, MeOH)

REFERENCE EXAMPLE 3

Preparation of (5R,10R)-5-amino-10-methyl-$\Delta^{1(2),8(9)}$-octalin-2-carboxylic acid methyl ester The racemate obtained in Reference Example 1 (2.27 g, 10.3 mmol) was recrystallized three times together with L-benzoyltartaric acid (3.86 g, 10.3 ml) in methanol. The crystals are collected under basic conditions and purified to give the titled compound (339 mg, yield 15%).

$[\alpha]_D^{26} = +244°$(c=0.5, MeOH)

REFERENCE EXAMPLE 4

Preparation of (1S,8S)-1-amino-8a-methyl-1,2,6,7-tetrahydro-indane-5-carboxylic acid methyl ester The reaction was effected with (+)-2,3,6,7-tetrahydro-8a-methyl-1,5-indadione ($[\alpha]_D^{29} > +358°$ (c=1.0, benzene) (2.95 g, 18.0 mmol) in the same manner as in Reference Example 1 to give the titled compound (408 g, yield 11%).

$^1$H-NMR($CDCl_3$, 250MHz)δ=7.19(d, 1H, 2.4Hz), 5.74(br-s-like), 3.72(s, 3H), 3.10(dd, 1H, 7.6Hz, 10.0Hz), 1.8–2.7 (m, 4H), 1.2–1.4 (m, 2H), 0.81 (s, 3H).

REFERENCE EXAMPLE 5

Preparation of 1-(1'-amino-1',2',3',4'-tetrahydro-2'-naphthyloxy)acetic acid methyl ester The reductive animation was effected with 1-(1'-oxo-1',2',3',4'-tetrahydro-2'-naphthyloxy)acetic acid methyl ester (9.0 g, 36.2 mmol), prepared from α-bromoacetic acid and 6-hydroxytetralone, in the same manner as in Reference Example 1 to give the titled compound (4.08 g, yield 48%).

$^1$H-NMR($CDCl_3$, 250MHz)δ=7.13(1H, d, 8.6Hz), 6.67(1H, dd, 2.7Hz and 8.6Hz), 6.56(d, 1H, 2.7Hz), 4.97–5.10(m, 1H), 4.55 (s, 2H), 3.75 (s, 3H), 2.60–2.80 (m, 2H), 1.65–2.05 (m, 4H).

REFERENCE EXAMPLE 6

Preparation of 5-amino-9-methyl-$\Delta^{1(2),8(9)}$-octalin-2-(2'-propenylic acid) ethyl ester To a solution of palladium acetate (126 mg, 0.56 mmol), triphenyl phosphine (292 mg, 1.12 mmol) and tetrahydrofuran (2.9 ml) previously prepared was dropwise added a solution of enol triflate (1.74 g, 5.61 mmol) as disclosed in Reference Example 1 in tetrahydrofuran (10 ml). The mixture was mixed with triethylamine (10 ml) and ethyl acetate (1.22 ml, 11.2 mmol), and stirred at room temperature for 3 days. The reaction mixture was diluted with ethyl acetate, and the organic layer was washed with water and saturated sodium bicarbonate solution, dried and concentrated. The residue was chromatographed on a silica gel column (40 g) eluting with hexane-ethyl acetate to give 5-oxo-9-methyl-$\Delta^{1(2),8(9)}$-octalin-2-(2'-propenoic acid) ethyl ester (0.6 g, yield 35%). This product was subjected to reductive amination in the manner as disclosed in Reference Example 1 to give the titled compound (114 mg, yield 22%).

$^1$H-NMR($CDCl_3$, 250MHz)δ=7.33(d, 1H, 15.7Hz), 6.31(s, 1H), 6.86(d, 1H, 15.7Hz), 5.70(t, 1H, 3.8Hz), 4.21(q, 2H, 7.1Hz), 2.83 (dd, 1H, 5.6Hz, 10.4Hz), 2.2–2.4(m, 5H), 2.0–2.18 (m, 1H), 1.7–1.9 (m, 2H), 1.30 (t, 3H, 7.1Hz), 0.99(s, 3H).

REFERENCE EXAMPLE 7

Preparation of 3-(p-t-butylphenoxy)benzoic acid

To a solution of 3-bromobenzonitrile (4.35 g, 23.9 mmol) and p-t-butylphenol (4.30 g, 28.7 mmol) in pyridine (45 ml) were added potassium carbonate (6.61 g, 47.8 mmol) and cupric oxide (3.42 g, 43 mmol), and the resultant mixture was refluxed for 46 hours. The reaction mixture was poured into saturated potassium hydrogensulfate solution and extracted with ethyl acetate. The organic layer was concentrated, and the residue was dissolved in ethylene glycol (20 ml), mixed with 2N potassium hydroxide solution (130 ml) and refluxed for 20 hours. The reaction mixture was poured into chilled water and extracted with diethyl ether under acidic conditions. The organic layer was dried and concentrated. The residue was chromatographed on a silica gel column to give the titled compound (3.46 g, yield 54%).

$^1$H-NMR($CDCl_3$, 250MHz)δ=7.80(d-like, 1H, 7.6Hz), 7.70(t, 1H, 1.9Hz), 7.42(d, 1H, 7.6Hz), 7.36(d, 2H, 8.6Hz), 7.24(dd, 1H, 1.9Hz, 7.6Hz), 6.94(d, 2H, 8.6Hz), 1.32(s, 9H).

The compounds of the following Reference Examples 8–16 were prepared according to Reference Example 7.

REFERENCE EXAMPLE 8

4 -phenoxybenzoic acid $^1$H-NMR($CDCl_3$, 250MHz)δ=7.98(d, 2H, 8.8Hz), 7.34(t, 2H, 7.7Hz), 7.14(t, 1H, 7.7Hz), 7.02(d, 2H, 8.8Hz), 6.93(d, 2H, 7.7Hz), 3.83 (br-s, 1H).

REFERENCE EXAMPLE 9

3-(o-isopropylphenoxy)benzoic acid

1H-NMR($CDCl_3$, 250MHz)δ=7.77(d, 1H, 7.8Hz), 7.61(br-s, 1H), 7.40(d, 1H, 8.0Hz), 7.35(t-like, 1H, 4.9Hz), 7.1–7.2(m, 3H), 6.85–6.90(m, 1H), 3.15–3.3(m, 1H), 1.19, 1.22(each s, each 3H).

REFERENCE EXAMPLE 10

3-(p-isopropylphenoxy)benzoic acid $^1$H-NMR($CDCl_3$, 250MHz)δ=7.80(ddd, 1H, 1.2Hz, 1.6Hz, 7.8Hz), 7.68(dd, 1H, 1.6Hz, 2.4Hz), 7.39(dd, 1H, 7.8Hz, 8.0Hz), 7.18–7.28 (m, 3H), 6.90–7.0(m, 2H), 2.80–3.00(m, 1H), 1.23, 1.26(each s, each 3H).

REFERENCE EXAMPLE 11

3-(m-isopropylphenoxy)benzoic acid $^1$H-NMR($CDCl_3$, 250MHz)δ=7.83(ddd, 1H, 1.2Hz, 1.5Hz, 7.7Hz), 7.72(dd, 1H, 1.2Hz, 2.8Hz), 7.42(dd, 1H, 7.9Hz, 8.0Hz), 7.2–7.3(m, 2H), 7.02(dd, -like, 1H, 0.7Hz, 7.2Hz), 6.92(br-s, 1H), 6.82(dd- like, 1.2Hz, 8.2Hz), 2.80–3.00(m, 1H), 1.23, 1.26(each s, each 3H).

REFERENCE EXAMPLE 12

3-[p-(2'-methylpropyl)phenoxy]benzoic acid $^1$H-NMR($CDCl_3$, 250MHz)δ=7.89(ddd, 1H, 1.2Hz, 1.7Hz, 7.7Hz), 7.67(dd, 1H, 2.4Hz, 1.7Hz), 7.40(t, 1H, 7.7Hz), 7.21(ddd, 1H, 1.2Hz, 2.4Hz, 7.7Hz), 7.11(d, 2H, 8.5Hz), 6.92(d, 2H, 8.5Hz), 3.75(br-s, 1H), 2.45(d, 2H, 7.2Hz), 1.84(dt, 1H, 6.5Hz, 7.2Hz), 0.90(d, 6H, 6.5Hz).

REFERENCE EXAMPLE 13

3-(p-tolyloxy)benzoic acid $^1$H-NMR($CDCl_3$, 250MHz)δ=7.79(ddd, 1H, 1.2Hz, 1.6Hz, 7.7Hz), 7.65(dd, 1H, 1.6Hz, 2.4Hz), 7.39(t, 1H, 7.7Hz), 7.21(ddd, 1.2Hz, 1.8Hz, 7.7Hz), 7.15(d, 2H, 8.6Hz), 6.92(d, 2H, 8.6Hz), 2.34(s, 3H).

REFERENCE EXAMPLE 14

3-(p-cyclohexylphenoxy)benzoic acid $^1$H-NMR($CDCl_3$, 250MHz)δ=7.80(dd-like, 1H, 1.2Hz, 8.0Hz), 7.68(dd, 1H, 1.2Hz, 2.4Hz), 7.39(t, 1H, 8.0Hz), 7.10–7.25(m, 3H), 6.93(d, 2H, 8.6Hz), 2.38–2.58(m, 1H), 1.68–1.96(m, 5H), 1.14–1.52 (m, 5H).

REFERENCE EXAMPLE 15

3-(2',4'-dimethylphenoxy)benzoic acid $^1$H-NMR($CDCl_3$, 250MHz)δ=7.81(dd, 1H, 1.6Hz, 7.7Hz), 7.68 (dd, 1H, 1.6Hz, 2.2Hz), 7.40 (dd, 1H, 7.7Hz, 7.9Hz), 7.22(dd-like, 2.2Hz, 7.9Hz), 6.77(br-s, 1H), 6.63(br-s, 2H), 2.28(s, 6H).

REFERENCE EXAMPLE 16

3 (5',6',7',8'-tetrahydro-2'-naphthyloxy)benzoic acid $^1$H-NMR($CDCl_3$, 250MHz)δ=7.79(br-d, 1H, 7.7Hz), 7.67(br-s, 1H), 7.40(t, 1H, 7.7Hz), 7.23(dd, 1H, 2.4Hz, 7.7Hz), 7.04(d, 1H, 8.0Hz), 6.7–6.8(m, 2H), 2.7–2.8(m, 4H), 1.7–1.9 (m, 4H).

REFERENCE EXAMPLE 17

Preparation of 3-bromo-5-(p-isopropylphenoxy)benzoic acid (a) and 3,5-di(p-isopropylphenoxy)benzoic acid (b)

To a solution of 3,5-dibromobenzoic acid (3.8 g, 11 mmol) and p-isopropylphenol (3.36 g, 24.2 mmol) in pyridine (46 ml) were added cupric oxide (2.19 g, 27.5 mmol) and potassium carbonate (6.08 g, 44 mmol), and the resultant mixture was refluxed for 5 days. The reaction mixture was allowed to warm up to room temperature, poured into chilled water and extracted with chloroform under acidic conditions. The organic layer was concentrated, and the residue was chromatographed on a silica gel column to give the titled compounds (a) (489 mg, yield 13%) and (b) (1.88 g, yield 44%).

(a); $^1$H-NMR($CDCl_3$, 250MHz)δ=7.19(dd 1H, each 1.7Hz), 7.60 (dd, 1H, each 1.7Hz), 7.34(dd, 1H, each 1.7Hz), 7.23(d, 2H, 8.2Hz), 6.95(d, 2H, 8.2Hz), 2.8–3.0(m, 1H), 1.24, 1.27(each s, each 3H)

(b); $^1$H-NMR($CDCl_3$, 250MHz)δ=7.34(d, 2H, 2.1Hz), 7.19(m, 4H, 8.5Hz), 6.94(d, 4H, 8.5Hz), 6.86(d, 1H, 2.1Hz), 2.80–2.95(m, 2H), 1.22, 1.25(each s, each 6H).

REFERENCE EXAMPLE 18

Preparation of 3-dicyclohexylmethoxybenzoic acid

To a solution of 3-hydroxybenzoic acid (1.61 g, 8.2 mmol), dicyclohexylmethanol (1.61 g, 8.2 mmol), triphenylphosphine (2.05 g, 7.82 mmol) and dioxane (35 ml) was added diethyl azodicarboxylate (1.41 ml, 8.94 mmol), and the resultant mixture was refluxed for 3 days. The reaction mixture was allowed to warm up to room temperature, poured into chilled water and extracted with diethyl ether. The organic layer was concentrated, and the residue was dissolved in a mixture of methanol (20 ml), tetrahydrofuran (6.5 ml) and water (2.0 ml), mixed with potassium hydroxide (1.16 g) and stirred for 2 hours. The mixture was poured into chilled water, acidified, and extracted with ethyl acetate. The organic layer was concentrated, and the resultant residue was recrystallized from hexane to give the titled compound (0.43 g, yield 18%).

$^1$H-NMR($CDCl_3$, 250MHz)δ=7.55–7.65(m, 2H), 7.30(dd, 1H, each 8.4Hz), 7.13(ddd, 1H, 0.9Hz, 2.5Hz, 8.4Hz), 3.98(t, 1H, 5.6Hz), 1.50–1.88(m, 12H), 0.96–1.34(m, 10H).

The compounds of the following Reference Examples 19–24 were prepared according to Reference Example 18.

REFERENCE EXAMPLE 19

3-(2',4'-dimethyl-3'-pentoxy)benzoic acid $^1$H-NMR($CDCl_3$, 250MHz)δ=7.55–7.65(m, 2H), 7.32(t, 1H, 8.2Hz), 7.15(ddd, 1H, 1.0Hz, 2.7Hz, 8.2Hz), 3.94(t, 1H, 5.8Hz), 2.01(dt, 2H, 6.8Hz, 13.3Hz), 0.90–0.98(m, 12H).

REFERENCE EXAMPLE 20

3-(dicyclopropylmethoxy)benzoic acid $^1$H-NMR($CDCl_3$, 250MHz)δ=7.50–7.61(m, 2H), 7.28(t, 1H, 8.2Hz), 7.10(ddd, 1H, 1.2Hz, 2.7Hz, 8.2Hz), 3.88(s, 3H), 3.49(t, 1H, 6.9Hz), 1.0–1.2(m, 2H), 0.4–0.6(m, 4H), 0.2–0.4(m, 4H).

REFERENCE EXAMPLE 21

3-(cyclooctyloxy)benzoic acid $^1$H-NMR($CDCl_3$, 250MHz)δ=7.66(ddd, 1H, 1.2Hz, 2.3Hz and 8.0Hz), 7.57(dd, 1H, 2.3Hz, 1.7Hz), 7.34(t, 8Hz), 7.09(ddd, 1.2Hz, 1.7Hz, 8.0Hz), 4.47(4.0Hz, 7.9Hz, 11.8Hz), 1.4–2.0 (m, 14H).

REFERENCE EXAMPLE 22

3-(4-heptyloxy)benzoic acid $^1$H-NMR($CDCl_3$, 250MHz)δ=7.64(ddd, 1.2Hz, 2.0Hz, 8.0Hz), 7.59(dd, 1H, 1.2Hz, 2.3Hz), 7.33(t, 1H, 8.0Hz), 7.10(ddd, 1.2Hz, 2.3Hz, 8.9Hz), 4.31(dt, 1H, 5.9Hz, 11.6Hz), 1.3–1.8(m, 8H), 0.91 (t, 6H, 7.0Hz).

REFERENCE EXAMPLE 23

3-(cyclohexylmethoxy)benzoic acid $^1$H-NMR($CDCl_3$, 250MHz)δ=7.68(1H, 2.2Hz, 7.7Hz), 7.60(d, 1H, 2.2Hz), 7.35(t, 1H, 7.7Hz), 7.12(dt, 1H, 2.0Hz, 7.7Hz), 3.79(d, 2H, 6.0Hz), 1.6–1.9(m, 6H), 1.0–1.4(m, 5H).

REFERENCE EXAMPLE 24

3-cycloheptyloxy-4-methoxybenzoic acid $^1$H-NMR($CDCl_3$, 250MHz)δ=7.63(dd, 1H, 2.0Hz, 8.5Hz), 7.50(d, 1H, 2.0Hz), 6.86(d, 1H, 8.5Hz), 4.42(ddd, 1H, 4.3Hz, 8.5Hz and 12.6Hz), 3.88(s, 3H), 3.86(s, 3H), 1.96–2.05(m, 2H), 1.62–1.94(m, 4H), 1.33–1.62(m, 6H).

REFERENCE EXAMPLE 25

Preparation of 3-isopropyl-4-cycloheptylbenzoic acid

To a solution of 3,4-dihydroxybenzoic acid ethyl ester (2.0 g, 11 mmol) in acetone (450 l) were added potassium carbonate (2.28 g, 16.5 mmol) and isopropylamide (1.03 ml, 11 mmol), and the resultant mixture was stirred at room temperature for 2 days. The reaction mixture was poured into chilled water and extracted with ethyl acetate under acidic conditions. The organic layer was concentrated, and the residue was chromatographed On a silica gel column to give a mixture (617 mg) of 3-hydroxy-4-isopropyloxybenzoic acid ethyl ester and its position isomer, 4-hydroxy-3-isopropyloxybenzoic acid ethyl ester (6:1). There was observed NOE of protons at 1'-position of the isopropyl group and 5-position. The reaction was effected using this mixture (617 mg) in the same manner as in Reference Example 18, and the resultant product was recrystallized from hexane to give the titled compound (370 mg, yield 12%).

$^1$H-NMR($CDCl_3$, 250MHz)δ=7.68(dd, 1H, 2.0Hz, 8.4Hz), 7.58(d, 1H, 2.0Hz), 6.90(d, 1H, 8.4Hz), 4.55–4.70(m, 1H), 4.35–4.50(m, 1H), 1.9–2.1(m, 2H), 1.3–1.9(m, 10H), 1.34–1.37(each s, each 3H).

REFERENCE EXAMPLE 26

Preparation of 3-cyclohexylmethylbenzoic acid

To a solution of 3-carboxybenzaldehyde (2.65 g, 17.7 mmol) in tetrahydrofuran (2.65 ml) was added a solution of cyclohexyl magnesium bromide in diethyl ether (53 mmol, 30 ml). This mixture was added to 3N hydrochloric acid (500 ml) and extracted with chloroform. The organic layer was concentrated, and the residue was chromatographed on a silica gel column to give the condensed product (1.35 g). The product was dissolved in methanol (27 ml), mixed with palladium hydroxide (135 mg) and hydrogenated. The reaction mixture was filtered through Celite, and the filtrate was concentrated. The residue was recrystallized from hexane to give the titled compound (0.84 g, yield 22%).

$^1$H-NMR($CDCl_3$, 250MHz)δ=7.85–8.00(m, 2H), 7.30–7.40(m, 2H), 2.54(d, 2H, 6.9Hz), 1.5–1.8(m, 6H), 1.1–1.3(m, 3H), 0.80–1.05(m, 2H).

REFERENCE EXAMPLE 27

Preparation of 3-cyclohexylmethylbenzoic acid

The titled compound was prepared according to Reference Example 26.

$^1$H-NMR($CDCl_3$, 250MHz)δ=7.85–7.95(m, 2H), 7.30–7.40(m, 2H), 2.56(d, 2H, 7.2Hz), 1.1–1.9(m, 13H).

EXPERIMENT

Human steroid 5α-reductase inhibiting effect was examined on the compounds of the present invention using human prostatic tissue.

Frozen human prostate was thawed on ice and minced into small pieces (~5mm$^3$). The minced tissue was homogenized with a Polytron homogenizer (Kinematica, Switzerland) in 40 vol. of 0.1M phosphate buffer at pH 5.5. The suspension was used as the source of 5α-reductase.

The reaction tube contained 50 nM (1α,2α-$^3$H(N))-tetstosterone (2.04 TBq/mmol, New England Nuclear, Massachusetts), a predetermined amount of an inhibitor, 0.5 mg of NADPH and 0.5 ml of prostatic suspension in a total final volume of 1 ml. For this test, DMSO solutions containing various amount of the inhibitor were employed.

Each reaction solution was incubated at 37° C. for 10 minutes and ethyl acetate (2 ml) chilled with ice was added for stopping the reaction. The organic layer was transferred to another test tube and evaporated to dryness under nitrogen. Each 50 μg of non radioactive testosterone, DHT, estradiol, androstenedione and androstandiol was added to the residue, and the wall of each test tube was washed with ethyl acetate (0.1 ml). The content of the tube was evaporated again and the residue was dissolved in chloroform (50 μl) and then applied to Whatman LK60DF silica plates (Whatman, N.J.), developing in chloroform:methanol (50:1). The bands of the substrates and products were identified by fluorescence (254 nm) and iodine, and the relevant silica gel was collected by scraping, mixed with toluene based liquid sincilator, and the radioactivity was counted. The radioactivities of DHT and androstandiol were combined for the calculation of 5α-reductase activity. The conversion rate from testosterone to DHT and androstandiol was 35%–45% in the control group which only the solvent was added in place of inhibitors. The radioactivity for the control group was postulated as 100%.

$IC_{50}$ were calculated from the data obtained from the above experiments. Table 5 shows the test results.

TABLE 5

| Experiment No. | $IC_{50}$ (μM) | Experiment No. | $IC_{50}$ (μl) |
|---|---|---|---|
| 1 | 3.3 | 23 | 0.30 |
| 2 | 0.83 | 31 | 0.41 |
| 4 | 0.81 | 35 | 0.16 |
| 5 | 0.46 | 37 | 0.30 |
| 7 | 0.21 | 39 | 0.39 |
| 9 | 0.52 | 42 | 0.77 |
| 11 | 0.25 | 43 | 0.23 |
| 13 | 0.66 | 45 | 0.61 |
| 14 | 0.44 | 46 | 0.30 |
| 15 | 4.21 | 47 | 0.16 |
| 17 | 0.18 | 48 | 0.065 |
| 20 | 0.27 | 51 | 0.91 |
| 22 | 0.52 | 54 | 0.16 |

Table 5 shows that the compounds of the present invention and salts thereof are useful as 5α-reductase inhibitors. Accordingly, they would be useful as therapeutic agents to diseases such as benign prostatic hyperplasia, ache, seborrhea, female hirsutism, prostatic cancer, male alopecia or the like, in which the reduction of DHT activity is expected to be effective for therapeutic treatment thereof.

What is claimed is:

1. A compound of the following formula

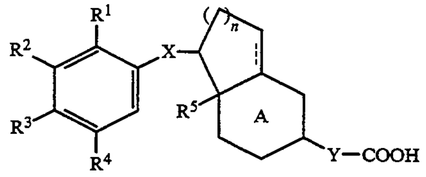

wherein $R^1$, $R^2$, $R^3$ and $R^4$ each independently represent hydrogen, halogen, $C_1$-$C_{14}$ alkyl or $C_1$-$C_{14}$ alkoxy, $R^5$ represents hydrogen or $C_1$-$C_5$ alkyl, X represents —$CONR^{13}$— wherein $R^{13}$ represents hydrogen or $C_1$-$C_6$ alkyl, Y represents a single bond, A ring represents a cyclohexene ring,
the dotted line represents a double bond, and
n represents 1 or 2, or a pharmaceutically acceptable salt thereof.

2. A compound according to claim 1, in which $R^1$, $R^2$, $R^3$ and $R^4$ each independently represent hydrogen, halogen, $C_1$-$C_{14}$ alkyl, or $C_1$-$C_{14}$ alkoxy, and x represents —$CONR^{13}$— wherein $R^{13}$ represents hydrogen.

3. A compound according to claim 2, in which $R^1$, $R^2$,$R^3$ and $R^4$ each independently represent hydrogen or $C_1$-$C_{14}$ alkoxy and n represents 2.

4. A compound according to claim 3, in which $R^1$, $R^3$ and $R^4$ represent hydrogen, $R^2$ represents 2,4-dimethyl-3-pentyloxy and $R^5$ represents methyl.

5. A pharmaceutical composition for the treatment of an androgen dependent disease which comprises an effective amount of a compound or pharmaceutically acceptable salt thereof as defined in claim 1 and a pharmaceutically acceptable carrier therefor.

6. A compound of the following formula

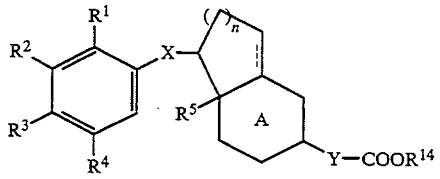

wherein
$R^1$, $R^2$, $R^3$ and $R^4$ each independently represent hydrogen, halogen, $C_1$-$C_{14}$ alkyl or $C_1$-$C_{14}$ alkoxy,
$R^5$ represents hydrogen or $C_1$-$C_5$ alkyl,
X represents —$CONR^{13}$— wherein $R^{13}$ represents hydrogen or $C_1$-$C_6$ alkyl,
Y represents a single bond,
A ring represents a cyclohexene ring,
the dotted line represents a double bond,
n represents 1 or 2, and
$R^{14}$ is $C_1$-$C_5$ alkyl.

* * * * *